United States Patent
Okamoto et al.

(10) Patent No.: US 12,269,889 B2
(45) Date of Patent: *Apr. 8, 2025

(54) HUMAN ANTIBODIES TO THE HUMAN GLUCAGON RECEPTOR (HGCGR) AND METHODS OF USE THEREOF TO LOWER BLOOD GLUCOSE OR KETONE LEVELS

(71) Applicant: Regeneron Pharmaceuticals, Inc., Tarrytown, NY (US)

(72) Inventors: Haruka Okamoto, New York, NY (US); Mark Sleeman, Richmond (AU); Joyce Harp, Montclair, NJ (US)

(73) Assignee: REGENERON PHARMACEUTICALS, INC., Tarrytown, NY (US)

(*) Notice: Subject to any disclaimer, the term of this patent is extended or adjusted under 35 U.S.C. 154(b) by 59 days.

This patent is subject to a terminal disclaimer.

(21) Appl. No.: 18/045,592

(22) Filed: Oct. 11, 2022

(65) Prior Publication Data
US 2023/0192874 A1 Jun. 22, 2023

Related U.S. Application Data

(60) Continuation of application No. 16/837,930, filed on Apr. 1, 2020, now Pat. No. 11,498,970, which is a continuation of application No. 16/256,190, filed on Jan. 24, 2019, now Pat. No. 10,640,566, which is a continuation of application No. 15/415,672, filed on Jan. 25, 2017, now Pat. No. 10,233,250, which is a division of application No. 14/821,652, filed on Aug. 7, 2015, now Pat. No. 9,587,029, which is a division of application No. 14/014,517, filed on Aug. 30, 2013, now Pat. No. 9,127,068, which is a continuation of application No. 13/301,944, filed on Nov. 22, 2011, now Pat. No. 8,545,847.

(60) Provisional application No. 61/551,032, filed on Oct. 25, 2011, provisional application No. 61/481,958, filed on May 3, 2011, provisional application No. 61/416,409, filed on Nov. 23, 2010.

(51) Int. Cl.
| | |
|---|---|
| C07K 16/28 | (2006.01) |
| A61K 39/00 | (2006.01) |
| A61K 39/395 | (2006.01) |
| A61K 45/06 | (2006.01) |
| C07K 16/40 | (2006.01) |
| C07K 16/46 | (2006.01) |
| C12N 15/113 | (2010.01) |
| C12N 15/64 | (2006.01) |
| C12N 15/70 | (2006.01) |

(52) U.S. Cl.
CPC .... *C07K 16/2869* (2013.01); *A61K 39/39541* (2013.01); *A61K 39/3955* (2013.01); *A61K 45/06* (2013.01); *C07K 16/40* (2013.01); *C07K 16/468* (2013.01); *C12N 15/1137* (2013.01); *C12N 15/64* (2013.01); *C12N 15/70* (2013.01); *A61K 2039/505* (2013.01); *A61K 2039/507* (2013.01); *C07K 2317/21* (2013.01); *C07K 2317/30* (2013.01); *C07K 2317/31* (2013.01); *C07K 2317/33* (2013.01); *C07K 2317/34* (2013.01); *C07K 2317/56* (2013.01); *C07K 2317/565* (2013.01); *C07K 2317/76* (2013.01); *C07K 2317/92* (2013.01); *C07K 2317/94* (2013.01); *C12N 2310/11* (2013.01); *C12N 2310/14* (2013.01); *C12N 2320/31* (2013.01)

(58) Field of Classification Search
CPC ............ C07K 16/2869; C07K 2317/21; A61K 39/39541; A61K 39/3955; A61K 2039/505
See application file for complete search history.

(56) References Cited

U.S. PATENT DOCUMENTS

| | | |
|---|---|---|
| 5,770,445 A | 6/1998 | Kindsvogel et al. |
| 5,776,725 A | 7/1998 | Kindsvogel et al. |
| 7,947,809 B2 | 5/2011 | Yan et al. |
| 7,968,686 B2 | 6/2011 | Korytko et al. |
| 8,088,731 B2 | 1/2012 | Knudsen et al. |
| 8,158,759 B2 | 4/2012 | Yan et al. |
| 8,545,847 B2 | 10/2013 | Okamoto et al. |
| 8,771,696 B2 | 7/2014 | Harp et al. |
| 9,102,732 B2 | 8/2015 | Lee et al. |

(Continued)

FOREIGN PATENT DOCUMENTS

| | | |
|---|---|---|
| EP | 2643355 | 10/2019 |
| WO | WO2007131237 A2 | 11/2007 |

(Continued)

OTHER PUBLICATIONS

Bloom, et al. (1973) "Release of Glucagon, Induced by Stress," Quarterly Journal of Experimental Physiology, 58:99-108.

(Continued)

*Primary Examiner* — Robert S Landsman
(74) *Attorney, Agent, or Firm* — FisherBroyles, LLP; Cara L. Crowley-Weber; Trisha Agrawal

(57) ABSTRACT

The present invention provides antibodies that bind to the human glucagon receptor, designated GCGR and methods of using same. According to certain embodiments of the invention, the antibodies are fully human antibodies that bind to human GCGR. The antibodies of the invention are useful for lowering blood glucose levels and blood ketone levels and are also useful for the treatment of diseases and disorders associated with one or more GCGR biological activities, including the treatment of diabetes, diabetic ketoacidosis and long-term complications associated with diabetes, or other metabolic disorders characterized in part by elevated blood glucose levels.

20 Claims, 6 Drawing Sheets
Specification includes a Sequence Listing.

(56) References Cited

U.S. PATENT DOCUMENTS

| | | | |
|---|---|---|---|
| 9,127,068 | B2 | 9/2015 | Okamoto et al. |
| 9,587,029 | B2 | 3/2017 | Okamoto et al. |
| 10,233,250 | B2 | 3/2019 | Okamoto et al. |
| 2002/0106629 | A1 | 8/2002 | Murphy et al. |
| 2009/0041784 | A1 | 2/2009 | Yan et al. |
| 2011/0212092 | A1 | 9/2011 | Korytko et al. |
| 2011/0223160 | A1 | 9/2011 | Yan et al. |
| 2013/0251728 | A1 | 9/2013 | Harp et al. |
| 2013/0344538 | A1 | 12/2013 | Okamoto et al. |
| 2015/0337045 | A1 | 11/2015 | Okamoto et al. |
| 2017/0129960 | A1 | 5/2017 | Okamoto et al. |
| 2020/0247896 | A1 | 8/2020 | Okamoto et al. |

FOREIGN PATENT DOCUMENTS

| | | |
|---|---|---|
| WO | WO2008036341 A2 | 3/2008 |
| WO | WO2009055783 A2 | 4/2009 |
| WO | WO2012071372 A2 | 5/2012 |

OTHER PUBLICATIONS

Brand, et al., (1994) "Immunoneutralization of Endogenous Glucagon with Monoclonal Glucagon Antibody Normalizes Hyperglycemia in Moderately Steptozotocin-diabetic Rats," Diabetologia, 37(10):985-993.

Buggy, et al., (1995) "Glucagon-Glucagon-Like Peptide 1 Receptor Chimeras Reveal Domains that Determine Specificity of Glucagon Binding," Journal Biological Chemistry, 270(13):7474-7478.

Buggy, et al., (1996) "Human Glucagon Receptor Monoclonal Antibodies: Antagonism of Glucagon Action and in Receptor Characterization," Hormone & Metabolic Research, 28(5):215-219.

Colman (1994) "A Structural View of Immune Recognition by Antibodies," Research in Immunology, Elseiver, NY 145(1):33-36.

Deane, et al., (2009) "The Effect of Exogenous Glucagon-Like Peptide-1 on the Glycaemic Response to Small Intestinal Nutrient in the Critically Ill: a Randomised Double-Blind Placebo-Controlled Cross Over Study," Critical Care, 13(3):R67.

Deane, et al., (2011) "Exogenous Glucagon-Like Peptide-1 Attenuates the Glycaemic Response to Postpyloric Nutrient Infustion in Critically Ill Patients with Type-2 Diabetes," Critical Care, 15(1):R35.

Jones, et al. (2012) "Minireview: Glucagon in Stress and Energy Homeostasis," Endocrinology, 153:1049-1054.

Kitabchi, et al., (Jul. 2009) "Hyperglycemic Crises in Adult Patients with Diabetes," Diabetes Care, 32:1335-1343.

Kyratsous, et al. (2015) "Reply to Dimitrov et al.: VelociSuite technologies are a foundation for rapid therapeutic antibody development.", PNAS, 112(37): E5116.

Macneil, et al., (1994) "Cloning and Expression of a Human Glucagon Receptor" Biochemical and Biophysical Research Communications, 198(1):328-334.

Murphy, et al. (2014) "Mice with megabase humanization of their immunoglobulin genes generate antibodies as efficiently as normal mice.", PNAS, 111(14):5153-5158.

Nauck, et al., (2004) "Blood Glucose Control in Health Subject and Patients Receiving Intravenous Glucose Infusion or Total Parenteral Nutrition Using Glucagon-Like Peptide 1," Science Direct, 118:89-97.

Paul, (1993) "Fundamental Immunology" 3rd ed., Raven Press, NY, Chapter 9, pp. 292-295.

Rocha, et al., (Apr. 5, 1973) "Abnormal Pancreatic Alpha-Cell Function in Bacterial Infections, " New England Journal of Medicine, 288(14):700-703.

Rudikoff, et al., (1982) "Single amino acid substitution altering antigen-binding specificity," Proc. Natl. Acad. Sci. USA, 79:1979-1983.

Runge, et al., (2003) "Mechanisms of Signal Transduction: Three Distinct Epitopes on the Extracellular Face of the Glucagon Receptor Determine Specificity for the glucagon Amino Terminus," Journal Biological Chemistry, 278(30):28005-28010.

The NICE-SUGAR Study Investigators, (Mar. 26, 2009) "Intensive versus Conventional Glucose Control in Critically Ill Patients," New England Journal of Medicine, 360(13):1283-1297.

Unson, et al., (1996) "Antibodies Against Specific Extracellular Epitopes of the Glucagon Receptor Block Glucagon Binding," Proc. Natl. Acad. Sci., 93(1):310-315.

Unson, et al., (2002) "Roles of Specific Extracellular Domains of the Glucagon Receptor in Ligand Binding and Signaling," Biochemistry, 41(39):11795-11803.

Van den Berghe, et al., (2001) "Intensive Insulin Therapy in Critically Ill Patients," New England Journal of Medicine, 345(19):1359-1367.

Van den Berghe, et al., (2006) "Intensive Insulin Therapy in Mixed Medical/Surgical Intensive Care Units," Diabetes, 55:3151-3159.

Wright, et al., (2000) "Structure of Fab hGR-2 F6, a Competitive Antagonist of the Glucagon Receptor," Acta Cryst. D 56(5):573-580.

International Search Report with respect to PCT/US2011/061766 mailed Nov. 8, 2012.

SEQUENCE LISTING

```
Sequence total quantity: 207
SEQ ID NO: 1            moltype = DNA   length = 375
FEATURE                 Location/Qualifiers
misc_feature            1..375
                        note = Synthetic
source                  1..375
                        mol_type = other DNA
                        organism = synthetic construct
SEQUENCE: 1
caggtccagt tggtacagtc tggggctgac gtgaagaagc ctggggcctc agtgaaggtc   60
tcctgcaagg tttccggaca tatcctcact gatttatcca tgcactgggt gcgacagcct  120
cctgaaaaag gacttgagtg gatggcaggt tttgatcctg aagaaggtaa aataatctac  180
gcacagaagt tccagggcag agtcaccatg accgaggaca catctacaga cacagcctac  240
atggagctga gcagcctgag atctggggac acggccgttt attactgtgc aacaagcgat  300
atttttgactg ggtattatag agactactac ggtttggacg tctggggcca agggaccacg  360
ctcaccgtct cctca                                                   375
```

```
SEQ ID NO: 2            moltype = AA  length = 125
FEATURE                 Location/Qualifiers
REGION                  1..125
                        note = Synthetic
source                  1..125
                        mol_type = protein
                        organism = synthetic construct
SEQUENCE: 2
QVQLVQSGAD VKKPGASVKV SCKVSGHILT DLSMHWVRQP PGKGLEWMAG FDPEEGKIIY    60
AQKFQGRVTM TEDTSTDTAY MELSSLRSGD TAVYYCATSD ILTGYYRDYY GLDVWGQGTT   120
LTVSS                                                               125

SEQ ID NO: 3            moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 3
ggacatatcc tcactgattt atcc                                           24

SEQ ID NO: 4            moltype = AA  length = 8
FEATURE                 Location/Qualifiers
REGION                  1..8
                        note = Synthetic
source                  1..8
                        mol_type = protein
                        organism = synthetic construct
SEQUENCE: 4
GHILTDLS                                                              8

SEQ ID NO: 5            moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 5
tttgatcctg aagaaggtaa aata                                           24

SEQ ID NO: 6            moltype = AA  length = 8
FEATURE                 Location/Qualifiers
REGION                  1..8
                        note = Synthetic
source                  1..8
                        mol_type = protein
                        organism = synthetic construct
SEQUENCE: 6
FDPEEGKI                                                              8

SEQ ID NO: 7            moltype = DNA  length = 54
FEATURE                 Location/Qualifiers
misc_feature            1..54
                        note = Synthetic
source                  1..54
                        mol_type = other DNA
                        organism = synthetic construct
SEQUENCE: 7
gcaacaagcg atattttgac tgggtattat agagactact acggtttgga cgtc          54

SEQ ID NO: 8            moltype = AA  length = 18
FEATURE                 Location/Qualifiers
REGION                  1..18
                        note = Synthetic
source                  1..18
                        mol_type = protein
                        organism = synthetic construct
SEQUENCE: 8
ATSDILTGYY RDYYGLDV                                                  18

SEQ ID NO: 9            moltype = DNA  length = 336
FEATURE                 Location/Qualifiers
misc_feature            1..336
                        note = Synthetic
source                  1..336
                        mol_type = other DNA
                        organism = synthetic construct
```

SEQUENCE: 9
gatattgtga tgactcagtc tccactcttc ctgcccgtca cccctggaga gccggcctcc    60
atctcctgca ggtctagtca gagcctcctg catagtaaag gatacaacta tttggattgg   120
tacctgcaga agccagggca gtctccacaa ctcctgatct atttgggttc taatcgggcc   180
tccggggtcc ctgacaggtt cagtggcagt ggatcaggca cagatttttac actgaaaatc   240
agcagagtgg aggctgaaga tgttggggtt tattactgca tgcaaactct acaaactcct   300
cggacgttcg gccaagggac caaggtggaa atcaaa                             336

```
SEQ ID NO: 10             moltype = AA   length = 112
FEATURE                   Location/Qualifiers
REGION                    1..112
                          note = Synthetic
source                    1..112
                          mol_type = protein
                          organism = synthetic construct
```
SEQUENCE: 10
DIVMTQSPLF LPVTPGEPAS ISCRSSQSLL HSKGYNYLDW YLQKPGQSPQ LLIYLGSNRA    60
SGVPDRFSGS GSGTDFTLKI SRVEAEDVGV YYCMQTLQTP RTFGQGTKVE IK           112

```
SEQ ID NO: 11             moltype = DNA   length = 33
FEATURE                   Location/Qualifiers
misc_feature              1..33
                          note = Synthetic
source                    1..33
                          mol_type = other DNA
                          organism = synthetic construct
```
SEQUENCE: 11
cagagcctcc tgcatagtaa aggatacaac tat                                 33

```
SEQ ID NO: 12             moltype = AA   length = 11
FEATURE                   Location/Qualifiers
REGION                    1..11
                          note = Synthetic
source                    1..11
                          mol_type = protein
                          organism = synthetic construct
```
SEQUENCE: 12
QSLLHSKGYN Y                                                         11

```
SEQ ID NO: 13             moltype =   length =
```
SEQUENCE: 13
000

```
SEQ ID NO: 14             moltype =   length =
```
SEQUENCE: 14
000

```
SEQ ID NO: 15             moltype = DNA   length = 27
FEATURE                   Location/Qualifiers
misc_feature              1..27
                          note = Synthetic
source                    1..27
                          mol_type = other DNA
                          organism = synthetic construct
```
SEQUENCE: 15
atgcaaactc tacaaactcc tcggacg                                        27

```
SEQ ID NO: 16             moltype = AA   length = 9
FEATURE                   Location/Qualifiers
REGION                    1..9
                          note = Synthetic
source                    1..9
                          mol_type = protein
                          organism = synthetic construct
```
SEQUENCE: 16
MQTLQTPRT                                                             9

```
SEQ ID NO: 17             moltype = DNA   length = 375
FEATURE                   Location/Qualifiers
misc_feature              1..375
                          note = Synthetic
source                    1..375
                          mol_type = other DNA
                          organism = synthetic construct
```
SEQUENCE: 17
caggtccagt tggtacagtc tggggctgac gtgaagaagc ctgggggcctc agtgaaggtc    60
tcctgcaagg tttccggaca tatcctcact gatttatcca tgcactgggt gcgacaggct   120
cctggaaaag ggcttgagtg gatggaggt tttgatcctg aagaaggtga atatctac      180
gcacagaagt tccagggcag agtcaccatg accgaggaca catctacaga cacagcctac   240

```
atggagctga gcagcctgag atctggggac acggccgttt attactgtgc aacaagcgat    300
attttgactg gttattatag agactactac ggtttggacg tctggggcca agggaccacg    360
ctcaccgtct cctca                                                    375
```

```
SEQ ID NO: 18          moltype = AA   length = 125
FEATURE                Location/Qualifiers
REGION                 1..125
                       note = Synthetic
source                 1..125
                       mol_type = protein
                       organism = synthetic construct
SEQUENCE: 18
QVQLVQSGAD VKKPGASVKV SCKVSGHILT DLSMHWVRQA PGKGLEWMGG FDPEEGEIIY     60
AQKFQGRVTM TEDTSTDTAY MELSSLRSGD TAVYYCATSD ILTGYYRDYY GLDVWGQGTT    120
LTVSS                                                                125

SEQ ID NO: 19          moltype = DNA   length = 24
FEATURE                Location/Qualifiers
misc_feature           1..24
                       note = Synthetic
source                 1..24
                       mol_type = other DNA
                       organism = synthetic construct
SEQUENCE: 19
ggacatatcc tcactgattt atcc                                            24

SEQ ID NO: 20          moltype = AA   length = 8
FEATURE                Location/Qualifiers
REGION                 1..8
                       note = Synthetic
source                 1..8
                       mol_type = protein
                       organism = synthetic construct
SEQUENCE: 20
GHILTDLS                                                               8

SEQ ID NO: 21          moltype = DNA   length = 24
FEATURE                Location/Qualifiers
misc_feature           1..24
                       note = Synthetic
source                 1..24
                       mol_type = other DNA
                       organism = synthetic construct
SEQUENCE: 21
tttgatcctg aagaaggtga aata                                            24

SEQ ID NO: 22          moltype = AA   length = 8
FEATURE                Location/Qualifiers
REGION                 1..8
                       note = Synthetic
source                 1..8
                       mol_type = protein
                       organism = synthetic construct
SEQUENCE: 22
FDPEEGEI                                                               8

SEQ ID NO: 23          moltype = DNA   length = 54
FEATURE                Location/Qualifiers
misc_feature           1..54
                       note = Synthetic
source                 1..54
                       mol_type = other DNA
                       organism = synthetic construct
SEQUENCE: 23
gcaacaagcg atattttgac tggttattat agagactact acggtttgga cgtc           54

SEQ ID NO: 24          moltype = AA   length = 18
FEATURE                Location/Qualifiers
REGION                 1..18
                       note = Synthetic
source                 1..18
                       mol_type = protein
                       organism = synthetic construct
SEQUENCE: 24
ATSDILTGYY RDYYGLDV                                                   18

SEQ ID NO: 25          moltype = DNA   length = 336
FEATURE                Location/Qualifiers
misc_feature           1..336
```

```
                       note = Synthetic
source                 1..336
                       mol_type = other DNA
                       organism = synthetic construct
SEQUENCE: 25
gatattgtga tgactcagtc tccactcttc ctgcccgtca ccctggaga gccggcctcc    60
atctcctgca ggtctagtca gagcctcctg catagtaaag gatacaacta tttggattgg  120
tacctgcaga agccagggca gtctccacaa ctcctgatct atttgggttc taatcgggcc  180
tccgggggtcc ctgacaggtt cagtggcagt ggatcaggca cagattttac actgaaaatc 240
agcagagtgg aggctgaaga tgttggggtt tattactgca tgcaaactct acaaactcct  300
cggacgttcg gccaagggac caaggtggaa atcaaa                            336

SEQ ID NO: 26          moltype = AA   length = 112
FEATURE                Location/Qualifiers
REGION                 1..112
                       note = Synthetic
source                 1..112
                       mol_type = protein
                       organism = synthetic construct
SEQUENCE: 26
DIVMTQSPLF LPVTPGEPAS ISCRSSQSLL HSKGYNYLDW YLQKPGQSPQ LLIYLGSNRA   60
SGVPDRFSGS GSGTDFTLKI SRVEAEDVGV YYCMQTLQTP RTFGQGTKVE IK          112

SEQ ID NO: 27          moltype = DNA   length = 33
FEATURE                Location/Qualifiers
misc_feature           1..33
                       note = Synthetic
source                 1..33
                       mol_type = other DNA
                       organism = synthetic construct
SEQUENCE: 27
cagagcctcc tgcatagtaa aggatacaac tat                               33

SEQ ID NO: 28          moltype = AA   length = 11
FEATURE                Location/Qualifiers
REGION                 1..11
                       note = Synthetic
source                 1..11
                       mol_type = protein
                       organism = synthetic construct
SEQUENCE: 28
QSLLHSKGYN Y                                                       11

SEQ ID NO: 29          moltype =   length =
SEQUENCE: 29
000

SEQ ID NO: 30          moltype =   length =
SEQUENCE: 30
000

SEQ ID NO: 31          moltype = DNA   length = 27
FEATURE                Location/Qualifiers
misc_feature           1..27
                       note = Synthetic
source                 1..27
                       mol_type = other DNA
                       organism = synthetic construct
SEQUENCE: 31
atgcaaactc tacaaactcc tcggacg                                      27

SEQ ID NO: 32          moltype = AA   length = 9
FEATURE                Location/Qualifiers
REGION                 1..9
                       note = Synthetic
source                 1..9
                       mol_type = protein
                       organism = synthetic construct
SEQUENCE: 32
MQTLQTPRT                                                          9

SEQ ID NO: 33          moltype = DNA   length = 372
FEATURE                Location/Qualifiers
misc_feature           1..372
                       note = Synthetic
source                 1..372
                       mol_type = other DNA
                       organism = synthetic construct
SEQUENCE: 33
```

```
gaggagcaac tggtggagtc tgggggagac ttggtacagc ctggagggtc cctaagactc    60
tcctgtgcag cctctggatt cactctcagt agttatgaaa tgaactgggt ccgccaggct   120
ccagggaagg gctggagtg ggtttcatac attagtagag gtggtagtct gatacactac   180
acagactctg tgaagggccg attcaccatc tccagagaca cgccaagaa ttcactgtat   240
ctgcaaatga acagcctgag agccgaggac acggctgttt attactgtgt gagagaccca   300
gcagctcgtt atcattatta ttatcacggt atggacgtct ggggccaagg gaccacggtc   360
accgtctcct ca                                                       372

SEQ ID NO: 34              moltype = AA  length = 124
FEATURE                    Location/Qualifiers
REGION                     1..124
                           note = Synthetic
source                     1..124
                           mol_type = protein
                           organism = synthetic construct
SEQUENCE: 34
EEQLVESGGD LVQPGGSLRL SCAASGFTLS SYEMNWVRQA PGKGLEWVSY ISRGGSLIHY    60
TDSVKGRFTI SRDNAKNSLY LQMNSLRAED TAVYYCVRDP AARYHYYYHG MDVWGQGTTV   120
TVSS                                                                124

SEQ ID NO: 35              moltype = DNA  length = 24
FEATURE                    Location/Qualifiers
misc_feature               1..24
                           note = Synthetic
source                     1..24
                           mol_type = other DNA
                           organism = synthetic construct
SEQUENCE: 35
ggattcactc tcagtagtta tgaa                                           24

SEQ ID NO: 36              moltype = AA  length = 8
FEATURE                    Location/Qualifiers
REGION                     1..8
                           note = Synthetic
source                     1..8
                           mol_type = protein
                           organism = synthetic construct
SEQUENCE: 36
GFTLSSYE                                                             8

SEQ ID NO: 37              moltype = DNA  length = 24
FEATURE                    Location/Qualifiers
misc_feature               1..24
                           note = Synthetic
source                     1..24
                           mol_type = other DNA
                           organism = synthetic construct
SEQUENCE: 37
attagtagag gtggtagtct gata                                           24

SEQ ID NO: 38              moltype = AA  length = 8
FEATURE                    Location/Qualifiers
REGION                     1..8
                           note = Synthetic
source                     1..8
                           mol_type = protein
                           organism = synthetic construct
SEQUENCE: 38
ISRGGSLI                                                             8

SEQ ID NO: 39              moltype = DNA  length = 51
FEATURE                    Location/Qualifiers
misc_feature               1..51
                           note = Synthetic
source                     1..51
                           mol_type = other DNA
                           organism = synthetic construct
SEQUENCE: 39
gtgagagacc cagcagctcg ttatcattat tattatcacg gtatggacgt c             51

SEQ ID NO: 40              moltype = AA  length = 17
FEATURE                    Location/Qualifiers
REGION                     1..17
                           note = Synthetic
source                     1..17
                           mol_type = protein
                           organism = synthetic construct
SEQUENCE: 40
VRDPAARYHY YYHGMDV                                                   17
```

```
SEQ ID NO: 41          moltype = DNA   length = 336
FEATURE                Location/Qualifiers
misc_feature           1..336
                       note = Synthetic
source                 1..336
                       mol_type = other DNA
                       organism = synthetic construct
SEQUENCE: 41
gatattgtga tgactcagtc tccactctcc ctgcccgtca cccctggaga gccggcctcc    60
atctcctgca ggtctagtca gagcctcctg cacaataatg gatataacta tttggattgg   120
tatctgcaga agccagggca gtctccacag ctcctgatct atttgggttc tagtcgggcc   180
tccgggggtcc ctgacaggtt cagtggcagt ggatcaggca cagatttat actgaaaatc   240
agcagagtgg aggctgaaga tgttggggtt tattactgca tgcaagctct acaaactccg   300
tggacgttcg gccagggac caaggtggaa atcaaa                              336

SEQ ID NO: 42          moltype = AA    length = 112
FEATURE                Location/Qualifiers
REGION                 1..112
                       note = Synthetic
source                 1..112
                       mol_type = protein
                       organism = synthetic construct
SEQUENCE: 42
DIVMTQSPLS LPVTPGEPAS ISCRSSQSLL HNNGYNYLDW YLQKPGQSPQ LLIYLGSSRA    60
SGVPDRFSGS GSGTDFILKI SRVEAEDVGV YYCMQALQTP WTFGRGTKVE IK           112

SEQ ID NO: 43          moltype = DNA   length = 33
FEATURE                Location/Qualifiers
misc_feature           1..33
                       note = Synthetic
source                 1..33
                       mol_type = other DNA
                       organism = synthetic construct
SEQUENCE: 43
cagagcctcc tgcacaataa tggatataac tat                                 33

SEQ ID NO: 44          moltype = AA    length = 11
FEATURE                Location/Qualifiers
REGION                 1..11
                       note = Synthetic
source                 1..11
                       mol_type = protein
                       organism = synthetic construct
SEQUENCE: 44
QSLLHNNGYN Y                                                         11

SEQ ID NO: 45          moltype =   length =
SEQUENCE: 45
000

SEQ ID NO: 46          moltype =   length =
SEQUENCE: 46
000

SEQ ID NO: 47          moltype = DNA   length = 27
FEATURE                Location/Qualifiers
misc_feature           1..27
                       note = Synthetic
source                 1..27
                       mol_type = other DNA
                       organism = synthetic construct
SEQUENCE: 47
atgcaagctc tacaaactcc gtggacg                                        27

SEQ ID NO: 48          moltype = AA    length = 9
FEATURE                Location/Qualifiers
REGION                 1..9
                       note = Synthetic
source                 1..9
                       mol_type = protein
                       organism = synthetic construct
SEQUENCE: 48
MQALQTPWT                                                             9

SEQ ID NO: 49          moltype = DNA   length = 384
FEATURE                Location/Qualifiers
misc_feature           1..384
                       note = Synthetic
```

```
source                    1..384
                          mol_type = other DNA
                          organism = synthetic construct
SEQUENCE: 49
gaggtgcagc tggtggagtc tgggggaggc gtggtccagc ctggagggtc cctgagactc    60
tcctgtgcag cctctggatt caccttcagt agttatgaca tgcactgggt ccgccaggct   120
ccaggcaagg ggctggagtg ggtggcagtt atatcatctg atggacgtga taaatactat   180
gtagactccg tgaagggccg attcaccatc tccagagaca actccaagaa cacgctttat   240
ctgcaaatga acagcctgag agctgaggac acggctgttt attactgtgc gaaagagatg   300
gtgtattacg atatttttgac tggttatcat aactactacg gtatggacgt ctggggccaa   360
gggaccacgg tcaccgtctc ctca                                          384

SEQ ID NO: 50             moltype = AA  length = 128
FEATURE                   Location/Qualifiers
REGION                    1..128
                          note = Synthetic
source                    1..128
                          mol_type = protein
                          organism = synthetic construct
SEQUENCE: 50
EVQLVESGGG VVQPGRSLRL SCAASGFTFS SYDMHWVRQA PGKGLEWVAV ISSDGRDKYY    60
VDSVKGRFTI SRDNSKNTLY LQMNSLRAED TAVYYCAKEM VYYDILTGYH NYYGMDVWGQ   120
GTTVTVSS                                                            128

SEQ ID NO: 51             moltype = DNA  length = 24
FEATURE                   Location/Qualifiers
misc_feature              1..24
                          note = Synthetic
source                    1..24
                          mol_type = other DNA
                          organism = synthetic construct
SEQUENCE: 51
ggattcacct tcagtagtta tgac                                           24

SEQ ID NO: 52             moltype = AA  length = 8
FEATURE                   Location/Qualifiers
REGION                    1..8
                          note = Synthetic
source                    1..8
                          mol_type = protein
                          organism = synthetic construct
SEQUENCE: 52
GFTFSSYD                                                              8

SEQ ID NO: 53             moltype = DNA  length = 24
FEATURE                   Location/Qualifiers
misc_feature              1..24
                          note = Synthetic
source                    1..24
                          mol_type = other DNA
                          organism = synthetic construct
SEQUENCE: 53
atatcatctg atggacgtga taaa                                           24

SEQ ID NO: 54             moltype = AA  length = 8
FEATURE                   Location/Qualifiers
REGION                    1..8
                          note = Synthetic
source                    1..8
                          mol_type = protein
                          organism = synthetic construct
SEQUENCE: 54
ISSDGRDK                                                              8

SEQ ID NO: 55             moltype = DNA  length = 63
FEATURE                   Location/Qualifiers
misc_feature              1..63
                          note = Synthetic
source                    1..63
                          mol_type = other DNA
                          organism = synthetic construct
SEQUENCE: 55
gcgaaagaga tggtgtatta cgatatttttg actggttatc ataactacta cggtatggac   60
gtc                                                                  63

SEQ ID NO: 56             moltype = AA  length = 21
FEATURE                   Location/Qualifiers
REGION                    1..21
                          note = Synthetic
```

```
source                  1..21
                        mol_type = protein
                        organism = synthetic construct
SEQUENCE: 56
AKEMVYYDIL TGYHNYYGMD V                                                 21

SEQ ID NO: 57           moltype = DNA   length = 324
FEATURE                 Location/Qualifiers
misc_feature            1..324
                        note = Synthetic
source                  1..324
                        mol_type = other DNA
                        organism = synthetic construct
SEQUENCE: 57
gacatcgtga tgacccagtc tccatcctca ctgtctgcat ctgtaggaga cagagtcacc        60
atcacttgtc gggcgagtca gggcattaac aattatttag cctggtttca gcagaaacca      120
gggaaagccc ctaagtccct gatccatact gcatccagtt tgcaaagtgg ggtcccatca      180
aagttcagcg gcagtggatc tgggacagat ttcactctca ccatcagcag cctgcagcct      240
gaagattttg caacttatta ctgccaacag tataatactt accctctcac tttcggcgga      300
gggaccaaag tggagatcaa acga                                             324

SEQ ID NO: 58           moltype = AA   length = 108
FEATURE                 Location/Qualifiers
REGION                  1..108
                        note = Synthetic
source                  1..108
                        mol_type = protein
                        organism = synthetic construct
SEQUENCE: 58
DIVMTQSPSS LSASVGDRVT ITCRASQGIN NYLAWFQQKP GKAPKSLIHT ASSLQSGVPS        60
KFSGSGSGTD FTLTISSLQP EDFATYYCQQ YNTYPLTFGG GTKVEIKR                   108

SEQ ID NO: 59           moltype = DNA   length = 18
FEATURE                 Location/Qualifiers
misc_feature            1..18
                        note = Synthetic
source                  1..18
                        mol_type = other DNA
                        organism = synthetic construct
SEQUENCE: 59
cagggcatta acaattat                                                     18

SEQ ID NO: 60           moltype = AA   length = 6
FEATURE                 Location/Qualifiers
REGION                  1..6
                        note = Synthetic
source                  1..6
                        mol_type = protein
                        organism = synthetic construct
SEQUENCE: 60
QGINNY                                                                   6

SEQ ID NO: 61           moltype =   length =
SEQUENCE: 61
000

SEQ ID NO: 62           moltype =   length =
SEQUENCE: 62
000

SEQ ID NO: 63           moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 63
caacagtata atacttaccc tctcact                                           27

SEQ ID NO: 64           moltype = AA   length = 9
FEATURE                 Location/Qualifiers
REGION                  1..9
                        note = Synthetic
source                  1..9
                        mol_type = protein
                        organism = synthetic construct
SEQUENCE: 64
QQYNTYPLT                                                                9
```

```
SEQ ID NO: 65              moltype = DNA  length = 381
FEATURE                    Location/Qualifiers
misc_feature               1..381
                           note = Synthetic
source                     1..381
                           mol_type = other DNA
                           organism = synthetic construct
SEQUENCE: 65
caggtgcagc tggtggagtc tgggggaggc gtggtccagc ctggggggtc cctgagactc    60
tcctgtgcag cctctggatt caccttcagt agttatgaca tgcactggg  ccgccaggct   120
ccaggcaagg ggctggagtg ggtggcagtt atatcatctg atggacgtga taatactat    180
gtagactccg tgaagggccg attcaccatc tccagagaca actccaagaa cacgctttat   240
ctgcaaatga acagcctgag agctgaggac acggctgttt attactgtgc gaaagagatg   300
gtgtattacg atattttgac tggttatcat aactactacg tatggacgt  ctggggccaa   360
gggaccacgg tcaccgtctc c                                             381

SEQ ID NO: 66              moltype = AA  length = 127
FEATURE                    Location/Qualifiers
REGION                     1..127
                           note = Synthetic
source                     1..127
                           mol_type = protein
                           organism = synthetic construct
SEQUENCE: 66
QVQLVESGGG VVQPGRSLRL SCAASGFTFS SYDMHWVRQA PGKGLEWVAV ISSDGRDKYY     60
VDSVKGRFTI SRDNSKNTLY LQMNSLRAED TAVYYCAKEM VYYDILTGYH NYYGMDVWGQ    120
GTTVTVS                                                              127

SEQ ID NO: 67              moltype = DNA  length = 321
FEATURE                    Location/Qualifiers
misc_feature               1..321
                           note = Synthetic
source                     1..321
                           mol_type = other DNA
                           organism = synthetic construct
SEQUENCE: 67
gacatccaga tgacccagtc tccatcctca ctgtctgcat ctgtaggaga cagagtcacc     60
atcacttgtc gggcgagtca gggcattaac aattatttag cctggtttca gcagaaacca   120
gggaaagccc ctaagtccct gatccatact gcatccagtt tgcaaagtgg ggtcccatca   180
aagttcagcg gcagtggatc tgggacagat ttcactctca ccatcagcag cctgcagcct   240
gaagattttg caacttatta ctgccaacag tataatactt accctctcac tttcggcgga   300
gggaccaagg tggagatcaa a                                             321

SEQ ID NO: 68              moltype = AA  length = 107
FEATURE                    Location/Qualifiers
REGION                     1..107
                           note = Synthetic
source                     1..107
                           mol_type = protein
                           organism = synthetic construct
SEQUENCE: 68
DIQMTQSPSS LSASVGDRVT ITCRASQGIN NYLAWFQQKP GKAPKSLIHT ASSLQSGVPS     60
KFSGSGSGTD FTLTISSLQP EDFATYYCQQ YNTYPLTFGG GTKVEIK                  107

SEQ ID NO: 69              moltype = DNA  length = 384
FEATURE                    Location/Qualifiers
misc_feature               1..384
                           note = Synthetic
source                     1..384
                           mol_type = other DNA
                           organism = synthetic construct
SEQUENCE: 69
caggtgcagc tggtgcagtc tgggggaggc ttggtccagc ctgggggtc  cctgagactc     60
tcctgtgcag cctccggatt cacctttagt aactatttga tgaactgggt ccgccaggct   120
ccagggaagg ggctggagtg gctggccaac atacaggaag atggaattga gaatactat    180
gtggactctg tgaagggccg attcaccatc tccagagaca cgccaagaa  ctcactgtat   240
ctgcaaatga acagcctgag agccgaggac acggctgtgt attactgtgc gagagagccc   300
tcccattacg atattttgac tggttatgac tactattacg tatggacgt  ctggggccaa   360
gggaccacgg tcaccgtctc ctca                                          384

SEQ ID NO: 70              moltype = AA  length = 128
FEATURE                    Location/Qualifiers
REGION                     1..128
                           note = Synthetic
source                     1..128
                           mol_type = protein
                           organism = synthetic construct
SEQUENCE: 70
```

```
QVQLVQSGGG LVQPGGSLRL SCAASGFTFS NYLMNWVRQA PGKGLEWLAN IQEDGIEKYY    60
VDSVKGRFTI SRDNAKNSLY LQMNSLRAED TAVYYCAREP SHYDILTGYD YYYGMDVWGQ   120
GTTVTVSS                                                            128

SEQ ID NO: 71            moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 71
ggattcacct ttagtaacta tttg                                           24

SEQ ID NO: 72            moltype = AA  length = 8
FEATURE                  Location/Qualifiers
REGION                   1..8
                         note = Synthetic
source                   1..8
                         mol_type = protein
                         organism = synthetic construct
SEQUENCE: 72
GFTFSNYL                                                              8

SEQ ID NO: 73            moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 73
atacaggaag atggaattga gaaa                                           24

SEQ ID NO: 74            moltype = AA  length = 8
FEATURE                  Location/Qualifiers
REGION                   1..8
                         note = Synthetic
source                   1..8
                         mol_type = protein
                         organism = synthetic construct
SEQUENCE: 74
IQEDGIEK                                                              8

SEQ ID NO: 75            moltype = DNA  length = 63
FEATURE                  Location/Qualifiers
misc_feature             1..63
                         note = Synthetic
source                   1..63
                         mol_type = other DNA
                         organism = synthetic construct
SEQUENCE: 75
gcgagagagc cctcccatta cgatattttg actggttatg actactatta cggtatggac    60
gtc                                                                  63

SEQ ID NO: 76            moltype = AA  length = 21
FEATURE                  Location/Qualifiers
REGION                   1..21
                         note = Synthetic
source                   1..21
                         mol_type = protein
                         organism = synthetic construct
SEQUENCE: 76
AREPSHYDIL TGYDYYYGMD V                                              21

SEQ ID NO: 77            moltype = DNA  length = 324
FEATURE                  Location/Qualifiers
misc_feature             1..324
                         note = Synthetic
source                   1..324
                         mol_type = other DNA
                         organism = synthetic construct
SEQUENCE: 77
gacatccagt tgacccagtc tccatcctcc ctgtctgcat ctgtaggaga cagagtcacc    60
atcacttgcc gggcaagtca gggcattaga aatgatttag ctggtatca gcagaaacca   120
gggaaagccc ctaagcgcct gatctatgct gcatccagtt tgcaaagtgg ggtcccatca   180
aggttcagcg gcagtggatc tgggacagaa ttcattctca cagtcagcag cctgcagcct   240
gaagactttg caacttatta ctgtctacag tataatagta acccattcac tttcggccct   300
gggaccaagg tggagatcaa acga                                          324
```

```
SEQ ID NO: 78            moltype = AA  length = 108
FEATURE                  Location/Qualifiers
REGION                   1..108
                         note = Synthetic
source                   1..108
                         mol_type = protein
                         organism = synthetic construct
SEQUENCE: 78
DIQLTQSPSS LSASVGDRVT ITCRASQGIR NDLGWYQQKP GKAPKRLIYA ASSLQSGVPS    60
RFSGSGSGTE FILTVSSLQP EDFATYYCLQ YNSNPFTFGP GTKVEIKR                108

SEQ ID NO: 79            moltype = DNA  length = 18
FEATURE                  Location/Qualifiers
misc_feature             1..18
                         note = Synthetic
source                   1..18
                         mol_type = other DNA
                         organism = synthetic construct
SEQUENCE: 79
cagggcatta gaaatgat                                                  18

SEQ ID NO: 80            moltype = AA  length = 6
FEATURE                  Location/Qualifiers
REGION                   1..6
                         note = Synthetic
source                   1..6
                         mol_type = protein
                         organism = synthetic construct
SEQUENCE: 80
QGIRND                                                               6

SEQ ID NO: 81            moltype =    length =
SEQUENCE: 81
000

SEQ ID NO: 82            moltype =    length =
SEQUENCE: 82
000

SEQ ID NO: 83            moltype = DNA  length = 27
FEATURE                  Location/Qualifiers
misc_feature             1..27
                         note = Synthetic
source                   1..27
                         mol_type = other DNA
                         organism = synthetic construct
SEQUENCE: 83
ctacagtata atagtaaccc attcact                                        27

SEQ ID NO: 84            moltype = AA  length = 9
FEATURE                  Location/Qualifiers
REGION                   1..9
                         note = Synthetic
source                   1..9
                         mol_type = protein
                         organism = synthetic construct
SEQUENCE: 84
LQYNSNPFT                                                            9

SEQ ID NO: 85            moltype = DNA  length = 381
FEATURE                  Location/Qualifiers
misc_feature             1..381
                         note = Synthetic
source                   1..381
                         mol_type = other DNA
                         organism = synthetic construct
SEQUENCE: 85
gaggtgcagc tggtggagtc tgggggaggc ttggtccagc ctggggggtc cctgagactc    60
tcctgtgcag cctccggatt cacctttagt aactatttga tgaactgggt ccgccaggct   120
ccagggaagg ggctggagtg gctggccaac atacaggaag atggaattga gaaatactat   180
gtggactctg tgaagggccg attcaccatc tccagagaca cgccaagaa ctcactgtat    240
ctgcaaatga acagcctgag agccgaggac acggctgtgt attactgtgc gagagagccc   300
tcccattacg atattttgac tggttatgac tactattacg gtatggacgt ctggggccaa   360
gggaccacgg tcaccgtctc c                                             381

SEQ ID NO: 86            moltype = AA  length = 127
FEATURE                  Location/Qualifiers
REGION                   1..127
```

```
                        note = Synthetic
source                  1..127
                        mol_type = protein
                        organism = synthetic construct
SEQUENCE: 86
EVQLVESGGG LVQPGGSLRL SCAASGFTFS NYLMNWVRQA PGKGLEWLAN IQEDGIEKYY    60
VDSVKGRFTI SRDNAKNSLY LQMNSLRAED TAVYYCAREP SHYDILTGYD YYYGMDVWGQ   120
GTTVTVS                                                             127

SEQ ID NO: 87           moltype = DNA   length = 321
FEATURE                 Location/Qualifiers
misc_feature            1..321
                        note = Synthetic
source                  1..321
                        mol_type = other DNA
                        organism = synthetic construct
SEQUENCE: 87
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcattctca cagtcagcag cctgcagcct   240
gaagactttg caacttatta ctgtctacag tataatagta cccattcac tttcggccct   300
gggaccaaag tggatatcaa a                                             321

SEQ ID NO: 88           moltype = AA   length = 107
FEATURE                 Location/Qualifiers
REGION                  1..107
                        note = Synthetic
source                  1..107
                        mol_type = protein
                        organism = synthetic construct
SEQUENCE: 88
DIQMTQSPSS LSASVGDRVT ITCRASQGIR NDLGWYQQKP GKAPKRLIYA ASSLQSGVPS    60
RFSGSGSGTE FILTVSSLQP EDFATYYCLQ YNSNPFTFGP GTKVDIK                 107

SEQ ID NO: 89           moltype = DNA   length = 381
FEATURE                 Location/Qualifiers
misc_feature            1..381
                        note = Synthetic
source                  1..381
                        mol_type = other DNA
                        organism = synthetic construct
SEQUENCE: 89
gaggtgcagc tggtgcagtc tgggggagcc ttggtacagc ctggggggtc cctgagactc    60
tcctgtacag cctctggttt caccttcagt aactacgaca tgcactgggt ccgccaaact   120
acaggaaaag gtctggagtg gatctcagct attgatactg ctggtgacac atactatcca   180
ggctccgtga agggccgatt caccgtctcc agagaaaatg ccaagaactc cttttatctt   240
caaatgaaca gcctgagagc cggggacacg gctgtgtatt actgtgcaag ggaggggaag   300
tattacgata ttttgactgg tgactaccac tactacggta tggacgtctg gggccaaggg   360
accacggtca ccgtctcctc a                                             381

SEQ ID NO: 90           moltype = AA   length = 127
FEATURE                 Location/Qualifiers
REGION                  1..127
                        note = Synthetic
source                  1..127
                        mol_type = protein
                        organism = synthetic construct
SEQUENCE: 90
EVQLVQSGGA LVQPGGSLRL SCTASGFTFS NYDMHWVRQT TGKGLEWISA IDTAGDTYYP    60
GSVKGRFTVS RENAKNSFYL QMNSLRAGDT AVYYCAREGK YYDILTGDYH YYGMDVWGQG   120
TTVTVSS                                                             127

SEQ ID NO: 91           moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 91
ggtttcacct tcagtaacta cgac                                           24

SEQ ID NO: 92           moltype = AA   length = 8
FEATURE                 Location/Qualifiers
REGION                  1..8
                        note = Synthetic
source                  1..8
                        mol_type = protein
```

```
                         organism = synthetic construct
SEQUENCE: 92
GFTFSNYD                                                                        8

SEQ ID NO: 93            moltype = DNA  length = 21
FEATURE                  Location/Qualifiers
misc_feature             1..21
                         note = Synthetic
source                   1..21
                         mol_type = other DNA
                         organism = synthetic construct
SEQUENCE: 93
attgatactg ctggtgacac a                                                        21

SEQ ID NO: 94            moltype = AA  length = 7
FEATURE                  Location/Qualifiers
REGION                   1..7
                         note = Synthetic
source                   1..7
                         mol_type = protein
                         organism = synthetic construct
SEQUENCE: 94
IDTAGDT                                                                         7

SEQ ID NO: 95            moltype = DNA  length = 63
FEATURE                  Location/Qualifiers
misc_feature             1..63
                         note = Synthetic
source                   1..63
                         mol_type = other DNA
                         organism = synthetic construct
SEQUENCE: 95
gcaagggagg ggaagtatta cgatattttg actggtgact accactacta cggtatggac             60
gtc                                                                            63

SEQ ID NO: 96            moltype = AA  length = 21
FEATURE                  Location/Qualifiers
REGION                   1..21
                         note = Synthetic
source                   1..21
                         mol_type = protein
                         organism = synthetic construct
SEQUENCE: 96
AREGKYYDIL TGDYHYYGMD V                                                        21

SEQ ID NO: 97            moltype = DNA  length = 324
FEATURE                  Location/Qualifiers
misc_feature             1..324
                         note = Synthetic
source                   1..324
                         mol_type = other DNA
                         organism = synthetic construct
SEQUENCE: 97
gccatccgga tgacccagtc tccatcctcc ctgtctgcat ctgtaggaga cagagtcacc             60
atcacttgtc gggcaagtca gggcattaga aatgatttga gctggtatca gcagaaacca            120
gggaaagccc ctaagcgact gatctatgct acatccagtt tgcaaagtgg ggtcccatca            180
aggttcagcg gcagtggatc tgggacagaa ttcactctca caatcagcag cctgcagcct            240
gaagattttg caacttatta ctgtctacag cataatagtt acccgctcac tttcggcgga            300
gggaccaagg tggaaatcaa acga                                                   324

SEQ ID NO: 98            moltype = AA  length = 108
FEATURE                  Location/Qualifiers
REGION                   1..108
                         note = Synthetic
source                   1..108
                         mol_type = protein
                         organism = synthetic construct
SEQUENCE: 98
AIRMTQSPSS LSASVGDRVT ITCRASQGIR NDLGWYQQKP GKAPKRLIYA TSSLQSGVPS             60
RFSGSGSGTE FTLTISSLQP EDFATYYCLQ HNSYPLTFGG GTKVEIKR                         108

SEQ ID NO: 99            moltype = DNA  length = 18
FEATURE                  Location/Qualifiers
misc_feature             1..18
                         note = Synthetic
source                   1..18
                         mol_type = other DNA
                         organism = synthetic construct
SEQUENCE: 99
```

```
cagggcatta gaaatgat                                                       18

SEQ ID NO: 100          moltype = AA   length = 6
FEATURE                 Location/Qualifiers
REGION                  1..6
                        note = Synthetic
source                  1..6
                        mol_type = protein
                        organism = synthetic construct
SEQUENCE: 100
QGIRND                                                                     6

SEQ ID NO: 101          moltype =     length =
SEQUENCE: 101
000

SEQ ID NO: 102          moltype =     length =
SEQUENCE: 102
000

SEQ ID NO: 103          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 103
ctacagcata atagttaccc gctcact                                             27

SEQ ID NO: 104          moltype = AA   length = 9
FEATURE                 Location/Qualifiers
REGION                  1..9
                        note = Synthetic
source                  1..9
                        mol_type = protein
                        organism = synthetic construct
SEQUENCE: 104
LQHNSYPLT                                                                  9

SEQ ID NO: 105          moltype = DNA   length = 378
FEATURE                 Location/Qualifiers
misc_feature            1..378
                        note = Synthetic
source                  1..378
                        mol_type = other DNA
                        organism = synthetic construct
SEQUENCE: 105
gaggtgcagc tggtggagtc tgggggagcc ttggtacagc ctgggggtc cctgagactc          60
tcctgtacag cctctggttt caccttcagt aactacgaca tgcactgggt ccgccaaact        120
acaggaaaag gtctggagtg gatctcagct attgatacta ctggtgacac atactatcca        180
ggctccgtga agggccgatt caccgtctcc agagaaaatg ccaagaactc ctttatctt         240
caaatgaaca gcctgagagc cggggacacg gctgtgtatt actgtgcaag ggaggggaag        300
tattacgata ttttgactgg tgactaccac tactacggta tggacgtctg gggccaaggg        360
accacggtca ccgtctcc                                                      378

SEQ ID NO: 106          moltype = AA   length = 126
FEATURE                 Location/Qualifiers
REGION                  1..126
                        note = Synthetic
source                  1..126
                        mol_type = protein
                        organism = synthetic construct
SEQUENCE: 106
EVQLVESGGA LVQPGGSLRL SCTASGFTFS NYDMHWVRQT TGKGLEWISA IDTAGDTYYP          60
GSVKGRFTVS RENAKNSFYL QMNSLRAGDT AVYYCAREGK YYDILTGDYH YYGMDVWGQG        120
TTVTVS                                                                   126

SEQ ID NO: 107          moltype = DNA   length = 321
FEATURE                 Location/Qualifiers
misc_feature            1..321
                        note = Synthetic
source                  1..321
                        mol_type = other DNA
                        organism = synthetic construct
SEQUENCE: 107
gacatccaga tgacccagtc tccatcctcc ctgtctgcat ctgtaggaga cagagtcacc          60
atcacttgtc gggcaagtca gggcattaga aatgatttag ctggtatca gcagaaacca        120
gggaaagccc ctaagcgact gatctatgct acatccagtt tgcaaagtgg ggtcccatca        180
```

```
aggttcagcg gcagtggatc tgggacagaa ttcactctca caatcagcag cctgcagcct    240
gaagattttg caacttatta ctgtctacag cataatagtt acccgctcac tttcggcgga    300
gggaccaagc tggagatcaa a                                              321

SEQ ID NO: 108          moltype = AA   length = 107
FEATURE                 Location/Qualifiers
REGION                  1..107
                        note = Synthetic
source                  1..107
                        mol_type = protein
                        organism = synthetic construct
SEQUENCE: 108
DIQMTQSPSS LSASVGDRVT ITCRASQGIR NDLGWYQQKP GKAPKRLIYA TSSLQSGVPS     60
RFSGSGSGTE FTLTISSLQP EDFATYYCLQ HNSYPLTFGG GTKLEIK                  107

SEQ ID NO: 109          moltype = DNA   length = 372
FEATURE                 Location/Qualifiers
misc_feature            1..372
                        note = Synthetic
source                  1..372
                        mol_type = other DNA
                        organism = synthetic construct
SEQUENCE: 109
caggtgcagc tggtgcagtc tggggaggc gtggtccagc ctggggaggtc cctgagactc     60
tcctgtgcag cgtctgggtt cacctttagt aactttggca tgcactgggt ccgccaggct    120
ccaggcaagg ggctggagtg ggtggcagtt atatggtttg atgaaattga taaatactat    180
gcagactccg tgaagggccg attcaccatc tccagagaca attccaagaa cacgctgtat    240
ccgcaaatga acagcctgag agccgaagac acggctgtgt attactgtgc gcgagaagat    300
tacgatattt tgactggtta ctattacgct atggacgtct ggggccaagg gaccacggtc    360
accgtctcct ca                                                        372

SEQ ID NO: 110          moltype = AA   length = 124
FEATURE                 Location/Qualifiers
REGION                  1..124
                        note = Synthetic
source                  1..124
                        mol_type = protein
                        organism = synthetic construct
SEQUENCE: 110
QVQLVQSGGG VVQPGRSLRL SCAASGFTFS NFGMHWVRQA PGKGLEWVAV IWFDEIDKYY     60
ADSVKGRFTI SRDNSKNTLY PQMNSLRAED TAVYYCARED YDILTGYYYA MDVWGQGTTV    120
TVSS                                                                 124

SEQ ID NO: 111          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 111
gggttcacct ttagtaactt tggc                                            24

SEQ ID NO: 112          moltype = AA   length = 8
FEATURE                 Location/Qualifiers
REGION                  1..8
                        note = Synthetic
source                  1..8
                        mol_type = protein
                        organism = synthetic construct
SEQUENCE: 112
GFTFSNFG                                                               8

SEQ ID NO: 113          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 113
atatggtttg atgaaattga taaa                                            24

SEQ ID NO: 114          moltype = AA   length = 8
FEATURE                 Location/Qualifiers
REGION                  1..8
                        note = Synthetic
source                  1..8
                        mol_type = protein
```

```
                        organism = synthetic construct
SEQUENCE: 114
IWFDEIDK                                                                   8

SEQ ID NO: 115          moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 115
gcgcgagaag attacgatat tttgactggt tactattacg ctatggacgt c                  51

SEQ ID NO: 116          moltype = AA  length = 17
FEATURE                 Location/Qualifiers
REGION                  1..17
                        note = Synthetic
source                  1..17
                        mol_type = protein
                        organism = synthetic construct
SEQUENCE: 116
AREDYDILTG YYYAMDV                                                        17

SEQ ID NO: 117          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 117
gacatccaga tgacccagtc tccatcctcc ctgtctgcat ctgtaggaga cagagtcacc         60
atcacttgcc gggcaagtca gggcattaga aatgatttag gctggtatca gcagaaacca       120
gggaaagccc ctaagcgcct aatctatgct gcatcccgtt tgcaaagtgg ggtcccatcg       180
aggttcagcg gcagtggatc tgggacagaa ttcactctca caatcagcag cctgcagcct       240
gaagattttg gaacttatta ctgtctacag cataatagtc accccacctt cggccaaggg       300
accaaggtgg agatcaaacg a                                                 321

SEQ ID NO: 118          moltype = AA  length = 107
FEATURE                 Location/Qualifiers
REGION                  1..107
                        note = Synthetic
source                  1..107
                        mol_type = protein
                        organism = synthetic construct
SEQUENCE: 118
DIQMTQSPSS LSASVGDRVT ITCRASQGIR NDLGWYQQKP GKAPKRLIYA ASRLQSGVPS         60
RFSGSGSGTE FTLTISSLQP EDFGTYYCLQ HNSHPTFGQG TKVEIKR                     107

SEQ ID NO: 119          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 119
cagggcatta gaaatgat                                                       18

SEQ ID NO: 120          moltype = AA  length = 6
FEATURE                 Location/Qualifiers
REGION                  1..6
                        note = Synthetic
source                  1..6
                        mol_type = protein
                        organism = synthetic construct
SEQUENCE: 120
QGIRND                                                                     6

SEQ ID NO: 121          moltype =   length =
SEQUENCE: 121
000

SEQ ID NO: 122          moltype =   length =
SEQUENCE: 122
000

SEQ ID NO: 123          moltype = DNA  length = 24
```

```
FEATURE                 Location/Qualifiers
misc_feature            1..24
                        note = Synthetic
source                  1..24
                        mol_type = other DNA
                        organism = synthetic construct
SEQUENCE: 123
ctacagcata atagtcaccc cacc                                              24

SEQ ID NO: 124          moltype = AA   length = 8
FEATURE                 Location/Qualifiers
REGION                  1..8
                        note = Synthetic
source                  1..8
                        mol_type = protein
                        organism = synthetic construct
SEQUENCE: 124
LQHNSHPT                                                                8

SEQ ID NO: 125          moltype = DNA   length = 369
FEATURE                 Location/Qualifiers
misc_feature            1..369
                        note = Synthetic
source                  1..369
                        mol_type = other DNA
                        organism = synthetic construct
SEQUENCE: 125
caggtgcagc tggtggagtc tgggggaggc gtggtccagc ctgggaggtc cctgagactc        60
tcctgtgcag cgtctgggtt cacctttagt aactttggca tgcactgggt ccgccaggct      120
ccaggcaagg ggctggagtg ggtggcagtt atatggtttg atgaaattga taaatactat      180
gcagactccg tgaagggccg attcaccatc tccagagaca attccaagaa cacgctgtat      240
ccgcaaatga acagcctgag agccgaagac acggctgtgt attactgtgc gcgagaagat      300
tacgatattt tgactggtta ctattacgct atggacgtct ggggccaagg gaccacggtc      360
accgtctcc                                                              369

SEQ ID NO: 126          moltype = AA   length = 123
FEATURE                 Location/Qualifiers
REGION                  1..123
                        note = Synthetic
source                  1..123
                        mol_type = protein
                        organism = synthetic construct
SEQUENCE: 126
QVQLVESGGG VVQPGRSLRL SCAASGFTFS NFGMHWVRQA PGKGLEWVAV IWFDEIDKYY        60
ADSVKGRFTI SRDNSKNTLY PQMNSLRAED TAVYYCARED YDILTGYYYA MDVWGQGTTV      120
TVS                                                                    123

SEQ ID NO: 127          moltype = DNA   length = 318
FEATURE                 Location/Qualifiers
misc_feature            1..318
                        note = Synthetic
source                  1..318
                        mol_type = other DNA
                        organism = synthetic construct
SEQUENCE: 127
gacatccaga tgacccagtc tccatcctcc ctgtctgcat ctgtaggaga cagagtcacc        60
atcacttgcc gggcaagtca gggcattaga aatgatttag ctggtatca gcagaaacca      120
gggaaagccc ctaagcgcct aatctatgct gcatcccgtt tgcaaagtgg ggtcccatcg      180
aggttcagcg gcagtggatc tgggacagaa ttcactctca caatcagcag cctgcagcct      240
gaagattttg aacttatta ctgtctacag cataatagtc accccacctt cggccaaggg      300
accaaggtgg agatcaaa                                                    318

SEQ ID NO: 128          moltype = AA   length = 106
FEATURE                 Location/Qualifiers
REGION                  1..106
                        note = Synthetic
source                  1..106
                        mol_type = protein
                        organism = synthetic construct
SEQUENCE: 128
DIQMTQSPSS LSASVGDRVT ITCRASQGIK NDLGWYQQKP GKAPKRLIYA ASRLQSGVPS        60
RFSGSGSGTE FTLTISSLQP EDFGTYYCLQ HNSHPTFGQG TKVEIK                     106

SEQ ID NO: 129          moltype = DNA   length = 381
FEATURE                 Location/Qualifiers
misc_feature            1..381
                        note = Synthetic
source                  1..381
                        mol_type = other DNA
```

```
                    organism = synthetic construct
SEQUENCE: 129
gaggtgcagc tggtggagtc gggggaggc atggtacagc ctgggggtc cctgagactc        60
tcctgtgcag cctctggatt cacctccagt aactacgaca tgcactgggt ccgccaagct      120
acaggaaaag gtctggagtg gtctcaagt attgatactg ctggggacac ttactatcca       180
gactccgtga agggccgctt tatcatctcc agagaaaatg ccaaaaactc cctgtatctt      240
caaatgaata gcctgagagc cggggacacg gctgtgtatt actgtacaag ggagccccga      300
aattacgaaa ttttgactgg tcactaccac taccacggta tggacatctg gggccaaggg      360
accacggtca ccgtctcctc a                                                381

SEQ ID NO: 130           moltype = AA   length = 127
FEATURE                  Location/Qualifiers
REGION                   1..127
                         note = Synthetic
source                   1..127
                         mol_type = protein
                         organism = synthetic construct
SEQUENCE: 130
EVQLVESGGG MVQPGGSLRL SCAASGFTSS NYDMHWVRQA TGKGLEWVSS IDTAGDTYYP       60
DSVKGRFIIS RENAKNSLYL QMNSLRAGDT AVYYCTREPR NYEILTGHYH YHGMDIWGQG      120
TTVTVSS                                                                127

SEQ ID NO: 131           moltype = DNA   length = 24
FEATURE                  Location/Qualifiers
misc_feature             1..24
                         note = Synthetic
source                   1..24
                         mol_type = other DNA
                         organism = synthetic construct
SEQUENCE: 131
ggattcacct ccagtaacta cgac                                             24

SEQ ID NO: 132           moltype = AA   length = 8
FEATURE                  Location/Qualifiers
REGION                   1..8
                         note = Synthetic
source                   1..8
                         mol_type = protein
                         organism = synthetic construct
SEQUENCE: 132
GFTSSNYD                                                               8

SEQ ID NO: 133           moltype = DNA   length = 21
FEATURE                  Location/Qualifiers
misc_feature             1..21
                         note = Synthetic
source                   1..21
                         mol_type = other DNA
                         organism = synthetic construct
SEQUENCE: 133
attgatactg ctggggacac t                                                21

SEQ ID NO: 134           moltype = AA   length = 7
FEATURE                  Location/Qualifiers
REGION                   1..7
                         note = Synthetic
source                   1..7
                         mol_type = protein
                         organism = synthetic construct
SEQUENCE: 134
IDTAGDT                                                                7

SEQ ID NO: 135           moltype = DNA   length = 63
FEATURE                  Location/Qualifiers
misc_feature             1..63
                         note = Synthetic
source                   1..63
                         mol_type = other DNA
                         organism = synthetic construct
SEQUENCE: 135
acaagggagc cccgaaatta cgaaattttg actggtcact accactacca cggtatggac       60
atc                                                                    63

SEQ ID NO: 136           moltype = AA   length = 21
FEATURE                  Location/Qualifiers
REGION                   1..21
                         note = Synthetic
source                   1..21
                         mol_type = protein
```

```
                        organism = synthetic construct
SEQUENCE: 136
TREPRNYEIL TGHYHYHGMD I                                            21

SEQ ID NO: 137          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 137
gacatccaga tgacccagtc gccatcctcc ctgtctgcat ctgtaggaga cagagtcacc    60
atcacttgcc gggcaagtca ggcattaga aatgatttag gctggtatca gcagaaacca   120
gggaaagccc ctaaactcct gatctatact gcattcagtt tacagagtgg ggtcccatca   180
aggttcagcg gcagtaaatc tggcacagac ttcactctca ccatcagcag cctgcagcct   240
gaagattttg cgacttatta ctgtctgcag gattacacta tcctcggac gttcggccaa    300
gggaccaagg tggagatcaa acga                                          324

SEQ ID NO: 138          moltype = AA  length = 108
FEATURE                 Location/Qualifiers
REGION                  1..108
                        note = Synthetic
source                  1..108
                        mol_type = protein
                        organism = synthetic construct
SEQUENCE: 138
DIQMTQSPSS LSASVGDRVT ITCRASQAIR NDLGWYQQKP GKAPKLLIYT AFSLQSGVPS    60
RFSGSKSGTD FTLTISSLQP EDFATYYCLQ DYTNPRTFGQ GTKVEIKR                108

SEQ ID NO: 139          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 139
caggccatta gaaatgat                                                 18

SEQ ID NO: 140          moltype = AA  length = 6
FEATURE                 Location/Qualifiers
REGION                  1..6
                        note = Synthetic
source                  1..6
                        mol_type = protein
                        organism = synthetic construct
SEQUENCE: 140
QAIRND                                                              6

SEQ ID NO: 141          moltype =   length =
SEQUENCE: 141
000

SEQ ID NO: 142          moltype =   length =
SEQUENCE: 142
000

SEQ ID NO: 143          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 143
ctgcaggatt acactaatcc tcggacg                                       27

SEQ ID NO: 144          moltype = AA  length = 9
FEATURE                 Location/Qualifiers
REGION                  1..9
                        note = Synthetic
source                  1..9
                        mol_type = protein
                        organism = synthetic construct
SEQUENCE: 144
LQDYTNPRT                                                           9

SEQ ID NO: 145          moltype = DNA  length = 378
```

```
FEATURE                 Location/Qualifiers
misc_feature            1..378
                        note = Synthetic
source                  1..378
                        mol_type = other DNA
                        organism = synthetic construct
SEQUENCE: 145
gaggtgcagc tggtggagtc ggggggaggc atggtacagc ctgggggtc cctgagactc    60
tcctgtgcag cctctggatt cacctccagt aactacgaca tgcactgggt ccgccaagct  120
acaggaaaag gtctggagtg ggtctcaagt attgatactg gtggggacac ttactatcca  180
gactccgtga agggccgctt tatcatctcc agagaaaatg ccaaaaactc cctgtatctt  240
caaatgaata gcctgagagc cggggacacg gctgtgtatt actgtacaag ggagcccga   300
aattacgaaa ttttgactgg tcactaccac taccacggta tggacatctg gggccaaggg  360
accacggtca ccgtctcc                                                378

SEQ ID NO: 146          moltype = AA   length = 126
FEATURE                 Location/Qualifiers
REGION                  1..126
                        note = Synthetic
source                  1..126
                        mol_type = protein
                        organism = synthetic construct
SEQUENCE: 146
EVQLVESGGG MVQPGGSLRL SCAASGFTSS NYDMHWVRQA TGKGLEWVSS IDTAGDTYYP    60
DSVKGRFIIS RENAKNSLYL QMNSLRAGDT AVYYCTREPR NYEILTGHYH YHGMDIWGQG  120
TTVTVS                                                             126

SEQ ID NO: 147          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 147
gccatccaga tgacccagtc gccatcctcc ctgtctgcat ctgtaggaga cagagtcacc    60
atcacttgcc gggcaagtca ggccattaga aatgatttag ctggtatca gcagaaacca   120
gggaaagccc ctaaactcct gatctatact gcattcagtt tacagagtgg ggtcccatca  180
aggttcagcg gcagtaaatc tggcacagac ttcactctca ccatcagcag cctgcagcct  240
gaagattttg cgacttatta ctgtctgcag gattacacta atcctcggac gttcggccaa  300
gggaccaagg tggaaatcaa a                                            321

SEQ ID NO: 148          moltype = AA   length = 107
FEATURE                 Location/Qualifiers
REGION                  1..107
                        note = Synthetic
source                  1..107
                        mol_type = protein
                        organism = synthetic construct
SEQUENCE: 148
AIQMTQSPSS LSASVGDRVT ITCRASQAIR NDLGWYQQKP GKAPKLLIYT AFSLQSGVPS    60
RFSGSKSGTD FTLTISSLQP EDFATYYCLQ DYTNPRTFGQ GTKVEIK                107

SEQ ID NO: 149          moltype = AA   length = 345
FEATURE                 Location/Qualifiers
REGION                  1..345
                        note = Synthetic
source                  1..345
                        mol_type = protein
                        organism = synthetic construct
SEQUENCE: 149
QVMDFLFEKW KLYGDQCHHN LSLLPPPTEL VCNRTFDKYS CWPDTPANTT ANISCPWYLP    60
WHHKVQHRFV FKRCGPDGQW VRGPRGQPWR DASQCQMDGE EIEVQKEVAK MYSSFQVMDK  120
THTCPPCPAP ELLGGPSVFL FPPKPKDTLM ISRTPEVTCV VVDVSHEDPE VKFNWYVDGV  180
EVHNAKTKPR EEQYNSTYRV VSVLTVLHQD WLNGKEYKCK VSNKALPAPI EKTISKAKGQ  240
PREPQVYTLP PSRDELTKNQ VSLTCLVKGF YPSDIAVEWE SNGQPENNYK TTPPVLDSDG  300
SFFLYSKLTV DKSRWQQGNV FSCSVMHEAL HNHYTQKSLS LSPGK                  345

SEQ ID NO: 150          moltype = AA   length = 348
FEATURE                 Location/Qualifiers
REGION                  1..348
                        note = Synthetic
source                  1..348
                        mol_type = protein
                        organism = synthetic construct
SEQUENCE: 150
QVMDFLFEKW KLYGDQCHHN LSLLPPPTEL VCNRTFDKYS CWPDTPANTT ANISCPWYLP    60
WHHKVQHRFV FKRCGPDGQW VRGPRGQPWR DASQCQMDGE EIEVQKEVAK MYSSFQVMGP  120
GDKTHTCPPC PAPELLGGPS VFLFPPKPKD TLMISRTPEV TCVVVDVSHE DPEVKFNWYV  180
```

```
DGVEVHNAKT KPREEQYNST YRVVSVLTVL HQDWLNGKEY KCKVSNKALP APIEKTISKA  240
KGQPREPQVY TLPPSRDELT KNQVSLTCLV KGFYPSDIAV EWESNGQPEN NYKTTPPVLD   300
SDGSFFLYSK LTVDKSRWQQ GNVFSCSVMH EALHNHYTQK SLSLSPGK                348

SEQ ID NO: 151          moltype = AA   length = 146
FEATURE                 Location/Qualifiers
REGION                  1..146
                        note = Synthetic
source                  1..146
                        mol_type = protein
                        organism = synthetic construct
SEQUENCE: 151
QVMDFLFEKW KLYGDQCHHN LSLLPPPTEL VCNRTFDKYS CWPDTPANTT ANISCPWYLP   60
WHHKVQHRFV FKRCGPDGQW VRGPRGQPWR DASQCQMDGE EIEVQKEVAK MYSSFQVMEQ   120
KLISEEDLGG EQKLISEEDL HHHHHH                                        146

SEQ ID NO: 152          moltype = AA   length = 351
FEATURE                 Location/Qualifiers
REGION                  1..351
                        note = Synthetic
source                  1..351
                        mol_type = protein
                        organism = synthetic construct
SEQUENCE: 152
GAPQVMDFLF EKWKLYGDQC HHNLSLLPPP TELVCNRTFD KYSCWPDTPA NTTANISCPW   60
YLPWHHKVQH RFVFKRCGPD GQWVRGPRGQ PWRDASQCQM DGEELEVQKE VAKMYSSFQV   120
MGPGDKTHTC PPCPAPELLG GPSVFLFPPK PKDTLMISRT PEVTCVVVDV SHEDPEVKFN   180
WYVDGVEVHN AKTKPREEQY NSTYRVVSVL TVLHQDWLNG KEYKCKVSNK ALPAPIEKTI   240
SKAKGQPREP QVYTLPPSRD ELTKNQVSLT CLVKGFYPSD IAVEWESNGQ PENNYKTTPP   300
VLDSDGSFFL YSKLTVDKSR WQQGNVFSCS VMHEALHNHY TQKSLSLSPG K            351

SEQ ID NO: 153          moltype = AA   length = 477
FEATURE                 Location/Qualifiers
source                  1..477
                        mol_type = protein
                        organism = Homo sapiens
SEQUENCE: 153
MPPCQPQRPL LLLLLLLACQ PQVPSAQVMD FLFEKWKLYG DQCHHNLSLL PPPTELVCNR   60
TFDKYSCWPD TPANTTANIS CPWYLPWHHK VQHRFVFKRC GPDGQWVRGP RGQPWRDASQ   120
CQMDGEEIEV QKEVAKMYSS FQVMYTVGYS LSLGALLLAL AILGGLSKLH CTRNAIHANL   180
FASFVLKASS VLVIDGLLRT RYSQKIGDDL SVSTWLSDGA VAGCRVAAVF MQYGIVANYC   240
WLLVEGLYLH NLLGLATLPE RSFFSLYLGI GWGAPMLFVV PWAVVKCLFE NVQCWTSNDN   300
MGFWWILRFP VFLAILINFF IFVRIVQLLV AKLRARQMHY KFRLAKS TLTLIPLLGV      360
HEVVFAFVTD EHAQGTLRSA KLFFDLFLSS FQGLLVAVLY CFLNKEVQSE LRRRWHRWRL   420
GKVLWEERNT SNHRASSSPG HGPPSKELQF GRGGGSQDSS AETPLAGGLP RLAESPF      477

SEQ ID NO: 154          moltype = AA   length = 485
FEATURE                 Location/Qualifiers
source                  1..485
                        mol_type = protein
                        organism = Mus musculus
SEQUENCE: 154
MALTQLHCPH LLLLLLVLSC LPEAPSAQVM DFLFEKWKLY SDQCHHNLSL LPPPTELVCN   60
RTFDKYSCWP DTPNNTTANI SCPWYLPWYH KVQHRLVFKR CGPDGQWVRG PRGQPWRNAS   120
QCQLDDEEIE VQKGVAKMYS SQQVMYTVGY SLSLGALLLA LVILLGLRKL HCTRNYIHGN   180
LFASFVLKAG SVLVIDWLLK TRYSQKIGDD LSVSVWLSDG AMAGCRVATV IMQYGIIANY   240
CWLLVEGVYL YSLLSLATFS ERSFFSLYLG IGWGAPLLFV IPWVVVKCLF ENVQCWTSND   300
NMGFWWILRI PVFLALLINF FIFVHIIHLL VAKLRAHQMH YADYKFRLAR STLTLIPLLG   360
VHEVVFAFVT DEHAQGTLRS TKLFFDLFLS SFQGLLVAVL YCFLNKEVQA ELMRRWRQWQ   420
EGKALQEERL ASSHGSHMAP AGPCHGDPCE KLQLMSAGSS SGTGCVPSME TSLASSLPRL   480
ADSPT                                                               485

SEQ ID NO: 155          moltype = AA   length = 491
FEATURE                 Location/Qualifiers
source                  1..491
                        mol_type = protein
                        organism = Macaca fascicularis
SEQUENCE: 155
MAPCQPRRPL LLLLLLLACQ PQAPSAQVMD FLFEKWKLYG DQCHHNLSLL PPPTELVCNR   60
TFDKYSCWPD TPANTTANIS CPWYLPWHHK VQHRFVFKRC GPDGQWVRGP RGQPWRDASQ   120
CQMDGEELEV QKEVAKMYSS FQVMYTVGYS LSLGALLLAL AILGGISKLH CTRNAIHANL   180
FVSFVLKASS VLVIDGLLRT RYSQKIGDDL SVSIWLSDGA VAGCRVAAVF MQYGVVANYC   240
WLLVEGLYLH NLLGLATLPE RSFFSLYLGI GWGAPMLFVV PWVVVRCLFE NIQCWTSNDN   300
MGFWWILRFP VFLAILINFF IFIRIVHLLV AKLRAREMHH TDYKFRLAKS TLTLIPLLGV   360
HEVVFAFVTD EHAQGTLRFA KLFFDLFLSS FQGLLVAVLY CFLNKEVQSE LRRHWHRWRL   420
GKVLQEERGT SNHKAPSAPG QGLPGKKLQS GRDGGSQDSS AEIPLAGGLP RLAESPFSTL   480
LGPQLGLDSG T                                                        491

SEQ ID NO: 156          moltype = AA   length = 485
```

```
FEATURE                 Location/Qualifiers
source                  1..485
                        mol_type = protein
                        organism = Rattus norvegicus
SEQUENCE: 156
MVLTQLHCPY LLLLLVVLSC LPKAPSAQVM DFLFEKWKLY SDQCHHNLSL LPPPTELVCN    60
RTFDKYSCWP DTPPNTTANI SCPWYLPWYH KVQHRLVFKR CGPDGQWVRG PRGQSWRDAS   120
QCQMDDDEIE VQKGVAKMYS SYQVMYTVGY SLSLGALLLA LVILLGLRKL HCTRNYIHGN   180
LFASFVLKAG SVLVIDWLLK TRYSQKIGDD LSVSVWLSDG AVAGCRVATV IMQYGIIANY   240
CWLLVEGVYL YSLLSITTFS EKSFFSLYLC IGWGSPLLFV IPWVVVKCLF ENVQCWTSND   300
NMGFWWILRI PVLLAILINF FIFVRIIHLL VAKLRAHQMH YADYKFRLAR STLTLIPLLG   360
VHEVVFAFVT DEHAQGTLRS TKLFFDLFFS SFQGLLVAVL YCFLNKEVQA ELLRRWRRWQ   420
EGKALQEERM ASSHGSHMAP AGTCHGDPCE KLQLMSAGSS SGTGCEPSAK TSLASSLPRL   480
ADSPT                                                               485

SEQ ID NO: 157          moltype = DNA   length = 1434
FEATURE                 Location/Qualifiers
source                  1..1434
                        mol_type = unassigned DNA
                        organism = Homo sapiens
SEQUENCE: 157
atgccccct gccagccaca gcgaccctg ctgctgttgc tgctgctgct ggcctgccag      60
ccacaggtcc cctccgctca ggtgatggac ttcctgtttg agaagtggaa gctctacggt  120
gaccagtgtc accacaacct gagcctgctg cccctccca cggagctggt gtgcaacaga   180
accttcgaca agtattcctg ctggccggac accccgcca ataccacggc caacatctcc    240
tgccctggt acctgccttg gcaccacaaa gtgcaacacc gcttcgtgtt caagagatgc    300
gggcccgacg gtcagtgggg gcgtggaccc cggggcagc cttggcgtga tgcctcccag    360
tgccagatgg atggcgagga gattgaggtc cagaaggagg tggccaagat gtacagcagc   420
ttccaggtga tgtacacagt gggctacagc ctgtccctgg gggccctgct cctcgccttg    480
gccatcctgg ggggcctcag caagctgcac tgcacccgca atgccatcca cgcgaatctg    540
tttgcgtcct tcgtgctgaa agccagctcc gtgctggtca ttgatgggct gctcaggacc    600
cgctacagcc agaaaattgg cgacgacctc agtgtcagca cctggctcag tgatggagcg    660
gtggctggct gccgtgtggc cgcggtgttc atgcaatatg gcatcgtggc caactactgc    720
tggctgctgg tggagggcct gtacctgcac aacctgctgg gcctggccac cctccccgag    780
aggagcttct tcagcctcta cctgggcatc ggctgggtg ccccatgct gttcgtcgtc     840
ccctgggcag tggtcaagtg tctgttcgag aacgtccagt gctgaccag caatgacaac    900
atgggcttct ggtggatcct gcggttcccc gtcttcctgg ccatcctgat caacttcttc    960
atcttcgtcc gcatcgttca gctgctcgtg gccaagctgc gggcacggca gatgcaccac   1020
acagactaca gttccggct ggccaagtcc acgctgaccc tcatccctct gctgggcgtc   1080
cacgaagtgg tctttgcctt cgtgacggac gagcacgccc agggcaccct gcgctccgcc   1140
aagctcttct tcgacctctt cctcagctcc ttccagggcc tgctggtggc tgtcctctac   1200
tgcttcctca caaggaggt gcagtcggag ctgcggcggc gttggcaccg ctggcgcctg   1260
gcaaagtgc tatgggagga gcggaacacc agcaaccgca ggcctcatc ttcgcccggc    1320
cacggccctc ccagcaagga gctgcagttt gggaggggtg gtggcagcca ggattcatct   1380
gcggagaccc ccttggctgg tggcctccct agattggctg agagcccctt ctga         1434

SEQ ID NO: 158          moltype = DNA   length = 354
FEATURE                 Location/Qualifiers
source                  1..354
                        mol_type = unassigned DNA
                        organism = Homo sapiens
SEQUENCE: 158
caggtgatgg acttcctgtt tgagaagtgg aagctctacg gtgaccagtg tcaccacaac    60
ctgagcctgt gcccctcc cacggagctg gtgtgcaaca gaaccttcga caagtattcc   120
tgctgccgg acacccccgc caataccacg gccaacatct cctgccccctg gtacctgcct   180
tggcaccaca aagtgcaaca ccgcttcgtg ttcaagagat gcgggcccga cggtcagtgg   240
gtgcgtggac cccgggggca gccttggcgt gatgcctccc agtgccagat ggatggcgag   300
gagattgagg tccagaagga ggtggccaag atgtacagca gcttccaggt gatg         354

SEQ ID NO: 159          moltype = AA    length = 118
FEATURE                 Location/Qualifiers
source                  1..118
                        mol_type = protein
                        organism = Homo sapiens
SEQUENCE: 159
QVMDFLFEKW KLYGDQCHHN LSLLPPPTEL VCNRTFDKYS CWPDTPANTT ANISCPWYLP    60
WHHKVQHRFV FKRCGPDGQW VRGPRGQPWR DASQCMDGE EIEVQKEVAK MYSSFQVM     118

SEQ ID NO: 160          moltype = DNA   length = 24
FEATURE                 Location/Qualifiers
misc_feature            1..24
                        note = Synthetic
source                  1..24
                        mol_type = other DNA
                        organism = synthetic construct
SEQUENCE: 160
ggattcacct ttaacaacta tgcc                                           24

SEQ ID NO: 161          moltype = AA    length = 8
```

```
FEATURE                 Location/Qualifiers
REGION                  1..8
                        note = Synthetic
source                  1..8
                        mol_type = protein
                        organism = synthetic construct
SEQUENCE: 161
GFTFNNYA                                                                    8

SEQ ID NO: 162          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 162
attagtggta gcggtggtac taca                                                 24

SEQ ID NO: 163          moltype = AA  length = 8
FEATURE                 Location/Qualifiers
REGION                  1..8
                        note = Synthetic
source                  1..8
                        mol_type = protein
                        organism = synthetic construct
SEQUENCE: 163
ISGSGGTT                                                                    8

SEQ ID NO: 164          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 164
gcgaaagatt ctaactgggg aaatttcgat ctc                                       33

SEQ ID NO: 165          moltype = AA  length = 11
FEATURE                 Location/Qualifiers
REGION                  1..11
                        note = Synthetic
source                  1..11
                        mol_type = protein
                        organism = synthetic construct
SEQUENCE: 165
AKDSNWGNFD L                                                               11

SEQ ID NO: 166          moltype = DNA  length = 36
FEATURE                 Location/Qualifiers
misc_feature            1..36
                        note = Synthetic
source                  1..36
                        mol_type = other DNA
                        organism = synthetic construct
SEQUENCE: 166
cagagtgttt tatacaggtc caacaatagg aacttc                                    36

SEQ ID NO: 167          moltype = AA  length = 12
FEATURE                 Location/Qualifiers
REGION                  1..12
                        note = Synthetic
source                  1..12
                        mol_type = protein
                        organism = synthetic construct
SEQUENCE: 167
QSVLYRSNNR NF                                                              12

SEQ ID NO: 168          moltype =  length =
SEQUENCE: 168
000

SEQ ID NO: 169          moltype =  length =
SEQUENCE: 169
000

SEQ ID NO: 170          moltype = DNA  length = 27
FEATURE                 Location/Qualifiers
```

```
misc_feature            1..27
                        note = Synthetic
source                  1..27
                        mol_type = other DNA
                        organism = synthetic construct
SEQUENCE: 170
caacaatatt atactactcc gtacact                                           27

SEQ ID NO: 171          moltype = AA   length = 9
FEATURE                 Location/Qualifiers
REGION                  1..9
                        note = Synthetic
source                  1..9
                        mol_type = protein
                        organism = synthetic construct
SEQUENCE: 171
QQYYTTPYT                                                                9

SEQ ID NO: 172          moltype = DNA  length = 354
FEATURE                 Location/Qualifiers
misc_feature            1..354
                        note = Synthetic
source                  1..354
                        mol_type = other DNA
                        organism = synthetic construct
SEQUENCE: 172
gaggtgcagc tggtggagtc tgggggaggc ttggtacagc ctggggggtc cctgagactc        60
tcctgtgcag cctctggatt cacctttaac aactatgcca tgaactgggt ccgccaggct       120
ccaggaaagg gactggactg ggtctcaact attagtggta gcggtggtac tacaaactac       180
gcagactccg tgaagggccg tttcattatt tcccgagaca gttccaaaca cacgctgtat       240
ctgcaaatga acagcctgag agccgaggac acggccgtat attactgtgc gaaagattct       300
aactggggaa atttcgatct ctggggccgt ggcaccctgg tcactgtctc ctca             354

SEQ ID NO: 173          moltype = AA   length = 118
FEATURE                 Location/Qualifiers
REGION                  1..118
                        note = Synthetic
source                  1..118
                        mol_type = protein
                        organism = synthetic construct
SEQUENCE: 173
EVQLVESGGG LVQPGGSLRL SCAASGFTFN NYAMNWVRQA PGKGLDWVST ISGSGGTTNY        60
ADSVKGRFII SRDSSKHTLY LQMNSLRAED TAVYYCAKDS NWGNFDLWGR GTLVTVSS        118

SEQ ID NO: 174          moltype = DNA  length = 339
FEATURE                 Location/Qualifiers
misc_feature            1..339
                        note = Synthetic
source                  1..339
                        mol_type = other DNA
                        organism = synthetic construct
SEQUENCE: 174
gacatcgtga tgacccagtc tccagactcc ctggctgtgt ctctgggcga gagggccacc        60
atcaactgca gtccagcca gagtgtttta tacaggtcca acaataggaa cttcttaggt       120
tggtaccagc agaaaccagg gcagcctcct aatctactca tttactgggc atctacccgg       180
gaatccgggg tccctgaccg attcagtggc agcgggtctg ggacagattt cactctcacc       240
atcagcagcc tgcaggctga agatgtggca gtttattact gtcaacaata ttatactacc       300
ccgtacactt ttggccaggg gaccaagctg gagatcaaa                              339

SEQ ID NO: 175          moltype = AA   length = 113
FEATURE                 Location/Qualifiers
REGION                  1..113
                        note = Synthetic
source                  1..113
                        mol_type = protein
                        organism = synthetic construct
SEQUENCE: 175
DIVMTQSPDS LAVSLGERAT INCKSSQSVL YRSNNRNFLG WYQQKPGQPP NLLIYWASTR        60
ESGVPDRFSG SGSGTDFTLT ISSLQAEDVA VYYCQQYYTT PYTFGQGTKL EIK              113

SEQ ID NO: 176          moltype = DNA  length = 381
FEATURE                 Location/Qualifiers
misc_feature            1..381
                        note = Synthetic
source                  1..381
                        mol_type = other DNA
                        organism = synthetic construct
SEQUENCE: 176
gagatgcaac tggtggagtc tgggggaggc ttggtccagc ctggggggtc cctgagactc        60
```

```
tcctgtgcag cctctggatt cacctttagt agtcactgga tgaagtgggt ccgccaggct   120
ccagggaagg ggctggagtg ggtgccaac  ataaaccaag atggaagtga gaaatactat   180
gtggactctg tgaagggccg attcaccatc tccagagaca cgccaagaa  ctcactgttt   240
ctgcaaatga acagcctgag agccgaggac acggctgtgt attactgtgc gagagatatt   300
gtactaatgg tctatgatat ggactactac tactacggta tggacgtctg gggccaaggg   360
accacggtca ccgtctcctc a                                              381

SEQ ID NO: 177              moltype = AA   length = 127
FEATURE                     Location/Qualifiers
REGION                      1..127
                            note = Synthetic
source                      1..127
                            mol_type = protein
                            organism = synthetic construct
SEQUENCE: 177
EMQLVESGGG LVQPGGSLRL SCAASGFTFS SHWMKWVRQA PGKGLEWVAN INQDGSEKYY    60
VDSVKGRFTI SRDNAKNSLF LQMNSLRAED TAVYYCARDI VLMVYDMDYY YYGMDVWGQG   120
TTVTVSS                                                             127

SEQ ID NO: 178              moltype = DNA   length = 24
FEATURE                     Location/Qualifiers
misc_feature                1..24
                            note = Synthetic
source                      1..24
                            mol_type = other DNA
                            organism = synthetic construct
SEQUENCE: 178
ggattcacct ttagtagtca ctgg                                           24

SEQ ID NO: 179              moltype = AA   length = 8
FEATURE                     Location/Qualifiers
REGION                      1..8
                            note = Synthetic
source                      1..8
                            mol_type = protein
                            organism = synthetic construct
SEQUENCE: 179
GFTFSSHW                                                             8

SEQ ID NO: 180              moltype = DNA   length = 24
FEATURE                     Location/Qualifiers
misc_feature                1..24
                            note = Synthetic
source                      1..24
                            mol_type = other DNA
                            organism = synthetic construct
SEQUENCE: 180
ataaaccaag atggaagtga gaaa                                           24

SEQ ID NO: 181              moltype = AA   length = 8
FEATURE                     Location/Qualifiers
REGION                      1..8
                            note = Synthetic
source                      1..8
                            mol_type = protein
                            organism = synthetic construct
SEQUENCE: 181
INQDGSEK                                                             8

SEQ ID NO: 182              moltype = DNA   length = 60
FEATURE                     Location/Qualifiers
misc_feature                1..60
                            note = Synthetic
source                      1..60
                            mol_type = other DNA
                            organism = synthetic construct
SEQUENCE: 182
gcgagagata ttgtactaat ggtctatgat atggactact actactacgg tatggacgtc    60

SEQ ID NO: 183              moltype = AA   length = 20
FEATURE                     Location/Qualifiers
REGION                      1..20
                            note = Synthetic
source                      1..20
                            mol_type = protein
                            organism = synthetic construct
SEQUENCE: 183
ARDIVLMVYD MDYYYYGMDV                                                20
```

```
SEQ ID NO: 184          moltype = DNA  length = 336
FEATURE                 Location/Qualifiers
misc_feature            1..336
                        note = Synthetic
source                  1..336
                        mol_type = other DNA
                        organism = synthetic construct
SEQUENCE: 184
gatattgtga tgactcagtc tccactctcc ctgcccgtca ccctggaga gccggcctcc    60
atctcctgca ggtctagtca gagcctcctg catagtaatg gaaacaacta tttggattgg   120
tacctgcaga agccagggca gtctccacag ctcctgatct atttgggttc taatcgggcc   180
tccggggtcc ctgacaggtt cagtggcagt ggatcaggca cagatttac actgaaaatc    240
agcagagtgg aggctgagga tgttggggtt tattactgca tgcaaactct acaaactccg   300
ctcactttcg gcggagggac caaggtggag atcaaa                             336

SEQ ID NO: 185          moltype = AA  length = 112
FEATURE                 Location/Qualifiers
REGION                  1..112
                        note = Synthetic
source                  1..112
                        mol_type = protein
                        organism = synthetic construct
SEQUENCE: 185
DIVMTQSPLS LPVTPGEPAS ISCRSSQSLL HSNGNNYLDW YLQKPGQSPQ LLIYLGSNRA    60
SGVPDRFSGS GSGTDFTLKI SRVEAEDVGV YYCMQTLQTP LTFGGGTKVE IK           112

SEQ ID NO: 186          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 186
cagagcctcc tgcatagtaa tggaaacaac tat                                33

SEQ ID NO: 187          moltype = AA  length = 11
FEATURE                 Location/Qualifiers
REGION                  1..11
                        note = Synthetic
source                  1..11
                        mol_type = protein
                        organism = synthetic construct
SEQUENCE: 187
QSLLHSNGNN Y                                                        11

SEQ ID NO: 188          moltype =     length =
SEQUENCE: 188
000

SEQ ID NO: 189          moltype =     length =
SEQUENCE: 189
000

SEQ ID NO: 190          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 190
atgcaaactc tacaaactcc gctcact                                       27

SEQ ID NO: 191          moltype = AA  length = 9
FEATURE                 Location/Qualifiers
REGION                  1..9
                        note = Synthetic
source                  1..9
                        mol_type = protein
                        organism = synthetic construct
SEQUENCE: 191
MQTLQTPLT                                                           9

SEQ ID NO: 192          moltype = DNA  length = 2076
FEATURE                 Location/Qualifiers
source                  1..2076
                        mol_type = unassigned DNA
                        organism = Homo sapiens
```

```
SEQUENCE: 192
atgggcaccg tcagctccag gcggtcctgg tggccgctgc cactgctgct gctgctgctg    60
ctgctcctgg gtcccgcggg cgcccgtgcg caggaggacg aggacggcga ctacgaggag   120
ctggtgctag ccttgcgttc cgaggaggac ggcctggccg aagcacccga gcacggaacc   180
acagccacct tccaccgctg cgccaaggat ccgtgggacg tgcctggcac ctacgtggtg   240
gtgctgaagg aggagaccca cctctcgcag tcagagcgca ctgcccgccg cctgcaggcc   300
caggctgccc gccggggata cctcaccaag atcctgcatg tcttccatgg ccttcttcct   360
ggcttcctgg tgaagatgag tggcgacctg ctggagctgg ccttgaagtt gcccccatgtc   420
gactacatcg aggaggactc ctctgtcttt gcccagagca tccgtggaa cctggagcgg   480
attaccccctc cacggtaccg ggcggatgaa taccagcccc ccgacggagg cagcctggtg   540
gaggtgtatc tcctagacac cagcatacag agtgaccacc gggaaatcga gggcagggtc   600
atggtcaccg acttcgagaa tgtgcccgag gaggacggga cccgcttcca cagacaggcc   660
agcaagtgtg acagtcatgg cacccacctg caggggtgtc agcggccg ggatgccggc   720
gtggccaagg gtgccagcat gcgcagcctg cgcgtgctca actgccaagg gaagggcacg   780
gttagcggca ccctcatagg cctggagttt attcggaaaa gccagctggt ccagcctgtg   840
gggcactgtg tggtgctgct gccccctggcg ggtgggtaca gccgcgtcct caacgccgcc   900
tgccagcgcc tggcgagggc tgggtcgtg ctggtcaccg ctgccggcaa cttccgggac   960
gatgcctgcc tctactcccc agcctcagct cccgaggtca tcacagttgg ggccaccaat  1020
gcccaggacc agccggtgac cctggggact ttggggacca actttggccg ctgtgtggac  1080
ctctttgccc caggggagga catcattggt gcctccagcg actgcagcac ctgctttgtg  1140
tcacagagtg ggacatcaca ggctgctgcc cacgtggctg gcattgcagc catgatgctg  1200
tctgccgagc cggagctcac cctgccgag ttgaggcaga gactgatcca cttctctgcc  1260
aaagatgtca tcaatgaggc ctggttccct gaggaccagc gggtactgac ccccaacctg  1320
gtggccgccc tgccccccag cacccatggg gcaggttggc agctgttttg caggactgtg  1380
tggtcagcac actcggggcc tacacggatg ccacagcca tcgcccgctg cgccccagat  1440
gaggacgctgc tgagctgctc cagtttctcc aggagtggga agcggcggga gcggcatga  1500
gaggcccaag ggggcaagct ggtctgccgg gcccacaacg cttttggggg tgagggtgtc  1560
tacgccattg ccaggtgctg cctgctaccc caggccaact gcagcgtcca cagctcca   1620
ccagctgagg ccagcatggg gacccgtgtc cactgccacc aacagggcca cgtcctcaca  1680
ggctgcagct cccactggga ggtggaggac cttggccacc acaagccgcc tgtgctgagg  1740
ccacgaggtc agcccaacca gtgcgtgggc cacagggagg ccagcatcca cgcttcctgc  1800
tgccatgccc caggtctgga atgcaaagtc aaggagcatg gaatcccggc ccctcaggag  1860
caggtgaccg tggcctgcga ggagggctgg accctgactg gctgcagtgc cctccctggg  1920
acctcccacg tcctggggc ctacgccgta gacaacacg tgtagtcag gagccgggac  1980
gtcagcacta caggcagcac cagcgaagag gccgtgacag ccgttgccat ctgctgccgg  2040
agccgcacc tggcgcaggc ctcccaggag ctccag                             2076

SEQ ID NO: 193         moltype = AA   length = 692
FEATURE                Location/Qualifiers
source                 1..692
                       mol_type = protein
                       organism = Homo sapiens
SEQUENCE: 193
MGTVSSRRSW WPLPLLLLLL LLLGPAGARA QEDEDGDYEE LVLALRSEED GLAEAPEHGT    60
TATFHRCAKD PWRLPGTYVV VLKEETHLSQ SERTARRLQA QAARRGYLTK ILHVFHGLLP   120
GFLVKMSGDL LELALKLPHV DYIEEDSSVF AQSIPWNLER ITPPRYRADE YQPPDGGSLV   180
EVYLLDTSIQ SDHREIEGRV MVTDFENVPE EDGTRFHRQA SKCDSHGTHL AGVVSGRDAG   240
VAKGASMRSL RVLNCQGKGT VSGTLIGLEF IRKSQLVQPV GPLVVLLPLA GGYSRVLNAA   300
CQRLARAGVV LVTAAGNFRD DACLYSPASA PEVITVGATN AQDQPVTLGT LGTNFGRCVD   360
LFAPGEDIIG ASSDCSTCFV SQSGTSQAAA HVAGIAAMML SAEPELTLAE LRQRLIHFSA   420
KDVINEAWFP EDQRVLTPNL VAALPPSTHG AGWQLFCRTV WSAHSGPTRM ATAIARCAPD   480
EELLSCSSFS RSGKRRGERM EAQGGKLVCR AHNAFGGEGV YAIARCCLLP QANCSVHTAP   540
PAEASMGTRV HCHQQGHVLT GCSSHWEVED LGTHKPPVLR PRGQPNQCVG HREASIHASC   600
CHAPGLECKV KEHGIPAPQE QVTVACEEGW TLTGCSALPG TSHVLGAYAV DNTCVVRSRD   660
VSTTGSTEE AVTAVAICCR SRHLAQASQE LQ                                  692

SEQ ID NO: 194         moltype = AA   length = 115
FEATURE                Location/Qualifiers
REGION                 1..115
                       note = Synthetic
source                 1..115
                       mol_type = protein
                       organism = synthetic construct
SEQUENCE: 194
EVQLVQSGGG LVHPGGSLRL SCAGSGFTFS RNAMFWVRQA PGKGLEWVSG IGTGGATNYA    60
DSVKGRFTIS RDNAKNSLYL QMNSLRAEDM AVYYCARGRY YFDYWGQGTL VTVSS         115

SEQ ID NO: 195         moltype = AA   length = 8
FEATURE                Location/Qualifiers
REGION                 1..8
                       note = Synthetic
source                 1..8
                       mol_type = protein
                       organism = synthetic construct
SEQUENCE: 195
GFTFSRNA                                                              8

SEQ ID NO: 196         moltype = AA   length = 7
FEATURE                Location/Qualifiers
```

| | | |
|---|---|---|
| REGION | 1..7<br>note = Synthetic | |
| source | 1..7<br>mol_type = protein<br>organism = synthetic construct | |
| SEQUENCE: 196<br>IGTGGAT | | 7 |
| SEQ ID NO: 197<br>FEATURE<br>REGION | moltype = AA length = 9<br>Location/Qualifiers<br>1..9<br>note = Synthetic | |
| source | 1..9<br>mol_type = protein<br>organism = synthetic construct | |
| SEQUENCE: 197<br>ARGRYYFDY | | 9 |
| SEQ ID NO: 198<br>FEATURE<br>REGION | moltype = AA length = 109<br>Location/Qualifiers<br>1..109<br>note = Synthetic | |
| source | 1..109<br>mol_type = protein<br>organism = synthetic construct | |
| SEQUENCE: 198<br>EIVLTQSPGT LSLSPGERAT LSCRASQSVS SSYLAWYQQK PGQAPRLLIF GASSRATGIP<br>DRFSGSGSGT DFTLTISRLE PEDFAVYYCQ QYGSSPPWTF GQGTKVEIK | | 60<br>109 |
| SEQ ID NO: 199<br>FEATURE<br>REGION | moltype = AA length = 7<br>Location/Qualifiers<br>1..7<br>note = Synthetic | |
| source | 1..7<br>mol_type = protein<br>organism = synthetic construct | |
| SEQUENCE: 199<br>QSVSSSY | | 7 |
| SEQ ID NO: 200<br>SEQUENCE: 200<br>000 | moltype = length = | |
| SEQ ID NO: 201<br>FEATURE<br>REGION | moltype = AA length = 10<br>Location/Qualifiers<br>1..10<br>note = Synthetic | |
| source | 1..10<br>mol_type = protein<br>organism = synthetic construct | |
| SEQUENCE: 201<br>QQYGSSPPWT | | 10 |
| SEQ ID NO: 202<br>SEQUENCE: 202<br>000 | moltype = length = | |
| SEQ ID NO: 203<br>SEQUENCE: 203<br>000 | moltype = length = | |
| SEQ ID NO: 204<br>SEQUENCE: 204<br>000 | moltype = length = | |
| SEQ ID NO: 205<br>SEQUENCE: 205<br>000 | moltype = length = | |
| SEQ ID NO: 206<br>SEQUENCE: 206<br>000 | moltype = length = | |
| SEQ ID NO: 207<br>SEQUENCE: 207<br>000 | moltype = length = | |

HUMAN ANTIBODIES TO THE HUMAN GLUCAGON RECEPTOR (HGCGR) AND METHODS OF USE THEREOF TO LOWER BLOOD GLUCOSE OR KETONE LEVELS

CROSS-REFERENCE TO RELATED APPLICATIONS

This application is a Continuation of U.S. patent application Ser. No. 16/837,930, filed Apr. 1, 2020, now U.S. Pat. No. 11,498,970, issued Nov. 15, 2022, which is a Continuation of U.S. patent application Ser. No. 16/256,190, filed Jan. 24, 2019, now U.S. Pat. No. 10,640,566, issued May 5, 2020, which is a Continuation of U.S. patent application Ser. No. 15/415,672, filed Jan. 25, 2017, now U.S. Pat. No. 10,233,250, issued Mar. 19, 2019, which is a Divisional of U.S. patent application Ser. No. 14/821,652, filed Aug. 7, 2015, now U.S. Pat. No. 9,587,029, issued Mar. 7, 2017, which is a Divisional of U.S. patent application Ser. No. 14/014,517, filed Aug. 30, 2013, now U.S. Pat. No. 9,127,068, issued Sep. 8, 2015, which is a Continuation of U.S. patent application Ser. No. 13/301,944, filed Nov. 22, 2011, now U.S. Pat. No. 8,545,847, issued Oct. 1, 2013, which claims the benefit under § 119 (e) of U.S. Provisional Application Ser. No. 61/416,409, filed Nov. 23, 2010, U.S. Provisional Application Ser. No. 61/481,958, filed May 3, 2011, and U.S. Provisional Application Ser. No. 61/551,032, filed Oct. 25, 2011, which applications are herein specifically incorporated by reference in their entirety.

SEQUENCE LISTING

An official copy of the sequence listing is submitted concurrently with the specification electronically via Patent Center. The contents of the electronic sequence listing (1400CON4-US_Sequence_Listing.xml; Size: 249,856 bytes; and Date of Creation: Oct. 11, 2022) is herein incorporated by reference in its entirety.

FIELD OF THE INVENTION

The present invention is related to human antibodies and antigen-binding fragments of human antibodies that specifically bind the glucagon receptor, and therapeutic methods of using those antibodies.

STATEMENT OF RELATED ART

Glucagon is a 29 amino acid hormone produced by the alpha cells of pancreatic islets. Glucagon maintains normal levels of glucose in animals, including humans, by counterbalancing the effects of insulin. It is an imbalance of glucagon and insulin that may play an important role in several diseases, such as diabetes mellitus and diabetic ketoacidosis. In particular, studies have shown that higher basal glucagon levels and lack of suppression of postprandial glucagon secretion contribute to diabetic conditions in humans (Muller et al., N Eng J Med 283:109-115 (1970)).

It is believed that glucagon's effects on elevating blood glucose levels are mediated in part by the activation of certain cellular pathways following the binding of glucagon (GCG) to its receptor (designated GCGR). GCGR is a member of the secretin subfamily (family B) of G-protein-coupled receptors and is predominantly expressed in the liver. The binding of glucagon to its receptor triggers a G-protein signal transduction cascade, activating intracellular cyclic AMP and leading to an increase in glucose output through de novo synthesis (gluconeogenesis) and glycogen breakdown (glycogenolysis) (Wakelam et al., Nature, (1986) 323:68-71; Unson et al., Peptides, (1989), 10:1171-1177; and Pittner and Fain, Biochem. J. (1991), 277:371-378).

The rat glucagon receptor was first isolated and purified by Jelinek et al (Jelinek, L. J. et al. (1993) Science 259 (5101): 1614-1616). Subsequently, the rat sequence was used to identify and clone the 477 amino acid human glucagon receptor sequence (Lok, S. et al. (1994) Gene 140:203-209; MacNeil, D. J. et al. (1994) Biochem. and Biophys. Res. Comm). U.S. Pat. No. 5,776,725 discloses an isolated nucleic acid sequence encoding a human or rat glucagon receptor.

Targeting glucagon production or function with a glucagon receptor antagonist, such as an anti-GCGR antibody, may be one method of controlling and lowering blood glucose, and as such, may prove useful for treating diseases such as diabetes mellitus or diabetic ketoacidosis. Furthermore, by lowering glucose levels, it may be possible to prevent or ameliorate certain of the long-term complications associated with elevated glucose levels in diabetic patients.

Early studies demonstrated that polyclonal antibodies to the rat glucagon receptor were able to block glucagon binding (Unson, C. G. (1996) PNAS 93 (1): 310-315). Monoclonal antibodies to the human glucagon receptor were described by Buggy et al. (Buggy, J. J. et al. (1995) J. Biol. Chem. 270 (13): 7474; Buggy, J. J. et al. (1996) Horm Metab Res. 28 (5): 215-9). The antibody described by Buggy et al. competed with glucagon for the hormone binding site of the receptor and recognized both the human and rat glucagon receptors, but not the mouse receptor. Wright et al. disclose a monoclonal antibody raised in a mouse against the human glucagon receptor and conducted detailed protein structure determination of the monoclonal antibody to the receptor (Wright, L. M. (2000) Acta Crystallographica Section D. 56 (5): 573-580). Other antibodies to the glucagon receptor are described in U.S. Pat. Nos. 5,770,445 and 7,947,809; European patent application EP2074149A2; EP patent EP0658200B1; US patent publications 2009/0041784; 2009/0252727; and 2011/0223160; and PCT publication WO2008/036341.

BRIEF SUMMARY OF THE INVENTION

In a first aspect, the invention provides fully human monoclonal antibodies (mAbs) and antigen-binding fragments thereof that bind to the human glucagon receptor (hGCGR) and inhibit or block its activity, for example, block the binding of glucagon to its receptor, thereby blocking the elevation of blood glucose levels. The antibodies or antigen binding fragments thereof may be useful for lowering blood glucose levels in a subject that suffers from a disease characterized by increased blood glucose levels, such as diabetes mellitus. The antibodies may also be used to treat a wide range of conditions and disorders in which blocking the interaction of glucagon with the glucagon receptor is desired, thereby having a beneficial effect. The antibodies may ultimately be used to prevent the long-term complications associated with elevated blood glucose levels in diabetic patients, or to ameliorate at least one symptom associated with elevated blood glucose levels in diabetic patients.

The antibodies of the invention can be full-length (for example, an IgG1 or IgG4 antibody) or may comprise only an antigen-binding portion (for example, a Fab, (ab')$_2$ or scFv fragment), and may be modified to affect functionality, e.g., to eliminate residual effector functions (Reddy et al., 2000, J. Immunol. 164:1925-1933).

In one embodiment, the invention provides an isolated human antibody or antigen-binding fragment thereof that specifically binds human glucagon receptor (hGCGR), wherein the antibody binds an ectodomain and/or an extracellular (EC) loop of human GCGR, wherein the ectodomain is the N-terminal domain of GCGR and wherein the EC loop is one or more of EC1, EC2 and EC3.

In one embodiment, the invention provides an antibody or fragment thereof, which binds the N-terminal domain comprising amino acid residues ranging from about amino acid residue number 27 to about amino acid residue 144 of SEQ ID NO: 153, or binds an EC loop of hGCGR, wherein the EC loop is one or more of EC1, EC2, and EC3, wherein EC1 comprises amino acid residues ranging from about amino acid residue 194 to about amino acid residue 226 of SEQ ID NO: 153; EC2 comprises amino acid residues ranging from about amino acid residue 285 to about amino acid residue 305 of SEQ ID NO: 153; and EC3 comprises amino acid residues ranging from about amino acid residue 369 to about amino acid residue 384 of SEQ ID NO: 153.

In one embodiment, the human antibody or antigen-binding fragment of a human antibody that binds hGCGR, comprises a heavy chain variable region (HCVR) having an amino acid sequence selected from the group consisting of SEQ ID NOs: 2, 18, 34, 50, 66, 70, 86, 90, 106, 110, 126, 130 and 146, or a substantially similar sequence thereof having at least 90%, at least 95%, at least 98% or at least 99% sequence identity. In certain embodiments, the antibody or antigen-binding fragment of an antibody that binds hGCGR comprises a HCVR having an amino acid sequence selected from the group consisting of SEQ ID NOs: 34, 70, 86, 110 and 126, or a substantially similar sequence thereof having at least 90%, at least 95%, at least 98% or at least 99% sequence identity.

In one embodiment, the human antibody or antigen-binding fragment of a human antibody that binds hGCGR comprises a light chain variable region (LCVR) having an amino acid sequence selected from the group consisting of SEQ ID NOs: 10, 26, 42, 58, 68, 78, 88, 98, 108, 118, 128, 138 and 148, or a substantially similar sequence thereof having at least 90%, at least 95%, at least 98% or at least 99% sequence identity. In certain embodiments, the antibody or antigen-binding fragment of an antibody that binds hGCGR comprises a LCVR having an amino acid sequence selected from the group consisting of SEQ ID NOs: 42, 78, 88, 118 and 128, or a substantially similar sequence thereof having at least 90%, at least 95%, at least 98% or at least 99% sequence identity.

In certain embodiments, the human antibody or fragment thereof that binds hGCGR comprises a HCVR/LCVR amino acid sequence pair selected from the group consisting of SEQ ID NOs: 2/10, 18/26, 34/42, 50/58, 66/68, 70/78, 86/88, 90/98, 106/108, 110/118, 126/128, 130/138, and 146/148. In certain embodiments, the HCVR/LCVR amino acid sequence pair is selected from the group consisting of SEQ ID NOs: 34/42, 70/78, 86/88, 110/118 and 126/128.

In a related embodiment, the invention includes an antibody or antigen-binding fragment of an antibody which specifically binds hGCGR, wherein the antibody or fragment thereof comprises the heavy and light chain CDR domains contained within heavy and light chain sequence pairs selected from the group consisting of SEQ ID NOs: 2/10, 18/26, 34/42, 50/58, 66/68, 70/78, 86/88, 90/98, 106/108, 110/118, 126/128, 130/138 and 146/148. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., J. Mol. Biol. 273:927-948 (1997); and Martin et al., Proc. Natl. Acad. Sci. USA 86:9268-9272 (1989). Public databases are also available for identifying CDR sequences within an antibody.

In certain embodiments, the present invention provides an isolated human antibody or an antigen-binding fragment thereof that binds specifically to hGCGR, wherein the antibody comprises a HCVR comprising the three heavy chain CDRs (HCDR1, HCDR2 and HCDR3) contained within the HCVR sequence selected from the group consisting of SEQ ID NOs: 2, 18, 34, 50, 66, 70, 86, 90, 106, 110, 126, 130 and 146; and a LCVR comprising the three light chain CDRs (LCDR1, LCDR2 and LCDR3) contained within the LCVR sequences selected from the group consisting of SEQ ID NOs: 10, 26, 42, 58, 68, 78, 88, 98, 108, 118, 128, 138 and 148.

In one embodiment, the present invention provides an isolated human antibody or antigen-binding fragment of a human antibody that binds hGCGR, comprising a HCDR3 domain having an amino acid sequence selected from the group consisting of SEQ ID NOs: 8, 24, 40, 56, 76, 96, 116 and 136, or a substantially similar sequence thereof having at least 90%, at least 95%, at least 98% or at least 99% sequence identity; and a LCDR3 domain having an amino acid sequence selected from the group consisting of SEQ ID NOs: 16, 32, 48, 64, 84, 104, 124 and 144, or a substantially similar sequence thereof having at least 90%, at least 95%, at least 98% or at least 99% sequence identity.

In one embodiment, the invention provides an antibody or fragment thereof that further comprises a HCDR1 domain having an amino acid sequence selected from the group consisting of SEQ ID NOs: 4, 20, 36, 52, 72, 92, 112 and 132, or a substantially similar sequence thereof having at least 90%, at least 95%, at least 98% or at least 99% sequence identity; a HCDR2 domain having an amino acid sequence selected from the group consisting of SEQ ID NOs: 6, 22, 38, 54, 74, 94, 114 and 134, or a substantially similar sequence thereof having at least 90%, at least 95%, at least 98% or at least 99% sequence identity; a LCDR1 domain having an amino acid sequence selected from the group consisting of SEQ ID NOs: 12, 28, 44, 60, 80, 100, 120 and 140, or a substantially similar sequence thereof having at least 90%, at least 95%, at least 98% or at least 99% sequence identity; and a LCDR2 domain having an amino acid sequence selected from the group consisting of SEQ ID NOs: 14, 30, 46, 62, 82, 102, 122 and 142, or a substantially similar sequence thereof having at least 90%, at least 95%, at least 98% or at least 99% sequence identity.

In one embodiment, the antibody or antigen-binding fragment of an antibody comprises:
  (a) a HCDR3 domain having an amino acid sequence selected from the group consisting of SEQ ID NOs: 8, 24, 40, 56, 76, 96, 116 and 136; and (b) a LCDR3 domain having an amino acid sequence selected from the group consisting of SEQ ID NOs: 16, 32, 48, 64, 84, 104, 124 and 144.

In one embodiment, the antibody or antigen-binding fragment of the antibody further comprises:

(c) a HCDR1 domain having an amino acid sequence selected from the group consisting of SEQ ID NOs: 4, 20, 36, 52, 72, 92, 112 and 132;

(d) a HCDR2 domain having an amino acid sequence selected from the group consisting of SEQ ID NOs: 6, 22, 38, 54, 74, 94, 114 and 134;

(e) a LCDR1 domain having an amino acid sequence selected from the group consisting of SEQ ID NOs: 12, 28, 44, 60, 80, 100, 120 and 140; and (f) a LCDR2 domain having an amino acid sequence selected from the group consisting of SEQ ID NOs: 14, 30, 46, 62, 82, 102, 122 and 142.

In one embodiment, the antibody or antigen-binding fragment thereof comprises a HCVR comprising a HCDR1 domain having an amino acid sequence selected from one of SEQ ID NOs: 4, 20, 36, 52, 72, 92, 112 and 132; a HCDR2 domain having an amino acid sequence selected from one of SEQ ID NOs: 6, 22, 38, 54, 74, 94, 114 and 134; a HCDR3 domain having an amino acid sequence selected from one of SEQ ID NOs: 8, 24, 40, 56, 76, 96, 116 and 136; and a LCVR comprising a LCDR1 domain having an amino acid sequence selected from one of SEQ ID NOs: 12, 28, 44, 60, 80, 100, 120 and 140; a LCDR2 domain having an amino acid sequence selected from one of SEQ ID NOs: 14, 30, 46, 62, 82, 102, 122 and 142; and a LCDR3 domain having an amino acid sequence selected from one of SEQ ID NOs: 16, 32, 48, 64, 84, 104, 124 and 144.

In certain embodiments, the human antibody or antigen-binding fragment of a human antibody that binds to human GCGR comprises a HCDR3/LCDR3 amino acid sequence pair selected from the group consisting of SEQ ID NOs: 8/16, 24/32, 40/48, 56/64, 76/84, 96/104, 116/124 and 136/144. Non-limiting examples of anti-GCGR antibodies having these HCDR3/LCDR3 pairs are the antibodies designated H4H1345N, H4H1617N, H4H1765N, H4H1321B and H4H1321P, H4H1327B and H4H1327P, H4H1328B and H4H1328P, H4H1331B and H4H1331P, H4H1339B and H4H1339P, respectively.

In one embodiment, the human antibody or antigen binding fragment thereof comprises the HCDR1, HCDR2 and HCDR3 amino acid sequences of SEQ ID NOs: 4, 6 and 8, respectively and LCDR1, LCDR2 and LCDR3 amino acid sequences of SEQ ID NOs: 12, 14 and 16, respectively.

In one embodiment, the human antibody or antigen binding fragment thereof comprises the HCDR1, HCDR2 and HCDR3 amino acid sequences of SEQ ID NOs: 20, 22 and 24, respectively and LCDR1, LCDR2 and LCDR3 amino acid sequences of SEQ ID NOs: 28, 30 and 32, respectively.

In one embodiment, the human antibody or antigen binding fragment thereof comprises the HCDR1, HCDR2 and HCDR3 amino acid sequences of SEQ ID NOs: 36, 38 and 40, respectively and LCDR1, LCDR2 and LCDR3 amino acid sequences of SEQ ID NOs: 44, 46 and 48, respectively.

In one embodiment, the human antibody or antigen binding fragment thereof comprises the HCDR1, HCDR2 and HCDR3 amino acid sequences of SEQ ID NOs: 52, 54 and 56, respectively and LCDR1, LCDR2 and LCDR3 amino acid sequences of SEQ ID NOs: 60, 62 and 64, respectively.

In one embodiment, the human antibody or antigen binding fragment thereof comprises the HCDR1, HCDR2 and HCDR3 amino acid sequences of SEQ ID NOs: 72, 74 and 76, respectively and LCDR1, LCDR2 and LCDR3 amino acid sequences of SEQ ID NOs: 80, 82 and 84, respectively.

In one embodiment, the human antibody or antigen binding fragment thereof comprises the HCDR1, HCDR2 and HCDR3 amino acid sequences of SEQ ID NOs: 92, 94 and 96, respectively and LCDR1, LCDR2 and LCDR3 amino acid sequences of SEQ ID NOs: 100, 102 and 104, respectively.

In one embodiment, the human antibody or antigen binding fragment thereof comprises the HCDR1, HCDR2 and HCDR3 amino acid sequences of SEQ ID NOs: 112, 114 and 116, respectively and LCDR1, LCDR2 and LCDR3 amino acid sequences of SEQ ID NOs: 120, 122 and 124, respectively.

In one embodiment, the human antibody or antigen binding fragment thereof comprises the HCDR1, HCDR2 and HCDR3 amino acid sequences of SEQ ID NOs: 132, 134 and 136, respectively and LCDR1, LCDR2 and LCDR3 amino acid sequences of SEQ ID NOs: 140, 142 and 144, respectively.

In one embodiment, the anti-hGCGR antibody or antigen binding fragment thereof comprises a HCDR1 sequence comprising the formula $X^1$-$X^2$-$X^3$-$X^4$-$X^5$-$X^6$-$X^7$-$X^8$ (SEQ ID NOs: 202), wherein $X^1$ is Gly, $X^2$ is Phe, $X^3$ is Thr, $X^4$ is Phe or Ser, $X^5$ is Ser, $X^6$ is Ser or Asn, $X^7$ is Tyr or Phe, and $X^8$ is Asp, Leu, or Gly; a HCDR2 sequence comprising the formula $X^1$-$X^2$-$X^3$-$X_4$-$X^5$-$X^6$-$X^7$-$X^8$ (SEQ ID NOs: 203), wherein $X^1$ is Ile, $X^2$ is Ser, Gln, Asp, or Trp, $X^3$ is Ser, Glu, Thr, or Phe, $X^4$ is Asp or Ala, $X^5$ is Gly or Glu, $X^6$ is Arg, Ile, or absent, $X^7$ is Asp or Glu, and $X^8$ is Lys or Thr; a HCDR3 sequence comprising the formula $X^1$-$X^2$-$X^3$-$X_4$-$X^5$-$X^6$-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$-$X^{19}$-$X^{20}$-$X^{21}$ (SEQ ID NOs: 204), wherein $X^1$ is Ala or Thr, $X^2$ is Lys or Arg, $X^3$ is Glu, $X^4$ is Met, Pro, Gly, or Asp, $X^5$ is Val, Ser, Lys, Arg, or absent, $X^6$ is Tyr, His, Asn, or absent, $X^7$ is Tyr, $X^8$ is Asp or Glu, $X^9$ is Ile, $X^{10}$ is Leu, $X^{11}$ is Thr, $X^{12}$ is Gly, $X^{13}$ is Tyr, Asp, or His, $X^{14}$ is His, Asp, Tyr, or absent, $X^{15}$ is Asn, Tyr, His, or absent, $X^{16}$ is Tyr, $X^{17}$ is Tyr or His, $X^{18}$ is Gly or Ala, $X^{19}$ is Met, $X^{20}$ is Asp and $X^{21}$ is Val or Ile; a LCDR1 sequence comprising the formula $X^1$-$X^2$-$X^3$-$X^4$-$X^5$-$X^6$ (SEQ ID NOs: 205), wherein $X^1$ is Gln, $X^2$ is Gly or Ala, $X^3$ is Ile, $X^4$ is Asn or Arg, $X^5$ is Asn, and $X^6$ is Tyr or Asp; a LCDR2 sequence comprising the formula $X^1$-$X^2$-$X^3$ (SEQ ID NOs: 206), wherein $X^1$ is Thr or Ala, $X^2$ is Ala or Thr, and $X^3$ is Ser or Phe; and a LCDR3 sequence comprising the formula $X^1$-$X^2$-$X^3$-$X_4$-$X^5$-$X^6$-$X^7$-$X^8$-$X^9$ (SEQ ID NOs: 207), wherein $X^1$ is Gln or Leu, $X^2$ is Gln, $X^3$ is Tyr, His, or Asp, $X^4$ is Asn or Tyr, $X^5$ is Thr or Ser, $X^6$ is Tyr, Asn, or His, $X^7$ is Pro, $X^8$ is Leu, Phe, Arg, or absent and $X^9$ is Thr.

In one embodiment, the antibody or antigen-binding fragment binds human, monkey, mouse and rat GCGR.

In one embodiment, the antibody or antigen-binding fragment binds human, monkey and mouse GCGR, but does not bind rat GCGR.

In one embodiment, the antibody or antigen-binding fragment binds human, monkey and rat GCGR, but does not bind mouse GCGR.

In one embodiment, the antibody or antigen-binding fragment binds human and monkey GCGR, but does not bind rat or mouse GCGR.

In one embodiment, the antibody or antigen-binding fragment binds human GCGR, but does not bind monkey, mouse or rat GCGR.

In one embodiment, the invention provides a fully human monoclonal antibody or antigen-binding fragment thereof that neutralizes hGCGR activity, wherein the antibody or fragment thereof exhibits one or more of the following characteristics: (i) comprises a HCVR having an amino acid sequence selected from the group consisting of SEQ ID NOs: 2, 18, 34, 50, 66, 70, 86, 90, 106, 110, 126, 130 and 146; (ii) comprises a LCVR having an amino acid sequence selected from the group consisting of SEQ ID NOs: 10, 26, 42, 58, 68, 78, 88, 98, 108, 118, 128, 138 and 148; (iii) comprises a HCDR3 domain having an amino acid sequence selected from the group consisting of SEQ ID NOs: 8, 24, 40, 56, 76, 96, 116 and 136, or a substantially similar sequence thereof having at least 90%, at least 95%, at least 98% or at least 99% sequence identity; and a LCDR3 domain having an amino acid sequence selected from the group consisting of SEQ ID NOs: 16, 32, 48, 64, 84, 104, 124 and 144, or a substantially similar sequence thereof having at least 90%, at least 95%, at least 98% or at least 99% sequence identity; (iv) comprises a HCDR1 domain having an amino acid sequence selected from the group consisting of SEQ ID NOs: 4, 20, 36, 52, 72, 92, 112 and 132, or a substantially similar sequence thereof having at least 90%, at least 95%, at least 98% or at least 99% sequence identity; a HCDR2 domain having an amino acid sequence selected from the group consisting of SEQ ID NOs: 6, 22, 38, 54, 74, 94, 114 and 134, or a substantially similar sequence thereof having at least 90%, at least 95%, at least 98% or at least 99% sequence identity; a LCDR1 domain having an amino acid sequence selected from the group consisting of SEQ ID NOs: 12, 28, 44, 60, 80, 100, 120 and 140, or a substantially similar sequence thereof having at least 90%, at least 95%, at least 98% or at least 99% sequence identity; and a LCDR2 domain having an amino acid sequence selected from the group consisting of SEQ ID NOs: 14, 30, 46, 62, 82, 102, 122 and 142, or a substantially similar sequence thereof having at least 90%, at least 95%, at least 98% or at least 99% sequence identity; (v) binds any one or more of human, monkey, mouse or rat GCGR; (vi) may or may not block GCGR activity in at least one species other than human; (v) demonstrates a $K_D$ ranging from about $10^{-8}$ to about $10^{-12}$; (vi) lowers blood glucose levels by at least about 25% to about 75% in a mammal experiencing elevated blood glucose levels; (vii) may or may not lower triglyceride levels to levels observed in a normal mammal; or (viii) demonstrates no adverse effect on blood levels of LDL, HDL, or total cholesterol in a mammal.

In another related embodiment, the invention provides an antibody or antigen-binding fragment thereof that competes for specific binding to hGCGR with an antibody or antigen-binding fragment comprising the complementarity determining regions (CDRs) of a heavy chain variable region (HCVR), wherein the HCVR has an amino acid sequence selected from the group consisting of SEQ ID NOs: 2, 18, 34, 50, 66, 70, 86, 90, 106, 110, 126, 130 and 146; and the CDRs of a light chain variable region (LCVR), wherein the LCVR has an amino acid sequence selected from the group consisting of SEQ ID NOs: 10, 26, 42, 58, 68, 78, 88, 98, 108, 118, 128, 138 and 148.

In one embodiment, the invention provides an antibody or antigen-binding fragment thereof that competes for specific binding to hGCGR with an antibody or antigen-binding fragment comprising heavy and light chain CDR domains contained within heavy and light chain sequence pairs selected from the group consisting of SEQ ID NOs: 2/10, 18/26, 34/42, 50/58, 66/68, 70/78, 86/88, 90/98, 106/108, 110/118, 126/128, 130/138 and 146/148.

In another related embodiment the invention provides an antibody or antigen-binding fragment thereof that binds the same epitope on hGCGR as an antibody or antigen-binding fragment comprising the complementarity determining regions (CDRs) of a heavy chain variable region (HCVR), wherein the HCVR has an amino acid sequence selected from the group consisting of SEQ ID NOs: 2, 18, 34, 50, 66, 70, 86, 90, 106, 110, 126, 130 and 146; and the CDRs of a light chain variable region (LCVR), wherein the LCVR has an amino acid sequence selected from the group consisting of SEQ ID NOs: 10, 26, 42, 58, 68, 78, 88, 98, 108, 118, 128, 138 and 148.

In one embodiment, the invention provides an antibody or antigen-binding fragment thereof that binds the same epitope on hGCGR that is recognized by an antibody comprising heavy and light chain sequence pairs selected from the group consisting of SEQ ID NOs: 2/10, 18/26, 34/42, 50/58, 66/68, 70/78, 86/88, 90/98, 106/108, 110/118, 126/128, 130/138 and 146/148.

In one embodiment, the invention provides for an anti-hGCGR antibody having one or more of the following characteristics:
a) capable of reducing blood glucose levels by about 25% to about 75% for a period of at least 7 days, when administered at a dose ranging from about 1 mg/kg to about 30 mg/kg;
b) capable of resulting in at least a 10% reduction in body weight when administered to a mammal in need of such therapy;
c) capable of reducing blood ketone levels by about 25% to 75% when administered at a dose ranging from about 1 mg/kg to about 30 mg/kg; or
d) capable of reducing blood glucose levels by about 20% to about 40% without causing a significant elevation in blood lipids or cholesterol when administered with an antibody specific for proprotein convertase subtilisin/kexin type (PCSK)-9, and sustaining lowered blood glucose levels for at least 7 days post treatment.

In a second aspect, the invention provides nucleic acid molecules encoding anti-hGCGR antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NOs: 1, 17, 33, 49, 65, 69, 85, 89, 105, 109, 125, 129 and 145, or a substantially identical sequence having at least 90%, at least 95%, at least 98%, or at least 99% homology thereof. In one embodiment, the HCVR is encoded by a nucleic acid sequence selected from the group consisting of SEQ ID NOs: 33, 69, 85, 109 and 125.

In one embodiment, the antibody or fragment thereof further comprises a LCVR encoded by a nucleic acid sequence selected from the group consisting of SEQ ID NOs: 9, 25, 41, 57, 67, 77, 87, 97, 107, 117, 127, 137 and 147, or a substantially identical sequence having at least 90%, at least 95%, at least 98%, or at least 99% homology thereof. In one embodiment, the LCVR is encoded by a nucleic acid sequence selected from the group consisting of SEQ ID NOs: 41, 77, 87, 117 and 127.

In one embodiment, the invention also provides an antibody or antigen-binding fragment of an antibody comprising a HCDR3 domain encoded by a nucleotide sequence selected from the group consisting of SEQ ID NOs: 7, 23, 39, 55, 75, 95, 115 and 135, or a substantially similar sequence thereof having at least 90%, at least 95%, at least 98% or at least 99% sequence identity; and a LCDR3 domain encoded by a nucleotide sequence selected from the group consisting of SEQ ID NOs: 15, 31, 47, 63, 83, 103, 123 and 143, or a substantially similar sequence thereof having at least 90%, at least 95%, at least 98% or at least 99% sequence identity.

In one embodiment, the invention provides an antibody or fragment thereof further comprising a HCDR1 domain encoded by a nucleotide sequence selected from the group consisting of SEQ ID NOs: 3, 19, 35, 51, 71, 91, 111 and 131, or a substantially similar sequence thereof having at least 90%, at least 95%, at least 98% or at least 99% sequence identity; a HCDR2 domain encoded by a nucleotide sequence selected from the group consisting of SEQ ID NOs: 5, 21, 37, 53, 73, 93, 113 and 133, or a substantially similar sequence thereof having at least 90%, at least 95%, at least 98% or at least 99% sequence identity; a LCDR1 domain encoded by a nucleotide sequence selected from the group consisting of SEQ ID NOs: 11, 27, 43, 59, 79, 99, 119 and 139, or a substantially similar sequence thereof having at least 90%, at least 95%, at least 98% or at least 99% sequence identity; and a LCDR2 domain encoded by a nucleotide sequence selected from the group consisting of SEQ ID NOs: 13, 29, 45, 61, 81, 101, 121 and 141, or a substantially similar sequence thereof having at least 90%, at least 95%, at least 98% or at least 99% sequence identity.

In a third aspect, the invention features a human anti-hGCGR antibody or antigen-binding fragment of an antibody comprising a HCVR encoded by nucleotide sequence segments derived from $V_H$, $D_H$ and $J_H$ germline sequences, and a LCVR encoded by nucleotide sequence segments derived from $V_K$ and $J_K$ germline sequences, with combinations as shown in Table 2.

The invention encompasses anti-hGCGR antibodies having a modified glycosylation pattern. In some applications, modification to remove undesirable glycosylation sites may be useful, or e.g., removal of a fucose moiety to increase antibody dependent cellular cytotoxicity (ADCC) function (see Shield et al. (2002) JBC 277:26733). In other applications, modification of galactosylation can be made in order to modify complement dependent cytotoxicity (CDC).

In a fourth aspect, the invention features a pharmaceutical composition comprising a recombinant human antibody or fragment thereof, which specifically binds hGCGR, and a pharmaceutically acceptable carrier or diluent.

In one embodiment, the invention features a composition, which is a combination of an antibody or antigen-binding fragment of an antibody of the invention, and a second therapeutic agent. The second therapeutic agent may be any agent that is advantageously combined with the antibody or fragment thereof of the invention.

In one embodiment, the second therapeutic agent may be an agent capable of lowering blood glucose or reducing at least one symptom in a patient suffering from a disease or condition characterized by high blood glucose levels, such as diabetes mellitus.

In certain embodiments, the second therapeutic agent may be an agent that helps to counteract or reduce any possible side effect(s) associated with the antibody or antigen-binding fragment of an antibody of the invention, if such side effect(s) should occur. For example, in the event that any of the anti-hGCGR antibodies increases lipid or cholesterol levels, it may be beneficial to administer a second agent that is effective to lower lipid or cholesterol levels.

The second therapeutic agent may be a small molecule drug, a protein/polypeptide, an antibody, a nucleic acid molecule, such as an anti-sense molecule, or a siRNA. The second therapeutic agent may be synthetic or naturally derived.

In one embodiment, the second therapeutic agent may be a glucagon antagonist, or a second glucagon receptor antagonist, such as another antibody to the glucagon receptor, which is different than the antibodies described herein. It will also be appreciated that the antibodies and pharmaceutically acceptable compositions of the present invention can be employed in combination therapies, that is, the antibodies and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an antibody may be administered concurrently with another agent used to treat the same disorder), or they may achieve different effects (e.g., control of any adverse effects). As used herein, additional therapeutic agents that are normally administered to treat or prevent a particular disease, or condition, are appropriate for the disease, or condition, being treated.

In one embodiment, the anti-hGCGR antibodies of the invention may be used in combination with one or more of the following type 2 diabetes treatments currently available. These include biguanide (metformin), sulfonylureas (such as glyburide, glipizide), peroxisome proliferator-activated receptor (PPAR) gamma agonists (pioglitazone, rosiglitazone); and alpha glucosidase inhibitors (acarbose, voglibose). Additional treatments include injectable treatments such as EXENATIDE® (glucagon-like peptide 1), and SYMLIN® (pramlintide).

In certain embodiments, the composition may include a second agent selected from the group consisting of non-sulfonylurea secretagogues, insulin, insulin analogs, exendin-4 polypeptides, beta 3 adrenoceptor agonists, PPAR agonists, dipeptidyl peptidase IV inhibitors, statins and statin-containing combinations, inhibitors of cholesterol uptake and/or bile acid re-absorption, LDL-cholesterol antagonists, cholesteryl ester transfer protein antagonists, endothelin receptor antagonists, growth hormone antagonists, insulin sensitizers, amylin mimetics or agonists, cannabinoid receptor antagonists, glucagon-like peptide-1 agonists, melanocortins, melanin-concentrating hormone receptor agonists, SNRIs, a fibroblast growth factor 21 (FGF21) mimetic (See, for example, US20110002845 and US20080261236), a fibroblast growth factor receptor 1c (FGFR1c) agonist (See, for example, US20110150901), an inhibitor of advanced glycation endproduct formation, such as, but not limited to, aminoguanidine, and protein tyrosine phosphatase inhibitors.

In certain embodiments, the composition may include a second agent to help lower lipid or cholesterol levels and may include an agent such as a 3-hydroxy-3-methylglutaryl-coenzyme A (HMG-COA) reductase inhibitor (for example, a statin such as atorvastatin, (LIPITOR®), fluvastatin (LESCOL®), lovastatin (MEVACOR®), pitavastatin (LIVALO®), pravastatin (PRAVACHOL®), rosuvastatin (CRESTOR®) and simvastatin (ZOCOR®) and the like.

In certain embodiments, it may be beneficial to administer the antibodies of the invention in combination with any one or more of the following: (1) niacin, which increases lipoprotein catabolismo (2) fibrates or amphipathic carboxylic acids, which reduce low-density lipoprotein (LDL) level, improve high-density lipoprotein (HDL) and triglycerides (TG) levels, and reduce the number of non-fatal heart attacks; and (3) activators of the LXR transcription factor that plays a role in cholesterol elimination such as 22-hydroxycholesterol, or fixed combinations such as VYTORIN® (ezetimibe plus simvastatin); a statin with a bile resin (e.g., cholestyramine, colestipol, colesevelam), a fixed combination of niacin plus a statin (e.g., niacin with lovastatin); or with other lipid lowering agents such as omega-3-fatty acid ethyl esters (for example, OMACOR®). Furthermore, the second therapeutic agent can be one or more other inhibitors of glucagon or hGCGR, as well as inhibitors of other molecules, such as angiopoietin-like protein 3 (ANGPTL3), angiopoietin-like protein 4 (ANGPTL4), angiopoietin-like protein 5 (ANGPTL5), angiopoietin-like protein 6 (ANGPTL6), which are involved in lipid metabolism, in particular, cholesterol and/or triglyceride homeostasis. Inhibitors of these molecules include small molecules and antibodies that specifically bind to these molecules and block their activity.

In certain embodiments, it may be beneficial to administer the anti-GCGR antibodies of the invention in combination with a nucleic acid that inhibits the activity of hPCSK9, such as an antisense molecule, a double stranded RNA, or a siRNA molecule. Exemplary nucleic acid molecules that inhibit the activity of PCSK9 are described in US2011/0065644, US2011/0039914, US2008/0015162 and US2007/0173473.

In certain embodiments, it may be beneficial to administer the anti-hGCGR antibodies of the invention in combination with an antibody that specifically binds to and inhibits the activity of hPCSK9, wherein such antibody acts to lower lipid or cholesterol levels. Exemplary anti-hPCSK9 antibodies are described in US2010/0166768. The isolated antibody that specifically binds to human PCSK9, or an antigen-binding fragment thereof, may be administered at a dose ranging from about 0.01 mg/kg to about 30 mg/kg. It may be administered as a single dose or as multiple doses. The anti-hPCSK9 antibody may be administered concurrently with the anti-GCGR antibody, or it may be administered prior to, or after the anti-GCGR antibody.

In one embodiment, the second therapeutic agent to be used in combination with an antibody of the invention comprises an isolated antibody that specifically binds to human PCSK9, or an antigen-binding fragment thereof, wherein the anti-hPCSK9 antibody comprises the three heavy chain CDRs (HCDR1, HCDR2 and HCDR3) contained within any one of the HCVR sequences selected from the group consisting of SEQ ID NOs: 173 and 177; and the three light chain CDRs (LCDR1, LCDR2 and LCDR3) contained within any one of the LCVR sequences selected from the group consisting of SEQ ID NOs: 175 and 185.

In one embodiment, the isolated antibody that specifically binds to human PCSK9, or antigen-binding fragment thereof, comprises a heavy chain variable region (HCVR) selected from the group consisting of SEQ ID NOs: 173 and 177.

In one embodiment, the isolated antibody that specifically binds to human PCSK9, or antigen-binding fragment thereof, comprises a light chain variable region (LCVR) selected from the group consisting of SEQ ID NOs: 175 and 185.

In one embodiment, the isolated antibody that specifically binds to human PCSK9, or antigen-binding fragment thereof, comprises a HCVR having an amino acid sequence selected from the group consisting of SEQ ID NOs: 173 and 177 and a LCVR having an amino acid sequence selected from the group consisting of SEQ ID NOs: 175 and 185.

In one embodiment, the isolated antibody that specifically binds to human PCSK9, or antigen-binding fragment thereof, comprises a heavy chain variable region (HCVR) and a light chain variable region (LCVR), wherein the HCVR/LCVR sequence pairs are selected from the group consisting of SEQ ID NOs: 173/175; and SEQ ID NOs: 177/185.

In one embodiment, the isolated antibody that specifically binds to human PCSK9, or antigen-binding fragment thereof, comprises: a HCDR1 comprising an amino acid sequence selected from the group consisting of SEQ ID NOs: 161 and 179; a HCDR2 comprising an amino acid sequence selected from the group consisting of SEQ ID NOs: 163 and 181; a HCDR3 comprising an amino acid sequence selected from the group consisting of SEQ ID NOs: 165 and 183; a LCDR1 comprising an amino acid sequence selected from the group consisting of SEQ ID NOs: 167 and 187; a LCDR2 comprising an amino acid sequence selected from the group consisting of SEQ ID NOs: 169 and 189 and a LCDR3 comprising an amino acid sequence selected from the group consisting of SEQ ID NOs: 171 and 191.

In certain embodiments, the hPCSK9 antibodies to be used in combination with the anti-GCGR antibodies of the invention are encoded by nucleic acid molecules as described herein. For example, in one embodiment, the invention provides an anti-hPCSK9 antibody or fragment thereof comprising a HCVR encoded by a nucleic acid sequence selected from the group consisting of SEQ ID NOs: 172 and 176, or a substantially identical sequence having at least 90%, at least 95%, at least 98%, or at least 99% homology thereof, and a LCVR encoded by a nucleic acid sequence selected from the group consisting of SEQ ID NOs: 174 and 184, or a substantially identical sequence having at least 90%, at least 95%, at least 98%, or at least 99% homology thereof.

In one embodiment, the invention provides an anti-hPCSK9 antibody to be used in combination with the anti-GCGR antibodies of the invention, wherein the anti-PCSK9 antibody or fragment thereof comprises a HCDR1 domain encoded by a nucleotide sequence selected from the group consisting of SEQ ID NOs: 160 and 178, or a substantially similar sequence thereof having at least 90%, at least 95%, at least 98% or at least 99% sequence identity; a HCDR2 domain encoded by a nucleotide sequence selected from the group consisting of SEQ ID NOs: 162 and 180, or a substantially similar sequence thereof having at least 90%, at least 95%, at least 98% or at least 99% sequence identity; a HCDR3 domain encoded by a nucleotide sequence selected from the group consisting of SEQ ID NOs: 164 and 182, or a substantially similar sequence thereof having at least 90%, at least 95%, at least 98% or at least 99% sequence identity; a LCDR1 domain encoded by a nucleotide sequence selected from the group consisting of SEQ ID NOs: 166 and 186, or a substantially similar sequence thereof having at least 90%, at least 95%, at least 98% or at least 99% sequence identity; a LCDR2 domain encoded by a nucleotide sequence selected from the group consisting of SEQ ID NOs: 168 and 188, or a substantially similar sequence thereof having at least 90%, at least 95%, at least 98% or at least 99% sequence identity; and a LCDR3 domain encoded by a nucleotide sequence selected from the group consisting of SEQ ID NOs: 170 and 190, or a substantially similar sequence thereof having at least 90%, at least 95%, at least 98% or at least 99% sequence identity.

When multiple therapeutics are co-administered, dosages may be adjusted accordingly, as is recognized in the pertinent art.

In a fifth aspect, the invention features methods for inhibiting hGCGR activity using the anti-hGCGR antibody or antigen-binding portion of the antibody of the invention, wherein the therapeutic methods comprise administering a therapeutically effective amount of a pharmaceutical composition comprising the antibody or antigen-binding fragment thereof. The antibodies of the invention may be used to treat any condition or disorder, which is improved, ameliorated, inhibited or prevented by removal, inhibition or reduction of hGCGR activity. It is envisioned that the antibodies of the invention may be used alone, or as adjunct therapy with other agents or methods known to be standard care for treating patients suffering from diseases or conditions characterized in part by elevated blood glucose or ketone levels, such as, but not limited to, diabetes. Such standard therapy may include fluid administration, or administration of any other pharmaceutical agents useful for lowering blood glucose, ketones, or lipids, or for weight reduction.

The anti-hGCGR antibodies of the invention may function to block the interaction between glucagon and its receptor, thereby inhibiting the glucose elevating effects of glucagon. The use of glucagon receptor antagonists, such as the antibodies described herein, may be an effective means of achieving normal levels of glucose, thereby ameliorating, or preventing one or more symptoms of, or long term complications associated with, for example, diabetes. The use of glucagon receptor antagonists, such as the antibodies described herein, may also be an effective means of achieving normal levels of glucose in non-diabetic patients, who experience hyperglycemia as a result of conditions or disorders not related to diabetes, such as perioperative hyperglycemia (hyperglycemia observed in patients just prior to surgery, or after surgery). In certain embodiments, methods of lowering blood glucose levels or ketone levels in diabetic ketoacidosis are envisioned using the antibodies of the invention. In certain embodiments, methods of treating patients to achieve a reduction in body weight, or to prevent weight gain, or to maintain a normal body weight, are also envisioned using the antibodies of the invention.

The antibodies of the present invention may be useful for ameliorating conditions such as, for example, impaired glucose tolerance, obesity, or for preventing weight gain, or for treating diabetic conditions, or for preventing or reducing the severity of any one or more of the long-term complications associated with diabetes, such as nephropathy, neuropathy, retinopathy, cataracts, stroke, atherosclerosis, impaired wound healing and other complications associated with diabetes, known to those skilled in the art.

Other conditions or disorders treatable by the therapeutic methods of the invention include diabetic ketoacidosis, hyperglycemia (including perioperative hyperglycemia, hyperglycemia in the intensive care unit patient, and hyperosmolar hyperglycemia syndrome), hyperinsulinemia, the metabolic syndrome, insulin resistance syndrome, impaired fasting glucose, or hyperglycemia associated with hypercholesterolemia, hypertriglyceridemia, hyperlipidemia, and general dyslipidemias.

The antibodies may also be useful for treating patients with inoperable glucagonoma (pancreatic endocrine tumor with or without necrolytic migratory erythema and hyperglycemia).

Other embodiments will become apparent from a review of the ensuing detailed description.

DETAILED DESCRIPTION

Figure 1:
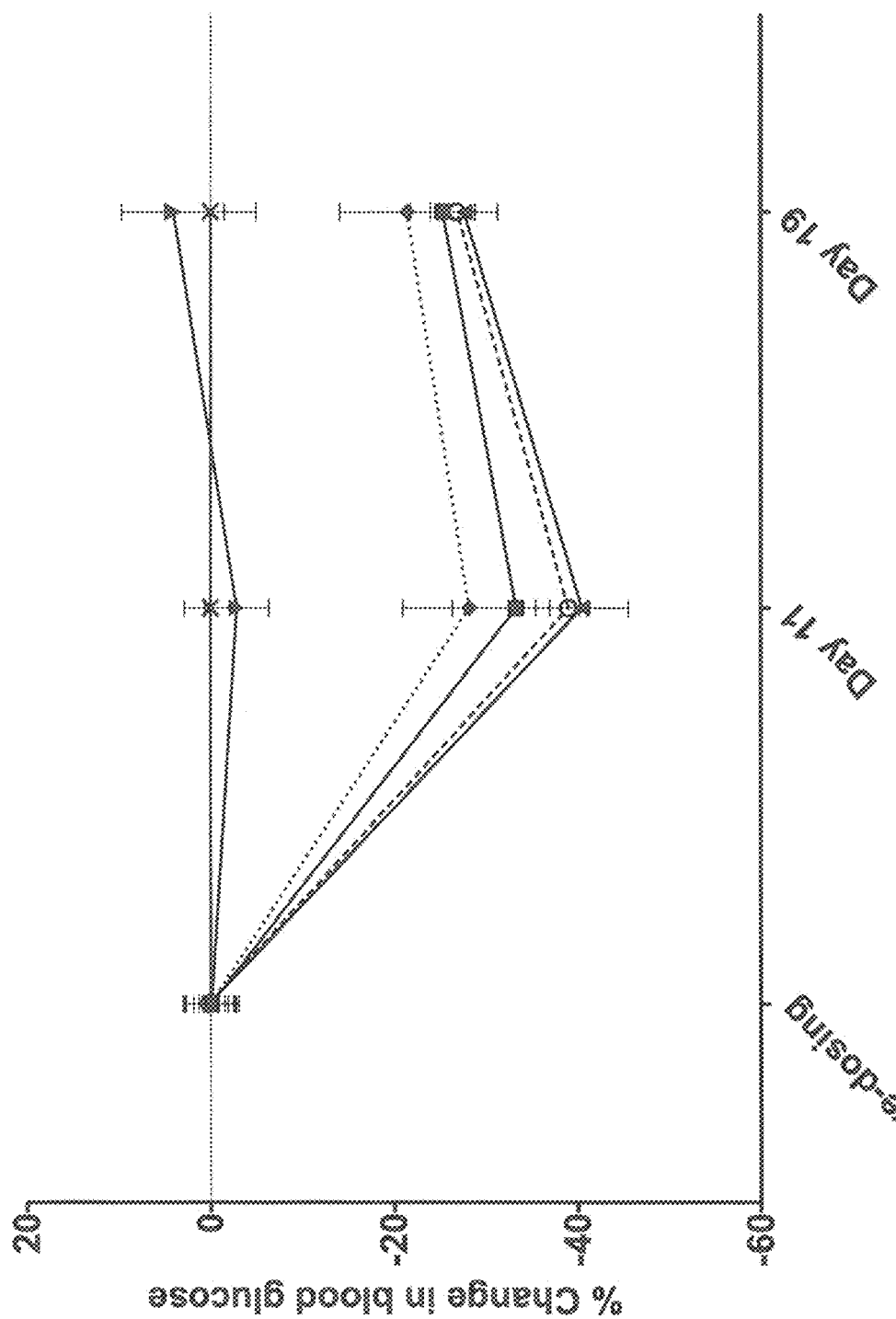
FIG. 1 shows the percent change in blood glucose levels in C57BL6 mice after administration of H4H1327P (anti-GCGR antibody), and/or H1H316P (anti-PCSK9 antibody) when given alone or in combination. Control (X with solid line); H4H1327P at 3 mg/kg (■ with solid line); H4H1327P at 10 mg/kg (▲ with solid line); H1H316P at 10 mg/kg (♦ with solid line); H4H1327P at 3 mg/kg+H1H316P at 10 mg/kg (♦ with dashed line); H4H1327P at 10 mg/kg+H1H316P at 10 mg/kg (○ with dashed lines).

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

Definitions

The "glucagon receptor", also referred to herein as "GCGR", belongs to the G protein-coupled receptor class 2 family and consists of a long amino terminal extracellular domain (See SEQ ID NO: 158 for DNA encoding the N-terminal extracellular domain and SEQ ID NO: 159 for the amino acid sequence of the N-terminal extracellular domain), seven transmembrane segments, and an intracellular C-terminal domain (Jelinek et al., Science 259:1614-1616 (1993), Segre et al., Trends Endocrinol. Metab 4:309-314 (1993)). Glucagon receptors are notably expressed on the surface of hepatocytes where they bind to glucagon and transduce the signal provided thereby into the cell. Accordingly, the term "glucagon receptor" also refers to one or more receptors that interact specifically with glucagon to result in a biological signal. DNA sequences encoding glucagon receptors of rat and human origin have been isolated and disclosed in the art (EP0658200B1). The murine and cynomolgus monkey homologues have also been isolated and sequenced (Burcelin, et al., Gene 164 (1995) 305-310); McNally et al., Peptides 25 (2004) 1171-1178). As used herein, "glucagon receptor" and "GCGR" are used interchangeably. The expression "GCGR", "hGCGR" or fragments thereof, as used herein, refers to the human GCGR protein or fragment thereof, unless specified as being from a non-human species, e.g. "mouse GCGR", "rat GCGR", or "monkey GCGR". Moreover, "GCGR," or "hGCGR", as used herein, refers to human GCGR having the nucleic acid sequence shown in SEQ ID NO: 157 and the amino acid sequence of SEQ ID NO: 153, or a biologically active fragment thereof. There are a variety of sequences related to the GCGR gene having the following Genbank Accession Numbers: NP_000151.1 (human), NP_742089.1 (rat), XP_001111894.1 (rhesus monkey), and NP_032127.2 (mouse). Other sequences disclosed herein include human GCGR (SEQ ID NO: 153), mouse GCGR (SEQ ID NO: 154), Cynomolgus monkey (SEQ ID NO: 155), rat GCGR (SEQ ID NO: 156). In certain embodiments, fusion proteins useful in the invention may include SEQ ID NO: 149 (hGCGR-hFc, residues 27-144 of NP_000151.1 fused to the Fc region of human IgG) SEQ ID NO:150 (hGCGR-hFc, residues 27-144 of NP_000151.1 fused to the Fc region of human IgG), SEQ ID NO: 151 (hGCGR-mmH, residues 27-144 of NP_000151.1 fused to a myc-myc-his tag), and SEQ ID NO: 152 (MfGCGR-hFc, containing the N-terminal sequence of Mf, cynomolgus monkey, which is identical to residues 27-144 of GCGR of the rhesus monkey, *Macaca mulatta*, having accession number XP_001111894.1, and which is fused to the Fc region of human IgG). The nucleic acid sequences, the polypeptides encoded by them, and other nucleic acid and polypeptide sequences are herein incorporated by reference in their entireties as well as for individual subsequences contained therein.

The term "human proprotein convertase subtilisin/kexin type 9" or "hPCSK9", as used herein, refers to hPCSK9 encoded by the nucleic acid sequence shown in SEQ ID NO:192 and having the amino acid sequence of SEQ ID NO:193, or a biologically active fragment thereof.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the anti-GCGR antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully-human anti-GCGR antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-hGCGR antibodies comprising variants of any of the HCVR, LCVR, and/or CDR amino acid sequences disclosed herein having one or more conservative substitutions. For example, the present invention includes anti-hGCGR antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The anti-human GCGR antibodies of the invention may be designated as "anti-hGCGR" or "anti-GCGR".

The term "specifically binds," or the like, means that an antibody or antigen-binding fragment thereof forms a complex with an antigen that is relatively stable under physiologic conditions. Specific binding can be characterized by an equilibrium dissociation constant of at least about $1\times10^{-6}$ M or less (e.g., a smaller $K_D$ denotes a tighter binding). Methods for determining whether two molecules specifically bind are well known in the art and include, for example, equilibrium dialysis, surface plasmon resonance, and the like. An isolated antibody that specifically binds hGCGR may, however, exhibit cross-reactivity to other antigens such as GCGR molecules from other species. Moreover, multi-specific antibodies that bind to hGCGR and one or more additional antigens or a bi-specific that binds to two different regions of hGCGR are nonetheless considered antibodies that "specifically bind" hGCGR, as used herein.

The term "high affinity" antibody refers to those mAbs having a binding affinity to hGCGR, expressed as $K_D$, of at least $10^{-9}$ M; preferably $10^{-10}$ M; more preferably $10^{-11}$ M, even more preferably $10^{-12}$ M, as measured by surface plasmon resonance, e.g., BIACORE™ or solution-affinity ELISA.

By the term "slow off rate", "Koff" or "kd" is meant an antibody that dissociates from hGCGR with a rate constant of $1\times10^{-3}$ s$^{-1}$ or less, preferably $1\times10^{-4}$ s$^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding portion" of an antibody, or "antibody fragment", as used herein, refers to one or more fragments of an antibody that retain the ability to specifically bind to hGCGR.

The specific embodiments, antibody or antibody fragments of the invention may be conjugated to a therapeutic moiety ("immunoconjugate"), such as a second GCGR antagonist, or to biguanide (metformin), a sulfonylurea (such as glyburide, glipizide), a PPAR gamma agonist (such as pioglitazone, or rosiglitazone), an alpha glucosidase inhibitor (such as acarbose, or voglibose), EXENATIDE® (glucagon-like peptide 1), SYMLIN® (pramlintide), a chemotherapeutic agent, a radioisotope, or any other therapeutic moiety useful for treating a disease or condition caused in part by unwanted glucagon activity.

An "isolated antibody", as used herein, is intended to refer to an antibody that is substantially free of other antibodies (Abs) having different antigenic specificities (e.g., an isolated antibody that specifically binds hGCGR, or a fragment thereof, is substantially free of Abs that specifically bind antigens other than hGCGR).

A "blocking antibody" or a "neutralizing antibody", as used herein (or an "antibody that neutralizes GCGR activity"), is intended to refer to an antibody whose binding to hGCGR results in inhibition of at least one biological activity of GCGR. For example, an antibody of the invention may aid in preventing the increase in blood glucose levels associated with elevation of glucagon levels. Alternatively, an antibody of the invention may demonstrate the ability to block cAMP production in response to glucagon. This inhibition of the biological activity of GCGR can be assessed by measuring one or more indicators of GCGR biological activity by one or more of several standard in vitro or in vivo assays known in the art (see examples below).

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24:307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256:1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403 410 and (1997) Nucleic Acids Res. 25:3389 402, each of which is herein incorporated by reference.

In specific embodiments, the antibody or antibody fragment for use in the method of the invention may be monospecific, bi-specific, or multi-specific. Multi-specific antibodies may be specific for different epitopes of one target polypeptide or may contain antigen-binding domains specific for epitopes of more than one target polypeptide. An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise an Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 mAbs; N44S, K52N, and V82I (IMGT; N384S, K392N, and V422I by EU) in the case of IgG2 mAbs; and Q15R, N44S, K52N, V57M, R69K, E79Q, and V82I (by IMGT; Q355R, N384S, K392N, V397M, R409K, E419Q, and V422I by EU) in the case of IgG4 mAbs. Variations on the bi-specific antibody format described above are contemplated within the scope of the present invention.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding). "Normal glucose levels" refers to mean plasma glucose values in humans of less than about 80 mg/dL for fasting levels, and about less than 110-120 mg/dL for post prandial levels. Plasma glucose may be determined in accordance with Etgen et al., (Metabolism 2000; 49 (5): 684-688) or calculated from a conversion of whole blood glucose concentration in accordance with D'Orazio et al., (Clin. Chem. Lab. Med. 2006; 44 (12): 1486-1490). "Cholesterol normalization" or "normal cholesterol levels" refers to a total cholesterol level in a human of about less than 200 mg/dl, with a range of about 200-240 mg/dL considered borderline high. From the total normal cholesterol, a mean LDL value in humans of about 100 to about 129 mg/dl is considered normal and an HDL value above 45 mg/dL is considered normal. The normal triglyceride level in humans is less than 150 mg/dL. The normal total/HDL ratio is below 4.5, and the normal LDL/HDL ratio is less than 3. These values may be determined in accordance with standard laboratory practice (see also, Friedewald, W T, Clin. Chem (1972), 18:499-502; Chen, Y. et al. Lipids Health Dis. (2010); 9:52; Keevil, J G, et al., Circulation (2007), 115: 1363-1370; and Bairaktari, E. et al., Clin. Biochem. (2000), 33:549-555). In certain embodiments of the invention, the anti-GCGR antibodies may be useful to lower blood glucose levels to within the normal range. In certain embodiments of the invention, the anti-GCGR antibodies may be useful to increase the level of HDL-C. In certain embodiments of the invention, the anti-GCGR antibodies may be useful to decrease the level of triglycerides.

General Description

Since glucagon exerts its physiological effects by signaling through the glucagon receptor, the glucagon receptor may be a potential therapeutic target for diabetes and other glucagon related metabolic disorders. The use of glucagon receptor antagonists, such as the antibodies described herein, may be an effective means of achieving normal levels of glucose, thereby ameliorating, or preventing one or more symptoms or long term complications associated with diabetes. The antibodies of the present invention may also be useful for ameliorating conditions associated with, for example, impaired glucose tolerance, for treating obesity, for preventing weight gain, for treating metabolic syndrome, or for treating diabetic conditions, including diabetic ketoacidosis, or for preventing and/or lowering the risk of developing any one or more of the complications associated with diabetes, such as nephropathy, neuropathy, retinopathy, cataracts, stroke, atherosclerosis, impaired wound healing and other complications associated with diabetes, known to those skilled in the art.

The use of the anti-hGCGR antibodies, as described herein, may also be useful for treating other conditions, including hyperglycemia, hyperglycemic hyperosmolar syndrome (Stoner, G. D., American Family Physician, (2005), 71 (9): 1723-1730; Diabetes Spectrum, Umpierrez, G. E., (2002), 15 (1): 28-36; Nugent, B. W., Emergency Medicine Clinics of North America, (2005), 23:629-648), perioperative hyperglycemia (Frisch, A. et al. Diabetes Care, (2010), 33 (8): 1783-1788; Hanazaki, K. et al. World J Gastroenterol, (2009), 15 (33): 4122-4125; Smiley, D. D. et al. Southern Medical Journal, (2006), 99 (6): 580-589; Hermanides, J. et al., The Netherlands J. of Med. 67 (6): 226-229; Maerz, L. L. et al., Current Opinion in Critical Care, (2011), 17:370-375), hyperglycemia in intensive care unit patients (Gunst, J. et al., Seminars in Dialysis, (2010), 23 (2): 157-162; Losser, M-R., Critical care, (2010), 14:231), hyperinsulinemia, and insulin resistance syndrome and glucagonoma (pancreatic endocrine tumor with or without necrolytic migratory erythema and hyperglycemia) (See for example, Boden, G. et al., N Engl J Med (1986); 314:1686-1689).

In certain embodiments, the antibodies of the invention were obtained from mice immunized with a primary immunogen, followed by immunization with a secondary immunogen. The immunogen may be a cell line expressing the GCGR protein, or a biologically active fragment thereof, or DNA encoding the GCGR protein or active fragment thereof, or the GCGR protein or active fragment thereof. For example, in certain embodiments, the primary immunogen may be a cell line engineered using standard procedures known in the art to over-express full-length hGCGR (e.g. the mouse MG87 cell line). Alternatively, DNA immunization may be performed using DNA encoding full-length hGCGR (e.g. hGCGR constructs derived from accession number NP_000151.1), or DNA encoding a biologically active fragment thereof, for example, DNA encoding the N-terminal domain of GCGR (see, for example, SEQ ID NO: 158, which encodes SEQ ID NO: 159), or a soluble N-terminal protein, including that of SEQ ID NO: 159, or the amino acids spanning residues 27-144 of SEQ ID NO: 153. The secondary immunogen may be a GCGR protein, or biologically active fragment thereof, or a fusion protein, such as hGCGR-mmH (REGN547, SEQ ID NO: 151) or hGCGR-hFc (REGN315, SEQ ID NO: 150; REGN316, SEQ ID NO: 149).

In certain embodiments of the present invention, the N-terminal domain, having the amino acid sequence shown in SEQ ID NO: 159 (without the signal sequence), or any one or more of the ectodomains of GCGR, e.g. any one or more of the extracellular regions (or fragments thereof) may be used to prepare antibodies that bind GCGR and inhibit its function, e.g. its ability to bind glucagon, which would result in lowering of blood glucose levels.

The full-length amino acid sequence of human GCGR is shown as SEQ ID NO: 153. The signal peptide spans amino acid residues 1-26 of SEQ ID NO: 153; the N-terminal domain spans residues 27-144 of SEQ ID NO: 153; extracellular region 1 (EC1) spans amino acid residues 194-226 of SEQ ID NO: 153; extracellular region 2 (EC2) spans amino acid residues 285-305 of SEQ ID NO: 153; and extracellular region 3 (EC3) spans amino acid residues 369-384 of SEQ ID NO:153.

In certain embodiments, antibodies that bind specifically to GCGR may be prepared using fragments of the above-noted extracellular regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of GCGR specific antibodies. In certain embodiments, any one or more of the above-noted regions of GCGR, or fragments thereof may be used for preparing monospecific, bispecific, or multispecific antibodies.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding portion" of an antibody, or "antibody fragment", as used herein, refers to one or more fragments of an antibody that retain the ability to specifically bind to hGCGR. An antibody fragment may include a Fab fragment, a F(ab')$_2$ fragment, a Fv fragment, a dAb fragment, a fragment containing a CDR, or an isolated CDR. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bispecific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to human GCGR.

Using VELOCIMMUNE™ technology (see, for example, U.S. Pat. No. 6,596,541, Regeneron Pharmaceuticals, VELOCIMMUNE®) or any other known method for generating monoclonal antibodies, high affinity chimeric antibodies to GCGR are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies of the instant invention possess very high affinities, typically possessing $K_D$ of from about $10^{-12}$ through about $10^{-9}$ M, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Bioequivalents

The anti-GCGR antibodies and antibody fragments of the present invention encompass proteins having amino acid sequences that vary from those of the described antibodies, but that retain the ability to bind human GCGR. Such variant antibodies and antibody fragments comprise one or more additions, deletions, or substitutions of amino acids when compared to parent sequence, but exhibit biological activity that is essentially equivalent to that of the described antibodies. Likewise, the anti-GCGR antibody-encoding DNA sequences of the present invention encompass sequences that comprise one or more additions, deletions, or substitutions of nucleotides when compared to the disclosed sequence, but that encode an anti-GCGR antibody or antibody fragment that is essentially bioequivalent to an anti-GCGR antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-GCGR antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-GCGR antibody variants comprising amino acid changes, which modify the glycosylation characteristics of the antibodies, e.g., mutations which eliminate or remove glycosylation.

Biological Characteristics of the Antibodies

In general, the antibodies of the present invention may function by binding to at least one of the extracellular regions of hGCGR. In certain embodiments, the antibodies of the present invention may bind to an epitope located in at least the N-terminal region, or to an epitope located in at least one of the extracellular (EC) loops of hGCGR.

In certain embodiments, the antibodies of the present invention may function by blocking or inhibiting GCGR activity by binding to the extracellular N-terminal region, the amino acid sequence of which is shown in SEQ ID NO: 159, and which is encoded by the nucleic acid sequence shown in SEQ ID NO: 158.

In certain embodiments, the antibodies of the present invention may function by blocking or inhibiting GCGR activity by binding to at least one of the EC loops or loop segments within the whole receptor. In one embodiment, the antibodies of the invention may bind to an epitope located in EC1, which is located between about amino acid residue 194 to about amino acid residue 226 of SEQ ID NO: 153. Alternatively, or additionally, the antibodies of the invention may bind to an epitope found in EC2, which is located between about amino acid residue 285 to about amino acid residue 302 of SEQ ID NO: 153. Alternatively, or additionally, the antibodies of the invention may bind to an epitope found in EC3, which is located between about amino acid residue 369 to about amino acid residue 384 of SEQ ID NO: 153.

In certain embodiments, the antibodies of the present invention may be bi-specific antibodies. The bi-specific antibodies of the invention may bind one epitope in EC1 and may also bind one epitope in a region of hGCGR other than EC1. In certain embodiments, the bi-specific antibodies of the invention may bind one epitope in EC1 and may also bind one epitope in EC2 or EC3, or in the N-terminal region, or in any other region within EC1, EC2, or EC3 of hGCGR, or any combination thereof. In certain embodiments, the bi-specific antibodies of the invention may bind to two different sites within the same extracellular region.

More specifically, the anti-GCGR antibodies of the invention may exhibit one or more of the following characteristics: (1) ability to bind to a human GCGR or a fragment thereof and to a non-human (e.g., mouse, monkey, rat, rabbit, dog, pig, etc.) GCGR or fragment thereof; (2) ability to bind to a human GCGR or fragment thereof, but not to a non-human (e.g., mouse, monkey, rat, rabbit, dog, pig, etc.) GCGR or fragment thereof; (3) ability to bind to a human GCGR or fragment thereof and to a non-human primate (e.g. monkey) GCGR or fragment thereof, but not to a mouse, rat, rabbit, dog or pig GCGR or GCGR fragment; (4) ability to bind to a human GCGR or fragment thereof and to a non-human primate (e.g. monkey) GCGR or a fragment thereof, and to a mouse GCGR or a fragment thereof, but not to a rat GCGR; (5) ability to bind to a human GCGR or fragment thereof and to a non-human primate (e.g. monkey) GCGR or a fragment thereof, and to a rat GCGR or a fragment thereof, but not to a mouse GCGR; 6) blocks glucagon binding to GCGR; 7) blocks glucagon induced cAMP production; 8) demonstrates the ability to lower blood glucose levels in humans suffering from diabetes and in animal models of diabetes; 9) may or may not lower triglyceride levels to the levels observed in normal mammals; or 10) does not adversely affect plasma lipid levels.

Certain anti-GCGR antibodies of the present invention are able to inhibit or attenuate GCGR activity in an in vitro or in vivo assay. The ability of the antibodies of the invention to bind to and inhibit binding of glucagon to GCGR may be measured using any standard method known to those skilled in the art, including binding assays, reporter bioassays, such as a luciferase reporter assay.

Non-limiting, exemplary in vitro assays for measuring GCGR activity are illustrated in Examples 4 and 5, herein. In Example 4, the binding affinities and kinetic constants of human anti-hGCGR antibodies were determined by surface plasmon resonance and the measurements were conducted on a T100 Biacore instrument. In Example 5, a bioassay was developed in HEK293 cell lines expressing full length human, monkey and mouse GCGR along with a luciferase reporter in order to detect activation through Gαs, and subsequent elevation of CAMP levels and transcriptional activation. Examples 6, 7, 8, 9 and 10 demonstrate the in vivo effects of the antibodies on lowering of blood glucose levels, blood ketone levels, and on weight loss, in various animal models.

The present invention also includes anti-GCGR antibodies and antigen binding fragments thereof which bind to at least one biologically active fragment of any of the following proteins, or peptides: SEQ ID NO: 153 (full length hGCGR), residue numbers 27-144 of SEQ ID NO: 153 (N-terminal domain of hGCGR); residues 194-226 of SEQ ID NO: 153; residues 285-305 of SEQ ID NO: 153; residues 369-384 of SEQ ID NO: 153. Any of the GCGR peptides described herein, or fragments thereof, may be used to generate anti-GCGR antibodies.

The peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization. The antibodies specific for GCGR may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

In one embodiment, the invention provides a fully human monoclonal antibody or antigen-binding fragment thereof that specifically binds hGCGR and neutralizes hGCGR activity, wherein the antibody or fragment thereof exhibits one or more of the following characteristics: (i) comprises a HCVR having an amino acid sequence selected from the group consisting of SEQ ID NOs: 2, 18, 34, 50, 66, 70, 86, 90, 106, 110, 126, 130, and 146; (ii) comprises a LCVR having an amino acid sequence selected from the group consisting of SEQ ID NOs: 10, 26, 42, 58, 68, 78, 88, 98, 108, 118, 128, 138, and 148; (iii) comprises any one or more of the heavy chain CDR1 sequences selected from the group consisting of 4, 20, 36, 52, 72, 92, 112 and 132; any one or more of the heavy chain CDR2 sequences selected from the group consisting of 6, 22, 38, 54, 74, 94, 114 and 134; any one or more of the heavy chain CDR3 sequences selected from the group consisting of 8, 24, 40, 56, 76, 96, 116 and 136; any one or more of the light chain CDR1 sequences selected from the group consisting of 12, 28, 44, 60, 80, 100, 120 and 140; any one or more of the light chain CDR2 sequences selected from the group consisting of 14, 30, 46, 62, 82, 102, 122 and 142; any one or more of the light chain CDR3 sequences selected from the group consisting of 16, 32, 48, 64, 84, 104, 124 and 144; and combinations thereof; (iv) demonstrates binding specificity for any one or more of the following: the N-terminal region of GCGR comprising amino acid residues 27-144 of SEQ ID NO: 153, or for any one or more of the extracellular loops of GCGR, including, for example, EC1, EC2, or EC3, wherein EC1 comprises amino acid residues ranging from about residue 194 to about residue 226 of SEQ ID NO: 153, and wherein EC2 comprises amino acid residues ranging from about residue 285 to about residue 305 of SEQ ID NO: 153; and wherein EC3 comprises amino acid residues ranging from about residue 369 to about residue 384 of SEQ ID NO: 153; (v) binds any one or more of human, monkey, mouse or rat GCGR; (vi) blocks binding of glucagon to GCGR; vi) blocks glucagon induced cAMP production; vii) demonstrates the ability to lower blood glucose levels or blood ketone levels in humans suffering from diabetes or in animal models of diabetes; viii) may or may not lower triglyceride levels to the levels observed in normal mammals; or ix) does not adversely affect plasma lipid levels.

Epitope Mapping and Related Technologies

To screen for antibodies that bind to a particular epitope, a routine cross-blocking assay such as that described *Antibodies*, Harlow and Lane (Cold Spring Harbor Press, Cold Spring Harb., NY) can be performed. Other methods include alanine scanning mutants, peptide blots (Reineke (2004) Methods Mol Biol 248:443-63) (herein specifically incorporated by reference in its entirety), or peptide cleavage analysis. In addition, methods such as epitope excision, epitope extraction and chemical modification of antigens can be employed (Tomer (2000) Protein Science 9:487-496) (herein specifically incorporated by reference in its entirety).

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the anti-GCGR antibodies of the invention into groups of antibodies binding different epitopes.

In certain embodiments, the anti-GCGR antibody or antigen-binding fragment of an antibody binds an epitope within at least one of the extracellular regions of GCGR, or to a fragment thereof, wherein the extracellular region is the N-terminal domain, or one of the EC loops, including EC1, EC2, or EC3, as described previously.

In one embodiment, the antibody binds an epitope within the N-terminal region of GCGR, or a fragment thereof, comprising an amino acid sequence ranging from about amino acid residue 27-144 of SEQ ID NO: 153. In one embodiment, the antibody binds an epitope within EC1, or a fragment thereof, comprising an amino acid sequence ranging from about amino acid residue 194-226 of SEQ ID NO: 153. In one embodiment, the antibody binds an epitope within EC2, or a fragment thereof, comprising an amino acid sequence ranging from amino acid residue 285-305 of SEQ ID NO: 153. In one embodiment, the antibody binds an epitope within EC3, or a fragment thereof, comprising an amino acid sequence ranging from about amino acid residue 369-384 of SEQ ID NO: 153.

In certain embodiments, the antibody or antibody fragment binds an epitope which includes more than one of the enumerated epitopes of GCGR within the N-terminal domain, or within EC1, EC2, or EC3, and/or within two or three different extracellular regions (for example, epitopes within the N-terminal region, EC1, EC2 and EC3 loops, or within EC1, EC2, and EC3, or within the N-terminal region, EC2 and EC3 loops, or within the N-terminal region, EC1 and EC3 loops.

In certain embodiments, the antibody is a bi-specific antibody that binds one epitope within one extracellular region of GCGR and another epitope within a different extracellular region of GCGR, including the N-terminal domain, or EC1, EC2, or EC3.

In one embodiment, the antibody is a bi-specific antibody that binds one epitope in the N-terminal region of hGCGR and another epitope in EC1 of hGCGR. In one embodiment, the antibody is a bi-specific antibody that binds one epitope in the N-terminal region of hGCGR and another epitope in EC1 of hGCGR. In one embodiment, the antibody is a bi-specific antibody that binds one epitope in the N-terminal region of hGCGR and another epitope in EC2 of hGCGR. In one embodiment, the antibody is a bi-specific antibody that binds one epitope in the N-terminal region of hGCGR and another epitope in EC3 of hGCGR. In one embodiment, the antibody is a bi-specific antibody that binds one epitope in EC1 of hGCGR and another epitope in EC2 of hGCGR. In one embodiment, the antibody is a bi-specific antibody that binds one epitope in EC1 of hGCGR and another epitope in EC3 of hGCGR. In one embodiment, the antibody is a bi-specific antibody that binds one epitope in EC2 of hGCGR and another epitope in EC3 of hGCGR.

In one embodiment, the antibody is a bi-specific antibody that binds one epitope in the N terminal domain of hGCGR, wherein the one epitope ranges from about residue 27 to about residue 144 of SEQ ID NO: 153 and a second epitope in EC1 of hGCGR, wherein the second epitope ranges from about residue number 194 to about residue number 226 of SEQ ID NO: 153. In one embodiment, the antibody is a bi-specific antibody that binds one epitope in the N terminal domain of hGCGR within the residues noted above, and a second epitope in EC2 of hGCGR, wherein the second epitope ranges from about residue number 285 to about residue number 305 of SEQ ID NO: 153. In one embodiment, the antibody is a bi-specific antibody that binds one epitope in the N terminal domain of hGCGR within the residues noted above, and a second epitope in EC3 of hGCGR, wherein the second epitope ranges from about residue number 369 to about residue number 384 of SEQ ID NO: 153.

In one embodiment, the antibody is a bi-specific antibody that binds one epitope in EC1 of hGCGR from about residue 194 to about residue 226 of SEQ ID NO: 153 and a second epitope in EC2 of GCGR from about residue 285 to about residue 305 of SEQ ID NO: 153. In one embodiment, the antibody is a bi-specific antibody that binds one epitope in EC1 from about residue 194 to about residue 226 of SEQ ID NO: 153 and a second epitope in EC3 of GCGR from about residue 369 to about residue 384 of SEQ ID NO:153. In one embodiment, the antibody is a bi-specific antibody that binds one epitope in EC2 from about residue 285 to about residue 305 of SEQ ID NO:153 and a second epitope in EC3 of GCGR from about residue 369 to about residue 384 of SEQ ID NO:153.

The present invention includes anti-GCGR antibodies that bind to the same epitope as any of the specific exemplary antibodies described herein (e.g., H4H1345N, H4H1617N, H4H1765N, H4H1321B and H4H1321P, H4H1327B and H4H1327P, H4H1328B and H4H1328P, H4H1331B and H4H1331P, H4H1339B and H4H1339P). Likewise, the present invention also includes anti-GCGR antibodies that compete for binding to GCGR or a GCGR fragment with any of the specific exemplary antibodies described herein.

One can easily determine whether an antibody binds to the same epitope as, or competes for binding with, a reference anti-GCGR antibody by using routine methods known in the art. For example, to determine if a test antibody binds to the same epitope as a reference anti-GCGR antibody of the invention, the reference antibody is allowed to bind to a GCGR protein or peptide under saturating conditions. Next, the ability of a test antibody to bind to the GCGR molecule is assessed. If the test antibody is able to bind to GCGR following saturation binding with the reference anti-GCGR antibody, it can be concluded that the test antibody binds to a different epitope than the reference anti-GCGR antibody. On the other hand, if the test antibody is not able to bind to the GCGR molecule following saturation binding with the reference anti-GCGR antibody, then the test antibody may bind to the same epitope as the epitope bound by the reference anti-GCGR antibody of the invention.

To determine if an antibody competes for binding with a reference anti-GCGR antibody, the above-described binding methodology is performed in two orientations: In a first orientation, the reference antibody is allowed to bind to a GCGR molecule under saturating conditions followed by assessment of binding of the test antibody to the GCGR molecule. In a second orientation, the test antibody is allowed to bind to a GCGR molecule under saturating conditions followed by assessment of binding of the reference antibody to the GCGR molecule. If, in both orientations, only the first (saturating) antibody is capable of binding to the GCGR molecule, then it is concluded that the test antibody and the reference antibody compete for binding to GCGR. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Species Selectivity and Species Cross-Reactivity

According to certain embodiments of the invention, the anti-GCGR antibodies bind to human GCGR but not to GCGR from other species. Alternatively, the anti-GCGR antibodies of the invention, in certain embodiments, bind to human GCGR and to GCGR from one or more non-human species. For example, the anti-GCGR antibodies of the invention may bind to human GCGR and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee GCGR.

Immunoconjugates

The invention encompasses a human anti-GCGR monoclonal antibody conjugated to a therapeutic moiety ("immunoconjugate"), such as an agent that is capable of reducing blood glucose levels, or a radioisotope, or a chemotherapeutic agent. The type of therapeutic moiety that may be conjugated to the anti-GCGR antibody will take into account the condition to be treated and the desired therapeutic effect to be achieved. For example, for treating diabetes, or any other condition whereby it is desirable to lower blood glucose, and/or to maintain normal blood glucose levels, an agent such as biguanide (e.g. metformin), a sulfonylurea (e.g. glyburide, glipizide), a PPAR gamma agonist (e.g. pioglitazone, rosiglitazone); an alpha glucosidase inhibitor (e.g. acarbose, voglibose), an inhibitor of advanced glycation endproduct formation (e.g. aminoguanidine), or a second GCGR inhibitor may be conjugated to the GCGR antibody. Alternatively, if the desired therapeutic effect is to treat the sequelae or symptoms associated with diabetes, or any other condition resulting from high, or uncontrolled blood glucose levels, it may be advantageous to conjugate an agent appropriate to treat the sequelae or symptoms of the condition Examples of suitable agents for forming immunoconjugates are known in the art, see for example, WO 05/103081.

Multi-Specific Antibodies

The antibodies of the present invention may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-GCGR antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multi-specific antibody with a second binding specificity. For example, the present invention includes bi-specific antibodies wherein one arm of an immunoglobulin is specific for human GCGR or a fragment thereof, and the other arm of the immunoglobulin is specific for a second therapeutic target or is conjugated to a therapeutic moiety. In certain embodiments of the invention, one arm of an immunoglobulin is specific for an epitope on the N-terminal domain of hGCGR or a fragment thereof, and the other arm of the immunoglobulin is specific for an epitope on one of the EC loops of hGCGR, or a fragment thereof. In certain embodiments, one arm of an immunoglobulin is specific for one EC loop, or a fragment thereof, and the second arm is specific for a second EC loop, or a fragment thereof. In certain embodiments, one arm of an immunoglobulin is specific for one epitope on one EC loop of hGCGR and the other arm is specific for a second epitope on the same EC loop of hGCGR.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Therapeutic Administration and Formulations

The invention provides therapeutic compositions comprising the anti-GCGR antibodies or antigen-binding fragments thereof of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When the antibody of the present invention is used for lowering blood glucose levels associated with GCGR activity in various conditions and diseases, such as diabetes, in an adult patient, it is advantageous to intravenously administer the antibody of the present invention normally at a single dose of about 0.01 to about 30 mg/kg body weight, more preferably about 0.02 to about 7, about 0.03 to about 5, or about 0.05 to about 3 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see, for example, Langer (1990) Science 249:1527-1533).

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousands Oaks, CA), the PENLET™ (Haselmeier, Stuttgart, Germany), the EPIPEN (Dey, L. P.) and the HUMIRA™ Pen (Abbott Labs, Abbott Park, IL), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

Due to their interaction with the glucagon receptor, the present antibodies are useful for lowering blood glucose levels and also for the treatment of a wide range of conditions and disorders in which blocking the interaction of glucagon with its receptor is beneficial. These disorders and conditions may be selected from any glucagon related metabolic disorder, which involves glucagon receptor signaling that results in the pathophysiology of the disorder, or in the homeostatic response to the disorder. Thus, the antibodies may find use for example to prevent, treat, or alleviate, diseases or conditions or associated symptoms or sequelae, of the endocrine system, the central nervous system, the peripheral nervous system, the cardiovascular system, the pulmonary system, and the gastrointestinal system, while reducing and or eliminating one or more of the unwanted side effects associated with the current treatments. Glucagon related metabolic disorders include, but are not limited to, type 1 and type 2 diabetes, diabetic ketoacidosis, hyperglycemia, hyperglycemic hyperosmolar syndrome, perioperative hyperglycemia, hyperglycemia in the intensive care unit patient, hyperinsulinemia, postprandial hyperglycemia, impaired fasting glucose (IFG), metabolic syndrome, hyper-/hypokalemia, poor LDL/HDL ratio, eating disorders, weight gain, obesity as a consequence of diabetes, pediatric diabetes, gestational diabetes, diabetic late complications, micro-/macroalbuminuria, nephropathy, retinopathy, neuropathy, diabetic foot ulcers, wound healing, impaired glucose tolerance (IGT), insulin resistance syndromes, syndrome X, glucagonomas, gastrointestinal disorders, obesity, diabetes as a consequence of obesity, etc. The present invention further provides; a method of treating conditions resulting from excessive glucagon in a mammal; a method of inhibiting the glucagon receptor in a mammal; a method of inhibiting a glucagon receptor mediated cellular response in a mammal, or a method of reducing the glycemic level in a mammal comprising administering to a mammal in need of such treatment a glucagon receptor-inhibiting amount of an anti-GCGR antibody or a biologically active fragment thereof.

The present antibodies are effective in lowering blood glucose, both in the fasting and the postprandial stage. In certain embodiments of the invention, the present antibodies are used for the preparation of a pharmaceutical composition for the treatment of type 2 diabetes. In yet a further embodiment of the invention the present antibodies are used for the preparation of a pharmaceutical composition for the delaying or prevention of the progression from impaired glucose tolerance to type 2 diabetes. In yet another embodiment of the invention the present antibodies are used for the preparation of a pharmaceutical composition for the delaying or prevention of the progression from non-insulin requiring diabetes to insulin requiring diabetes. In a further embodiment of the invention the present antibodies are used for the preparation of a pharmaceutical composition for the treatment of type 1 diabetes. Such treatment is normally accompanied by insulin therapy.

Combination Therapies

Combination therapies may include an anti-hGCGR antibody of the invention and any additional therapeutic agent that may be advantageously combined with an antibody of the invention, or with a biologically active fragment of an antibody of the invention.

For example, a second therapeutic agent may be employed to aid in further lowering of glucose levels, or to reduce at least one symptom in a patient suffering from a disease or condition characterized by high blood glucose levels, such as diabetes mellitus. Such a second agent may be selected from, for example, a glucagon antagonist or another GCGR antagonist (e.g. an anti-glucagon or anti-GCGR antibody or small molecule inhibitor of glucagon or GCGR), or may include other therapeutic moieties useful for treating diabetes, or other diseases or conditions associated with, or resulting from elevated blood glucose levels, or impaired glucose metabolism, or agents useful for treating any long term complications associated with elevated and/or uncontrolled blood glucose levels. These agents include biguanides, which decrease glucose production in the liver and increase sensitivity to insulin (e.g. metformin), or sulfonylureas, which stimulate insulin production (e.g. glyburide, glipizide). Additional treatments directed at maintaining glucose homeostasis including PPAR gamma agonists, which act as insulin sensitizers (e.g. pioglitazone, rosiglitazone); and alpha glucosidase inhibitors, which slow starch absorption and glucose production (e.g. acarbose, voglibose). Additional treatments include injectable treatments such as Exenatide® (glucagon-like peptide 1), and Symlin® (pramlintide).

In certain other embodiments, the composition may include a second agent selected from the group consisting of non-sulfonylurea secretagogues, insulin, insulin analogs, exendin-4 polypeptides, beta 3 adrenoceptor agonists, PPAR agonists, dipeptidyl peptidase IV inhibitors, statins and statin-containing combinations, cholesterol absorption inhibitors, LDL-cholesterol antagonists, cholesteryl ester transfer protein antagonists, endothelin receptor antagonists, growth hormone antagonists, insulin sensitizers, amylin mimetics or agonists, cannabinoid receptor antagonists, glucagon-like peptide-1 agonists, melanocortins, melanin-concentrating hormone receptor agonists, SNRIs, and protein tyrosine phosphatase inhibitors.

In certain other embodiments, combination therapy may include administration of a second agent to counteract any potential side effect(s) resulting from administration of an antibody of the invention, if such side effect(s) occur. For example, in the event that any of the anti-GCGR antibodies increases lipid or cholesterol levels, it may be beneficial to administer a second agent to lower lipid or cholesterol levels, using an agent such as a HMG-COA reductase inhibitor (for example, a statin such as atorvastatin, (LIPITOR®), fluvastatin (LESCOL®), lovastatin (MEVACOR®), pitavastatin (LIVALO®), pravastatin (PRAVACHOL®), rosuvastatin (CRESTOR®) and simvastatin (ZOCOR®). Alternatively, the antibodies of the invention may be combined with an agent such as VYTORIN®, which is a preparation of a statin and another agent-such as ezetimibe/simvastatin.

In certain embodiments, it may be beneficial to administer the antibodies of the invention in combination with any one or more of the following: (1) niacin, which increases lipoprotein catabolismo (2) fibrates or amphipathic carboxylic acids, which reduce low-density lipoprotein (LDL) level, improve high-density lipoprotein (HDL) and TG levels, and reduce the number of non-fatal heart attacks; and (3) activators of the LXR transcription factor that plays a role in cholesterol elimination such as 22-hydroxycholesterol, or a statin with a bile resin (e.g., cholestyramine, colestipol, colesevelam), a fixed combination of niacin plus a statin (e.g., niacin with lovastatin); or with other lipid lowering agents such as omega-3-fatty acid ethyl esters (for example, OMACOR®).

Furthermore, the second therapeutic agent can be one or more other inhibitors of glucagon or GCGR, as well as inhibitors of other molecules, such as angiopoietin-like protein 3 (ANGPTL3), angiopoietin-like protein 4 (ANGPTL4), angiopoietin-like protein 5 (ANGPTL5), angiopoietin-like protein 6 (ANGPTL6), which are involved in lipid metabolism, in particular, cholesterol and/or triglyceride homeostasis. Inhibitors of these molecules include small molecules and antibodies that specifically bind to these molecules and block their activity.

In certain embodiments, it may be beneficial to administer the antibodies of the invention in combination with an antibody that acts to lower lipid or cholesterol levels, such as, but not limited to, for example, any anti-PCSK9 (proprotein convertase subtilisin/kexin type 9) antibody, such as those described in US2010/0166768. Other anti-PCSK9 antibodies are described in US2010/0040611, US2010/0041102, US2010/0040610, US2010/0113575, US2009/0232795, US2009/0246192, US2010/0233177, US2009/0142352, US2009/0326202, US2010/0068199, US2011/

0033465, US2011/0027287, US2010/0150937, US2010/0136028 and WO2009/055783.

In certain embodiments, it may be beneficial to administer the anti-GCGR antibodies of the invention in combination with a nucleic acid that inhibits the activity of PCSK9 (proprotein convertase subtilisin/kexin type 9), such as an antisense molecule, a double stranded RNA, or a siRNA molecule. Exemplary nucleic acid molecules that inhibit the activity of PCSK9 are described in US2011/0065644, US2011/0039914, US2008/0015162 and US2007/0173473.

The additional therapeutically active component(s) may be administered prior to, concurrent with, or after the administration of the anti-GCGR antibody of the present invention. For purposes of the present disclosure, such administration regimens are considered the administration of an anti-GCGR antibody "in combination with" a second therapeutically active component.

Diagnostic Uses of the Antibodies

The anti-GCGR antibodies of the present invention may also be used to detect and/or measure GCGR in a sample, e.g., for diagnostic purposes. For example, an anti-GCGR antibody, or fragment thereof, may be used to diagnose a condition or disease characterized by aberrant expression (e.g., over-expression, under-expression, lack of expression, etc.) of GCGR. Exemplary diagnostic assays for GCGR may comprise, e.g., contacting a sample, obtained from a patient, with an anti-GCGR antibody of the invention, wherein the anti-GCGR antibody is labeled with a detectable label or reporter molecule or used as a capture ligand to selectively isolate GCGR protein from patient samples. Alternatively, an unlabeled anti-GCGR antibody can be used in diagnostic applications in combination with a secondary antibody which is itself detectably labeled. The detectable label or reporter molecule can be a radioisotope, such as $^3H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure GCGR in a sample include enzyme-linked immunosorbent assay (ELISA), radioimmunoassay (RIA), and fluorescence-activated cell sorting (FACS).

Samples that can be used in GCGR diagnostic assays according to the present invention include any tissue or fluid sample obtainable from a patient, which contains detectable quantities of GCGR protein, or fragments thereof, under normal or pathological conditions. Generally, levels of GCGR in a particular sample obtained from a healthy patient (e.g., a patient not afflicted with a disease or condition associated with abnormal GCGR levels or activity) will be measured to initially establish a baseline, or standard, level of GCGR. This baseline level of GCGR can then be compared against the levels of GCGR measured in samples obtained from individuals suspected of having a GCGR related disease or condition, or symptoms associated with such disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for.

Unless indicated otherwise, parts are parts by weight, molecular weight is average molecular weight, temperature is in degrees Centigrade, and pressure is at or near atmospheric.

Example 1. Generation of Human Antibodies to Human GCGR

An immunogen comprising any one of the following can be used to generate antibodies to hGCGR. For example, cells expressing hGCGR were used in certain embodiments as an immunogen to generate antibodies to hGCGR. Additionally, DNA encoding hGCGR was used in certain embodiments as an immunogen to prepare the antibodies of the invention. Furthermore, in certain embodiments, peptides comprising amino acid sequences from the N-terminal domain of hGCGR were utilized as an immunogen to generate antibodies to human GCGR. In addition, in certain embodiments, peptides comprising amino acid sequences from any of the extracellular loop regions EC1, EC2, or EC3, of hGCGR may be utilized as an immunogen to generate antibodies to human GCGR. The cells, DNA, or peptides that were used as immunogens, as noted above, were administered directly, with an adjuvant to stimulate the immune response, to a VELOCIMMUNE® mouse comprising DNA encoding human Immunoglobulin heavy and kappa light chain variable regions. The antibody immune response was monitored by a GCGR-specific immunoassay. When a desired immune response was achieved splenocytes were harvested and fused with mouse myeloma cells to preserve their viability and form hybridoma cell lines. The hybridoma cell lines were screened and selected to identify cell lines that produce GCGR-specific antibodies. Using this technique, and the various immunogens described above, several anti-GCGR chimeric antibodies (i.e., antibodies possessing human variable domains and mouse constant domains) were obtained; certain exemplary antibodies generated in this manner were designated as H4H1345N, H4H1617N and H4H1765N.

Anti-GCGR antibodies were also isolated directly from antigen-positive B cells without fusion to myeloma cells, as described in U.S. 2007/0280945A1, herein specifically incorporated by reference in its entirety. Using this method, several fully human anti-GCGR antibodies (i.e., antibodies possessing human variable domains and human constant domains) were obtained; exemplary antibodies generated in this manner were designated as follows: H4H1321B, H4H1321P, H4H1327B, H4H1327P, H4H1328B, H4H1328P, H4H1331B, H4H1331P, H4H1339B and H4H1339P.

The biological properties of the exemplary anti-GCGR antibodies generated in accordance with the methods of this Example are described in detail in the Examples set forth below.

Example 2. Heavy and Light Chain Variable Region Amino Acid Sequences

Table 1 sets forth the heavy and light chain variable region amino acid sequence pairs of selected anti-GCGR antibodies and their corresponding antibody identifiers. Antibodies having the same numerical antibody designation, but differing by a letter suffix of N, B or P refer to antibodies having heavy and light chains with identical CDR sequences but with sequence variations in regions that fall outside of the CDR sequences (i.e., in the framework regions). Thus, N, B and P variants of a particular antibody have identical CDR sequences within their heavy and light chain variable regions but differ from one another within their framework regions.

TABLE 1

| Antibody Designation | HCVR | HCDR1 | HCDR2 | HCDR3 | LCVR | LCDR1 | LCDR2 | LCDR3 |
|---|---|---|---|---|---|---|---|---|
| H4H1345N | 2 | 4 | 6 | 8 | 10 | 12 | 14 | 16 |
| H4H1617N | 18 | 20 | 22 | 24 | 26 | 28 | 30 | 32 |
| H4H1765N | 34 | 36 | 38 | 40 | 42 | 44 | 46 | 48 |
| H4H1321B | 50 | 52 | 54 | 56 | 58 | 60 | 62 | 64 |
| H4H1321P | 66 | 52 | 54 | 56 | 68 | 60 | 62 | 64 |
| H4H1327B | 70 | 72 | 74 | 76 | 78 | 80 | 82 | 84 |
| H4H1327P | 86 | 72 | 74 | 76 | 88 | 80 | 82 | 84 |
| H4H1328B | 90 | 92 | 94 | 96 | 98 | 100 | 102 | 104 |
| H4H1328P | 106 | 92 | 94 | 96 | 108 | 100 | 102 | 104 |
| H4H1331B | 110 | 112 | 114 | 116 | 118 | 120 | 122 | 124 |
| H4H1331P | 126 | 112 | 114 | 116 | 128 | 120 | 122 | 124 |
| H4H1339B | 130 | 132 | 134 | 136 | 138 | 140 | 142 | 144 |
| H4H1339P | 146 | 132 | 134 | 136 | 148 | 140 | 142 | 144 |

Example 3. Variable Gene Utilization Analysis

To analyze the structure of antibodies produced, the nucleic acids encoding antibody variable regions were cloned and sequenced. From the nucleic acid sequence and predicted amino acid sequence of the antibodies, gene usage was identified for each Heavy Chain Variable Region (HCVR) and Light Chain Variable Region (LCVR). Table 2 sets forth the gene usage for selected antibodies in accordance with the invention.

TABLE 2

| Antibody | Antibody Identifier HCVR/LCVR SEQ ID NOs | HCVR | | | LCVR | |
|---|---|---|---|---|---|---|
| | | $V_H$ | $D_H$ | $J_H$ | $V_K$ | $J_K$ |
| H4H1617N | 18/26 | V1-24 | D3-9 | J6 | V2-28 | J1 |
| H4H1345N | 2/10 | V1-24 | D3-9 | J6 | V2-28 | J1 |
| H4H1765N | 34/42 | V3-48 | D6-6 | J6 | V2-28 | J1 |
| H4H1321P | 66/68 | V3-30 | D3-9 | J6 | V1-16 | J4 |
| H4H1327P | 86/88 | V3-7 | D3-9 | J6 | V1-17 | J3 |
| H4H1328P | 106/108 | V3-13 | D3-9 | J6 | V1-17 | J4 |
| H4H1331P | 126/128 | V3-33 | D3-9 | J6 | V1-17 | J1/J4 |
| H4H1339P | 146/148 | V3-13 | D3-9 | J6 | V1-6 | J1 |

Example 4. Antibody Binding to Soluble GCGR as Determined by Surface Plasmon Resonance Binding affinities and kinetic constants of human monoclonal anti-hGCGR antibodies binding to human and monkey soluble recombinant hGCGR ectodomain (hGCGR and MfGCGR, respectively) were determined by surface plasmon resonance at both 25° C. and 37° C. Measurements were conducted on a T100 Biacore instrument. Antibodies were captured onto the Biacore sensor chip surface via a covalently-linked anti-human kappa antibody capture surface, and the soluble GCGR proteins were applied to the surface either in a monovalent (hGCGR expressed with a myc-myc-hexa-histidine C-terminal tag) or bivalent (hGCGR and MfGCGR expressed with an N-terminal Fc fusion) format. The amino acid sequence identifiers of the reagents used in this example are shown in Table 3.

TABLE 3

| Description | Construct | SEQ ID NO: |
|---|---|---|
| anti-GCGR positive control hIgG4(S108P) | 150 kDa, dimer | (See Yan, Hai et al. WO2008/036341) |
| mfGCGR-N-terminal hFc | 160k | 152 |
| hGCGR-mFc | 80654.42 Da, dimer | 149 |
| hGCGR-mmh | 18,965 Da, monomer | 151 |

The soluble GCGR was applied to the flow cell in separate injections at multiple concentrations ranging from 3.1 nM to 50 nM, and kinetic association ($k_a$) and dissociation ($k_d$) rate constants were determined by fitting the data to a 1:1 binding model using Scrubber v2.0a curve fitting software. Binding dissociation equilibrium constants and dissociative half-lives were calculated from the kinetic rate constants as: $K_D=k_d/k_a$; $t_{1/2}=(\ln 2/k_d)$.

TABLE 4a

Biacore data for binding at 25° C.

| Antibody Designation | Antigen tested | ka | kd | $K_D$ | T1/2 (min) |
|---|---|---|---|---|---|
| H4H1321P | hGCGR-mmh | 1.06E+06 | 3.74E−03 | 3.54E−09 | 3 |
| | hGCGR-hFc | 1.20E+06 | 2.85E−04 | 2.38E−10 | 41 |
| | mfGCGR-hFc | 1.76E+06 | 4.18E−05 | 2.38E−11 | 276 |
| H4H1327P | hGCGR-mmh | 9.52E+05 | 3.52E−04 | 3.69E−10 | 33 |
| | hGCGR-hFc | 1.21E+06 | 4.10E−04 | 3.38E−11 | 282 |
| | mfGCGR-hFc | 1.60E+06 | 1.44E−05 | 9.02E−12 | 802 |
| H4H1328P | hGCGR-mmh | 1.03E+06 | 2.12E−03 | 2.06E−09 | 5 |
| | hGCGR-hFc | 1.13E+06 | 2.26E−04 | 2.01E−10 | 51 |
| | mfGCGR-hFc | 1.60E+06 | 8.46E−05 | 5.29E−11 | 137 |
| H4H1331P | hGCGR-mmh | 6.57E+05 | 1.11E−04 | 1.70E−10 | 104 |
| | hGCGR-hFc | 7.60E+05 | 1.54E−05 | 2.02E−11 | 751 |
| | mfGCGR-hFc | 1.17E+06 | 8.12E−06 | 6.90E−12 | 1423 |
| H4H1339P | hGCGR-mmh | 6.45E+05 | 5.32E−04 | 8.25E−10 | 22 |
| | hGCGR-hFc | 1.00E+06 | 6.20E−05 | 6.18E−11 | 186 |
| | mfGCGR-hFc | 1.26E+06 | 2.28E−05 | 1.82E−11 | 506 |
| H4H1345N | hGCGR-mmh | 7.98E+05 | 3.44E−04 | 4.31E−10 | 34 |
| | hGCGR-hFc | 7.90E+05 | 5.72E−05 | 7.24E−11 | 202 |
| | mfGCGR-hFc | 9.53E+05 | 2.42E−05 | 2.54E−11 | 477 |
| H4H1617N | hGCGR-mmh | 1.07E+06 | 1.99E−04 | 1.87E−10 | 58 |
| | hGCGR-hFc | 8.18E+05 | 3.18E−05 | 3.89E−11 | 363 |
| | mfGCGR-hFc | 1.26E+06 | 1.38E−05 | 1.10E−11 | 835 |
| H4H1765N | hGCGR-mmh | 3.26E+05 | 3.05E−05 | 9.30E−11 | 379 |
| | hGCGR-hFc | 4.10E+05 | 4.95E−06 | 1.22E−11 | 2331 |
| | mfGCGR-hFc | 6.43E+05 | 1.00E−06 | 1.56E−12 | 11550 |
| Isotype-matched comparator antibody | hGCGR-mmh | 6.67E+05 | 1.68E−04 | 2.52E−10 | 69 |
| | hGCGR-hFc | 8.21E+05 | 2.04E−05 | 2.49E−11 | 565 |
| | mfGCGR-hFc | 1.23E+06 | 6.09E−06 | 4.95E−12 | 1897 |

TABLE 4b

Biacore data for binding at 37° C.

| Antibody Designation | Antigen tested | ka | kd | $K_D$ | T1/2 (min) |
|---|---|---|---|---|---|
| H4H1321P | hGCGR-mmh | 1.58E+06 | 2.02E−02 | 1.28E−08 | 1 |
| | hGCGR-hFc | 1.41E+06 | 1.09E−04 | 7.70E−11 | 106 |
| | mfGCGR-hFc | 2.19E+06 | 7.59E−05 | 3.47E−11 | 152 |
| H4H1327P | hGCGR-mmh | 1.48E+06 | 2.00E−03 | 1.35E−09 | 6 |
| | hGCGR-hFc | 1.48E+06 | 2.32E−04 | 1.57E−10 | 50 |
| | mfGCGR-hFc | 2.22E+06 | 7.94E−05 | 3.57E−11 | 145 |
| H4H1328P | hGCGR-mmh | 1.61E+06 | 1.08E−02 | 6.67E−09 | 1 |
| | hGCGR-hFc | 1.55E+06 | 1.92E−04 | 1.24E−10 | 60 |
| | mfGCGR-hFc | 2.03E+06 | 7.17E−05 | 3.53E−11 | 161 |
| H4H1331P | hGCGR-mmh | 9.73E+05 | 5.19E−04 | 5.33E−10 | 22 |
| | hGCGR-hFc | 1.17E+06 | 9.12E−05 | 7.79E−11 | 127 |
| | mfGCGR-hFc | 1.60E+06 | 4.12E−05 | 2.57E−11 | 281 |
| H4H1339P | hGCGR-mmh | 8.76E+05 | 4.30E−03 | 4.91E−09 | 3 |
| | hGCGR-hFc | 1.17E+06 | 3.71E−04 | 3.18E−10 | 31 |
| | mfGCGR-hFc | 1.69E+06 | 1.07E−04 | 6.31E−11 | 108 |
| H4H1345N | hGCGR-mmh | 9.28E+05 | 1.97E−03 | 2.12E−09 | 6 |
| | hGCGR-hFc | 9.52E+05 | 3.09E−04 | 3.24E−10 | 37 |
| | mfGCGR-hFc | 1.27E+06 | 1.28E−04 | 1.01E−10 | 91 |
| H4H1617N | hGCGR-mmh | 1.20E+06 | 1.13E−03 | 9.43E−10 | 10 |
| | hGCGR-hFc | 1.18E+06 | 2.14E−04 | 1.81E−10 | 54 |
| | mfGCGR-hFc | 1.49E+06 | 8.72E−05 | 5.86E−11 | 133 |
| H4H1765N | hGCGR-mmh | 4.41E+05 | 1.11E−04 | 2.52E−10 | 104 |
| | hGCGR-hFc | 6.64E+05 | 3.57E−05 | 5.37E−11 | 324 |
| | mfGCGR-hFc | 9.04E+05 | 1.48E−05 | 1.64E−11 | 778 |
| Isotype-matched comparator antibody | hGCGR-mmh | 8.73E+05 | 1.46E−03 | 1.68E−09 | 8 |
| | hGCGR-hFc | 1.15E+06 | 1.82E−04 | 1.59E−10 | 63 |
| | mfGCGR-hFc | 1.66E+06 | 6.27E−05 | 3.77E−11 | 184 |

As shown in Tables 4a and 4b, the exemplary antibodies exhibited high affinity binding to both human and monkey GCGR soluble proteins. A significant increase in binding affinity (5-fold to 15-fold) was observed when flowing the bivalent hGCGR in comparison to monovalent hGCGR. The antibodies consistently bound with higher affinity (3-fold to 10-fold) to the monkey variant, MfGCGR, compared to hGCGR.

Example 5. Bioassay to measure the Effects of Anti-GCGR Antibodies on GCGR Activation GCGR is a G-protein coupled receptor and its ligand, glucagon (GCG), stimulates adenylyl cyclase activity through Gαs and phosphoinositol turnover through Gq (Jiang and Zhang, (2003), Am J Physiol Endocrinol Metab 284: E671-E678). A bioassay was developed to detect activation through Gαs, subsequent elevation of cAMP levels and transcriptional activation. HEK293 cell lines were generated to stably express full-lengths of human GCGR (GenBank accession number NP_000151.1; SEQ ID NO: 153), monkey (*Macaca fascicularis*) GCGR (SEQ ID NO: 155), and mouse GCGR (NP_032127.2; SEQ ID NO: 154.) along with a luciferase reporter assay. The stable cell lines were isolated and maintained in 10% FBS, DMEM, NEAA, Pen/Strep, and 500 mg/ml G418. For rat GCGR, the HEK293 cell line expressing the reporter gene [CRE (4X)-luciferase-IRES-GFP] was transiently transfected with full-length rat GCGR (NP_742089.1; SEQ ID NO: 156) using LIPOFECTAMINE™ 2000 (Invitrogen).

For the bioassay, 293/GCGR cells were seeded onto 96-well assay plates at 20,000 cells/well in low serum media, 0.1% FBS and OPTI-MEM™, and incubated at 37° C. and 5% $CO_2$ overnight. Next day, GCG was serially diluted at 1:3 and added to cells starting from 100 nM to 0.002 nM including no GCG control for dose response. For inhibition, antibodies were serially diluted at 1:3 and added to cells starting from 200 to 0.003 (for hGCGR cells) or 100 nM to 0.002 nM (for monkey, mouse and rat GCGR cells) including no antibody control with constant concentration of 100 pM GCG. Luciferase activity was detected after 5.5 hrs of incubation in 37° C. and 5% $CO_2$.

EC50 values for stimulation of each reporter cell-line by 100 pM GCG are shown in Table 5a. The results of the IC50 values for antibodies blocking stimulation of cells by 100 pM GCG are shown in Table 5b, including the results for two control antibodies, Control mAb1 (positive control expressed as hIgG4 isotype; for example, see WO2008/036341 for the antibody designated as "A-9" having the HCVR of SEQ ID NO: 275, HCDR1 of SEQ ID NO: 102, HCDR2 of SEQ ID NO: 128, and HCDR3 of SEQ ID NO: 169 and the LCVR of SEQ ID NO: 229, LCDR1 of SEQ ID NO: 14, LCDR2 of SEQ ID NO: 50 and the LCDR3 of SEQ ID NO: 74) and Control mAb2 (an isotype-matched negative control).

Regarding the inhibition of human GCGR by anti-GCGR antibodies, the activation of GCGR by GCG was shown to stimulate luciferase activity with an EC50 of 113 pM and all antibodies except Control mAb2 (isotype matched negative control) blocked the activation of GCG at 100 pM and decreased the luciferase activity.

With respect to the inhibition of monkey GCGR by anti-GCGR antibodies, the activation of GCGR by GCG was shown to stimulate luciferase activity with an EC50 of 36 pM and all antibodies except Control mAb2 (isotype matched negative control) blocked the activation of GCG at 100 pM and decreased the luciferase activity. H4H1765N showed a partial inhibition of GCG at highest concentration of antibody tested, 100 nM.

Regarding the inhibition of mouse GCGR by anti-GCGR antibodies, the activation of GCGR by GCG was shown to stimulate luciferase activity with an EC50 of 83 pM and all antibodies except H4H1345N, H4H1617N, H4H1765N and Control mAb2 (isotype matched negative control) blocked the activation of GCG at 100 pM and decreased the luciferase activity.

With respect to the inhibition of rat GCGR by anti-GCGR antibodies, the activation of GCGR by GCG was shown to stimulate luciferase activity with an EC50 of 252 pM and all antibodies except H4H1765N and Control mAb2 (isotype matched negative control) blocked the activation of GCG at 100 pM and decreased the luciferase activity.

TABLE 5a

| Cell lines | hGCGR | mfGCGR | mGCGR | rat GCGR |
|---|---|---|---|---|
| EC50 (pM) | 113 | 36 | 83 | 252 |
| Constant GCG (pM) | | 100 | | |

TABLE 5b

| Antibody Designation | IC50 (nM) | | | |
|---|---|---|---|---|
| | hGCGR | mfGCGR | mGCGR | rat GCGR |
| H4H1321P | 0.27 | 4.03 | 1.13 | 1.21 |
| H4H1327P | 0.39 | 2.56 | 1.04 | 0.88 |
| H4H1328P | 0.24 | 2.73 | 1.26 | 0.93 |
| H4H1331P | 0.66 | 8.29 | 1.62 | 3.87 |

TABLE 5b-continued

| Antibody Designation | IC50 (nM) | | | |
|---|---|---|---|---|
| | hGCGR | mfGCGR | mGCGR | rat GCGR |
| H4H1339P | 0.46 | 2.85 | 1.60 | 0.97 |
| H4H1345N | 2.22 | 3.86 | Not Blocked | 8.07 |
| H4H1617N | 1.25 | 4.24 | Not Blocked | 3.66 |
| H4H1765N | 12.78 | 75.16 | Not Blocked | Not Blocked |
| Control mAb1 Positive control | 0.30 | 2.38 | 1.69 | 0.69 |
| Control mAb2 Negative control | Not Blocked | Not Blocked | Not Blocked | Not Blocked |

In summary, eight anti-hGCGR fully-human antibodies were tested and demonstrated blocking of activation of human GCGR by 100 pM GCG in a reporter cell line that exhibited an EC50 of 113 pM when stimulated by GCG alone. In the monkey GCGR reporter cell line, seven out of eight tested antibodies fully inhibited activation by 100 pM GCG. H4H1765N did not fully inhibit monkey GCGR at the highest concentration of antibody tested, 100 nM. Five out of eight of the antibodies fully inhibited the activation by 100 pM GCG in the mouse GCGR reporter cell line, and seven out of eight antibodies inhibited the activation by 100 pM GCG in the rat GCGR-transfected reporter cells.

Example 6. Effect of Anti-GCGR Antibodies in Ob/Ob Mice

Selected anti-hGCGR antibodies, all of which cross-react with mouse GCGR, were tested for their ability to reduce blood glucose levels in ob/ob mice, a mouse model of type 2 diabetes. ob/ob mice were put into ten groups of five or six animals. Each group received subcutaneous injections of each antibody at 1 or 10 mg/kg. The control group was injected with a hIgG isotype control antibody, which does not bind to any known mouse proteins. Two or seven days after antibody dosing at 1 or 10 mg/kg, respectively, a few drops of blood obtained by tail bleeds were collected from mice. Specifically, for the group given the antibody designated H4H1327P at 10 mg/kg, tail bleeds were collected more frequently at 2, 4, 7, 9, 11, 14, 16, 18, and 21 days after dosing. Blood glucose levels from the tail bleed samples were determined by ACCU-CHEK® Compact Plus (Roche). The percent reduction in blood glucose from the mean blood glucose levels of the control group was calculated for each animal at each time point. The average percent reduction in blood glucose was calculated for each antibody group. Table 6 summarizes the mean blood glucose levels of the control group. Results, expressed as (mean±SEM) of percent blood glucose reduction, are shown in Tables 7a and 7b.

TABLE 6

| Time | Blood glucose (mg/dL) |
|---|---|
| Day 0 | 197 ± 14 |
| Day 2 | 185 ± 13 |
| Day 4 | 167 ± 6 |
| Day 7 | 202 ± 20 |
| Day 9 | 205 ± 18 |
| Day 11 | 195 ± 23 |
| Day 14 | 229 ± 13 |
| Day 16 | 206 ± 6 |
| Day 18 | 187 ± 11 |
| Day 21 | 209 ± 16 |

TABLE 7a

| Dosage | Time (days) | Blood glucose reduction (%) Antibody Designation | | | |
|---|---|---|---|---|---|
| | | H4H1327P | H4H1328P | H4H1331P | H4H1339P |
| 1 mg/kg | 2 | 49 ± 1 | 45 ± 2 | 46 ± 2 | 46 ± 2 |
| 10 mg/kg | 7 | 53 ± 2 | 50 ± 2 | 55 ± 2 | 52 ± 2 |

TABLE 7b

| Antibody Designation | Blood glucose reduction (%) Time (days) | | | | | | | | |
|---|---|---|---|---|---|---|---|---|---|
| | 2 | 4 | 7 | 9 | 11 | 14 | 16 | 18 | 21 |
| H4H1327P | 58 ± 2 | 52 ± 2 | 53 ± 2 | 56 ± 2 | 47 ± 3 | 51 ± 3 | 45 ± 4 | 34 ± 5 | −5 ± 17 |

Mice treated with the anti-hGCGR antibodies tested (shown in Tables 7a and 7b) exhibited significant reductions in blood glucose levels compared to mice injected with control antibody.

Example 7. Effect of Anti-GCGR Antibodies in Transgenic Mice Expressing the Human GCGR Protein The effects of anti-hGCGR antibodies on blood glucose and plasma lipid levels were determined in transgenic mice expressing the human GCGR protein ("humanized GCGR mice"). Humanized GCGR mice were generated by replacing the mouse GCGR gene with the human GCGR gene (SEQ ID NO: 157; encoding full-length protein, GenBank accession number NP_000151.1; SEQ ID NO: 153) in C57BL6/129 (F1H4) embryonic stem cells. After germ line transmission was established, heterozygous mice ($GCGR^{hum/+}$) were bred together to generate homozygous mice ($GCGR^{hum/hum}$) on a C57BL6 background. Homozygous humanized GCGR mice were put into ten groups of three or four animals. Each group received subcutaneous injections of each antibody at 3 mg/kg. The Control I group was injected with a hIgG isotype control antibody, which does not bind to any known mouse proteins. The Control II group was injected with an anti-hGCGR hIgG4 antibody, which has been validated to decrease blood glucose levels of humanized GCGR mice. Mice were bled three days after antibody dosing, and blood glucose levels were determined by ACCU-CHEK® Compact Plus (Roche). The percent reduction in blood glucose from the mean blood glucose levels of the Control I group was calculated for each animal. The average percent reduction in blood glucose was calculated for each antibody group. Table 8a summarizes the mean blood glucose levels of the control group. Results, expressed as (mean±SEM) of percent blood glucose reduction, are shown in Table 8b.

Additionally with the Control I, Control II and H4H1765N groups, mice were bled before and 3 and 8 days after antibody dosing, and plasma lipid levels were determined by ADVIA® 1650 Chemistry System (Siemens). Averages were calculated for each of the measurements of low density lipoprotein cholesterol (LDL-C), high density lipoprotein cholesterol (HDL-C), total cholesterol (TOTAL-C), triglycerides (TG), nonesterified fatty acids (NEFA) levels for each of the three groups. Results, expressed as (mean±SEM) of plasma lipid concentrations, are shown in Table 8c.

Mice treated with most of the anti-hGCGR antibodies tested (shown in Table 8b) exhibited significant reductions in blood glucose levels compared to mice receiving control antibody. Mice treated with certain of the anti-hGCGR antibodies tested (shown in Table 8c) exhibited significant reductions in triglyceride levels compared to mice receiving control antibody. In particular, the lowering of triglyceride levels was observed with two anti-GCGR antibodies, one designated as H4H1765N (data shown below in Table 8c) and the other designated as H4H1327P (data not shown).

TABLE 8a

| Time | Blood glucose (mg/dL) |
|---|---|
| Day 0 | 155 ± 6 |
| Day 1 | 160 ± 5 |
| Day 3 | 155 ± 5 |
| Day 6 | 164 ± 7 |
| Day 8 | 156 ± 7 |
| Day 10 | 154 ± 9 |
| Day 13 | 149 ± 5 |

TABLE 8b

| Antibody Designation | Blood glucose reduction (%) |
|---|---|
| Control II | 37 ± 3 |
| H4H1321P | 32 ± 4 |
| H4H1327P | 40 ± 7 |
| H4H1328P | 31 ± 7 |
| H4H1331P | 33 ± 4 |
| H4H1339P | 31 ± 6 |
| H4H1617N | 15 ± 5 |
| H4H1345N | 14 ± 2 |
| H4H1765N | 32 ± 4 |

TABLE 8c

| Antibody Designation | Time (days) | LDL-C (mg/dL) | HDL-C (mg/dL) | TOTAL-C (mg/dL) | TG (mg/dL) | NEFA (mmol/L) |
|---|---|---|---|---|---|---|
| Control I | Pre | 9.4 ± 1.4 | 47 ± 4 | 97 ± 10 | 98 ± 6 | 0.67 ± 0.06 |
| | 3 | 7.7 ± 1.1 | 45 ± 3 | 95 ± 4 | 80 ± 8 | 0.96 ± 0.03 |
| | 8 | 9.8 ± 2.2 | 46 ± 2 | 99 ± 4 | 120 ± 19 | 0.88 ± 0.05 |
| Control II | Pre | 6.7 ± 0.4 | 37 ± 1 | 76 ± 2 | 69 ± 12 | 0.60 ± 0.09 |
| | 3 | 11.2 ± 1.6 | 51 ± 2 | 101 ± 8 | 58 ± 5 | 0.80 ± 0.11 |
| | 8 | 14.4 ± 2.1 | 57 ± 3 | 114 ± 7 | 74 ± 15 | 0.73 ± 0.04 |
| H4H1765N | Pre | 8.7 ± 0.2 | 39 ± 6 | 79 ± 8 | 94 ± 19 | 0.81 ± 0.12 |
| | 3 | 8.0 ± 1.1 | 46 ± 6 | 91 ± 9 | 68 ± 7 | 0.72 ± 0.06 |
| | 8 | 9.2 ± 1.6 | 46 ± 6 | 92 ± 8 | 75 ± 7 | 0.70 ± 0.05 |

Example 8: Effect of Combination Therapy with an Anti-GCGR Antibody and an Antibody Specific for PCSK9 (Proprotein Convertase Subtilisin/Kexin Type 9) on Blood Glucose, Plasma Lipid and Hepatic Triglyceride Levels in Mice Reagents The following antibodies were used to study the effect of combination therapy with an anti-GCGR antibody and an antibody specific for PCSK9 on blood glucose levels, plasma lipid levels and hepatic triglyceride levels in C57BL/6 mice: An anti-hIL4R antibody designated REGN496, which is an hIgG4 isotype control; an anti-GCGR (hIgG4) antibody designated H4H1327P; and an anti-PCSK9 (hIgG1) antibody designated H1H316P. The amino acid sequence identifiers for the HCVR, LCVR, HCDRs, and LCDRs are shown below in Table 9.

TABLE 9

| REGN AB Designation | SEQ ID NUMBERS | | | | | | | |
|---|---|---|---|---|---|---|---|---|
| | HCVR | HCDR1 | HCDR2 | HCDR3 | LCVR | LCDR1 | LCDR2 | LCDR3 |
| REGN496 | 194 | 195 | 196 | 197 | 198 | 199 | 200 | 201 |
| H4H1327P | 86 | 72 | 74 | 76 | 88 | 80 | 82 | 84 |
| H1H316P | 173 | 161 | 163 | 165 | 175 | 167 | 169 | 171 |

Experimental Procedure

The combined effects of H4H1327P, an anti-hGCGR antibody, and H1H316P, an anti-hPCSK9 antibody, on blood glucose, plasma lipid, and hepatic triglyceride (TG) levels were determined in C57BL/6 mice.

H4H1327P cross-reacts with mouse GCGR, and H1H316P cross-reacts with mouse PCSK9. C57BL/6 mice were put into six groups of six animals. Each group received once a week subcutaneous injections of an antibody or a combination of two antibodies. The first group was injected at 10 mg/kg with a hIgG4 isotype control antibody, which does not bind to any known mouse protein. The second and third group received H4H1327P at 3 mg/kg and 10 mg/kg, respectively. The fourth group was injected with 10 mg/kg H1H316P. The fifth group received a combination of 3 mg/kg H4H1327P and 10 mg/kg H1H316P, and the sixth group was injected with a combination of 10 mg/kg H4H1327P and 10 mg/kg H1H316P. Eleven and 19 days after the initial antibody dosing, mice were bled for blood glucose and plasma lipid measurements. At Day 19, liver was harvested for the determination of hepatic TG content. Blood glucose levels were measured with the use of ACCU-CHEK® Compact Plus (Roche). The percent reduction in blood glucose from the mean blood glucose level of the isotype control group was calculated for each animal. The percent reduction and associated error in blood glucose for each treatment group was then calculated by averaging across values for the individual animals in each group. Results, expressed as (mean±SEM) of percent blood glucose reduction, are shown in Table 10a and in FIG. 1.

Figure 2:
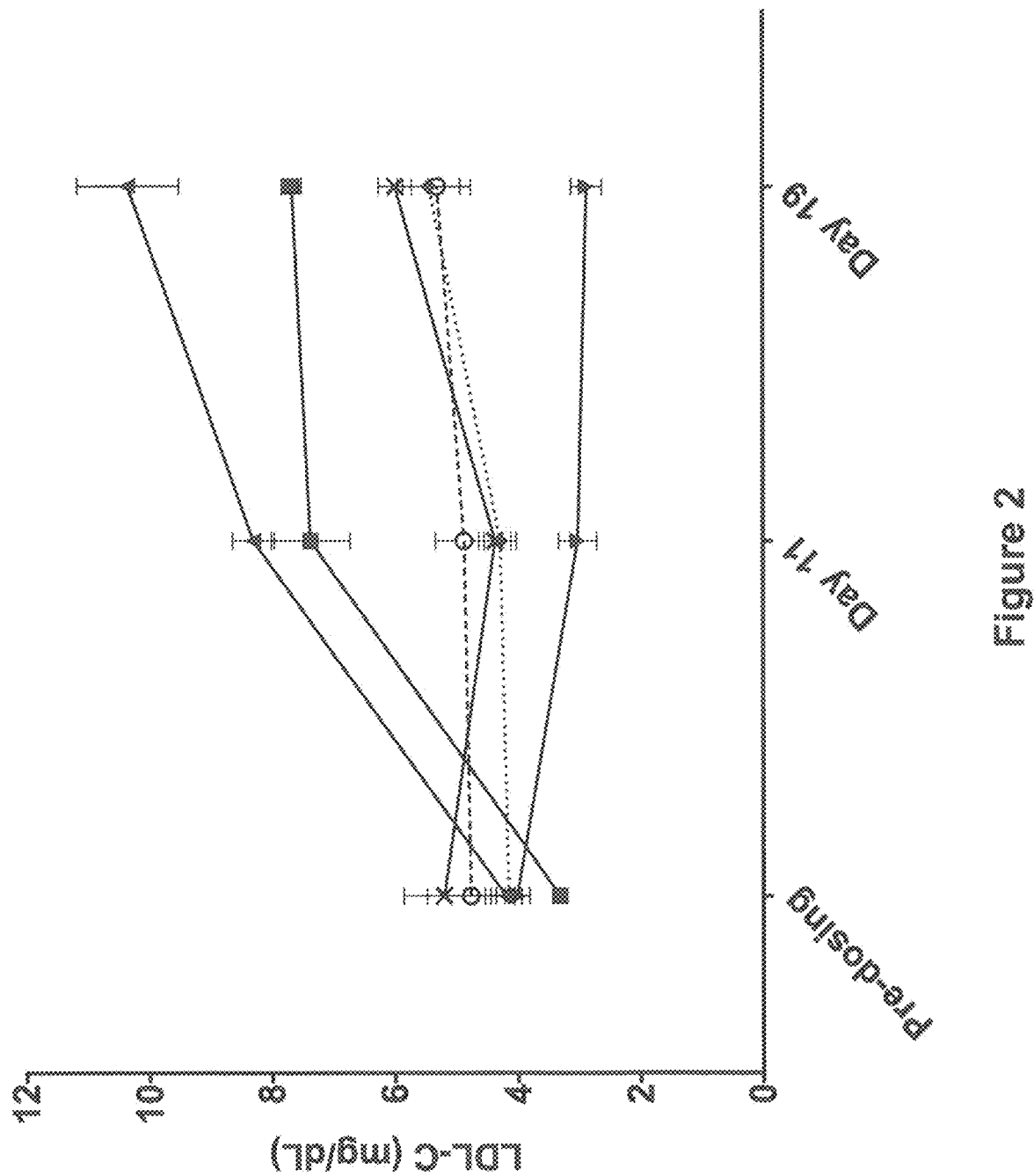
FIG. 2 shows plasma LDL-C levels in C57BL6 mice after administration of H4H1327P, and/or H1H316P when given alone or in combination. Control (X with solid line); H4H1327P at 3 mg/kg (■ with solid line); H4H1327P at 10 mg/kg (▲ with solid line); H1H316P at 10 mg/kg (♦ with solid line); H4H1327P at 3 mg/kg+H1H316P at 10 mg/kg (♦ with dashed line); H4H1327P at 10 mg/kg+H1H316P at 10 mg/kg (○ with dashed lines).
Figure 3:
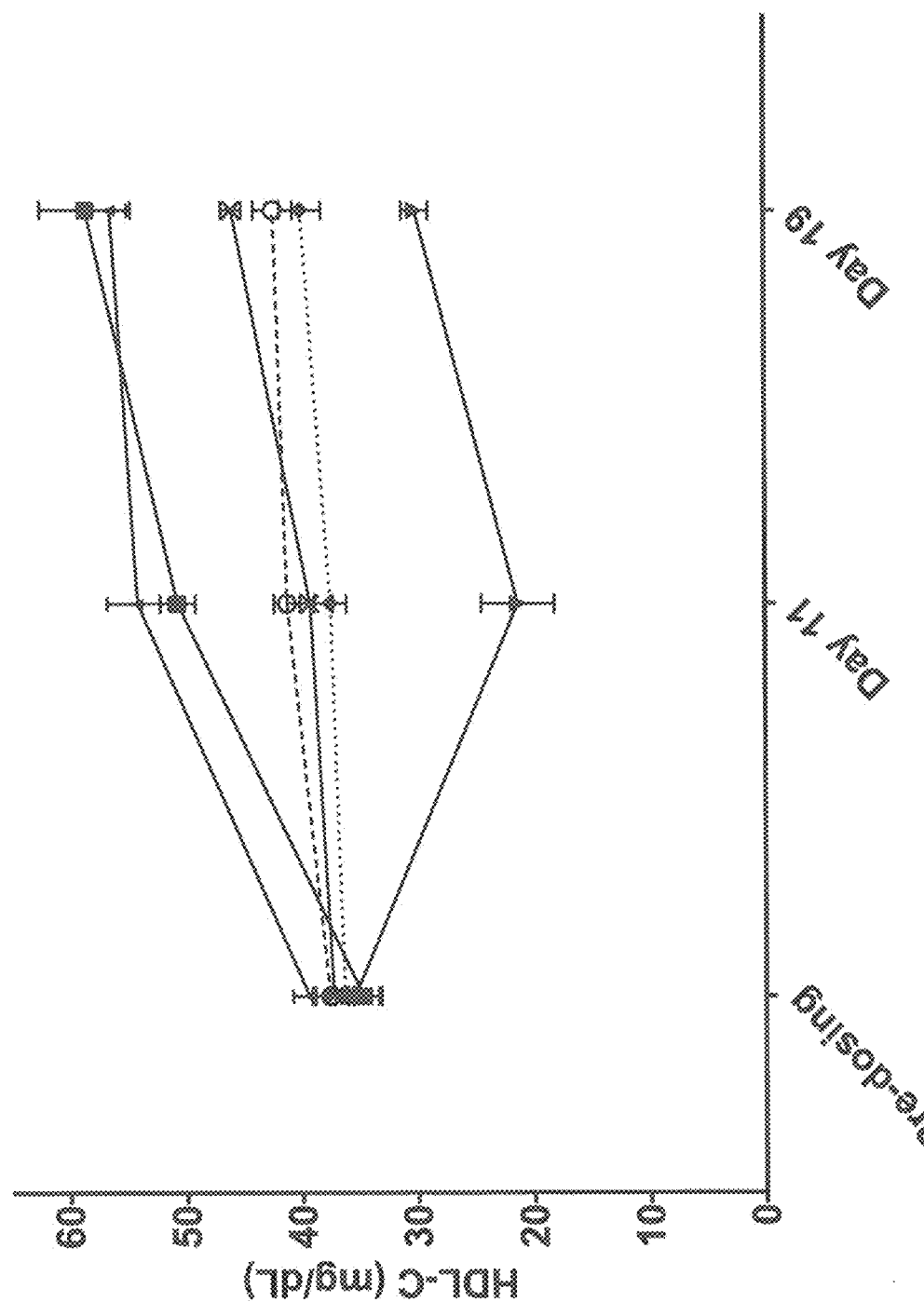
FIG. 3 shows plasma HDL-C levels in C57BL6 mice after administration of H4H1327P, and/or H1H316P when given alone or in combination. Control (X with solid line); H4H1327P at 3 mg/kg (■ with solid line); H4H1327P at 10 mg/kg (▲ with solid line); H1H316P at 10 mg/kg (♦ with solid line); H4H1327P at 3 mg/kg+H1H316P at 10 mg/kg (♦ with dashed line); H4H1327P at 10 mg/kg+H1H316P at 10 mg/kg (○ with dashed lines).
Figure 4:
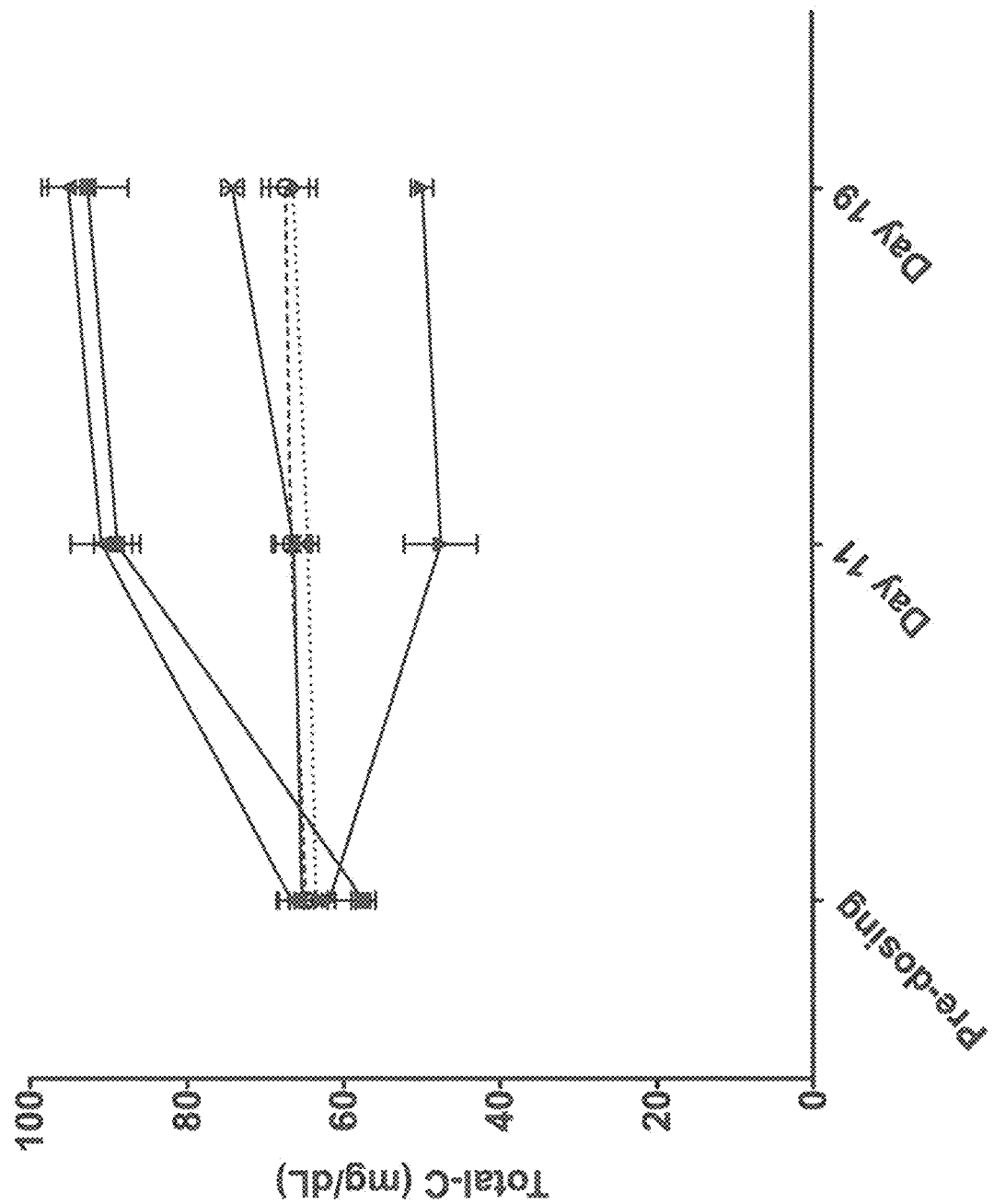
FIG. 4 shows total plasma cholesterol levels in C57BL6 mice after administration of H4H1327P, and/or H1H316P when given alone or in combination. Control (X with solid line); H4H1327P at 3 mg/kg (■ with solid line); H4H1327P at 10 mg/kg (▲ with solid line); H1H316P at 10 mg/kg (♦ with solid line); H4H1327P at 3 mg/kg+H1H316P at 10 mg/kg (♦ with dashed line); H4H1327P at 10 mg/kg+H1H316P at 10 mg/kg (○ with dashed lines).
Figure 5:
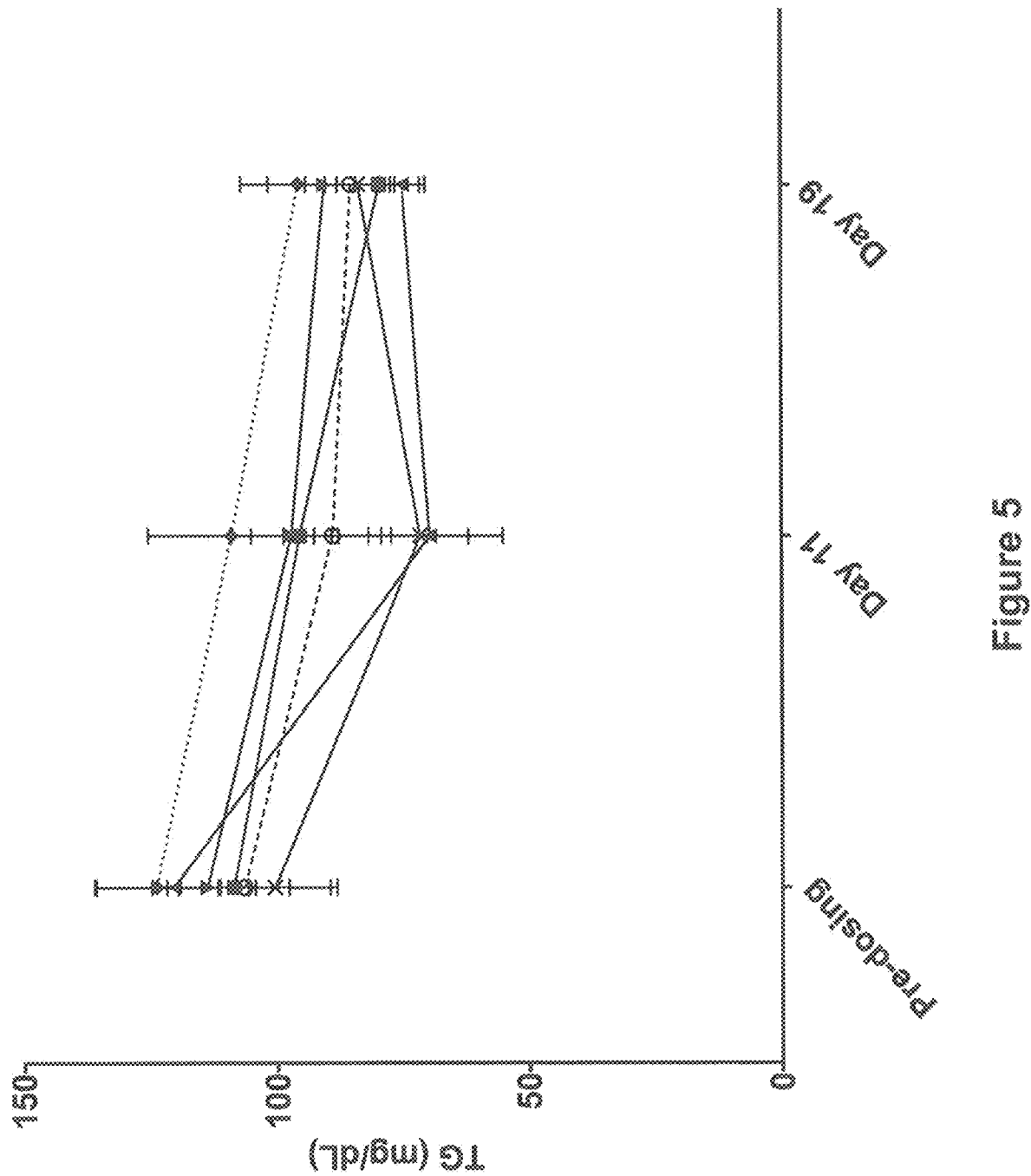
FIG. 5 shows plasma triglyceride levels in C57BL6 mice after administration of H4H1327P, and/or H1H316P when given alone or in combination. Control (X with solid line); H4H1327P at 3 mg/kg (■ with solid line); H4H1327P at 10 mg/kg (▲ with solid line); H1H316P at 10 mg/kg (♦ with solid line); H4H1327P at 3 mg/kg+H1H316P at 10 mg/kg (♦ with dashed line); H4H1327P at 10 mg/kg+H1H316P at 10 mg/kg (○ with dashed lines).
Figure 6:
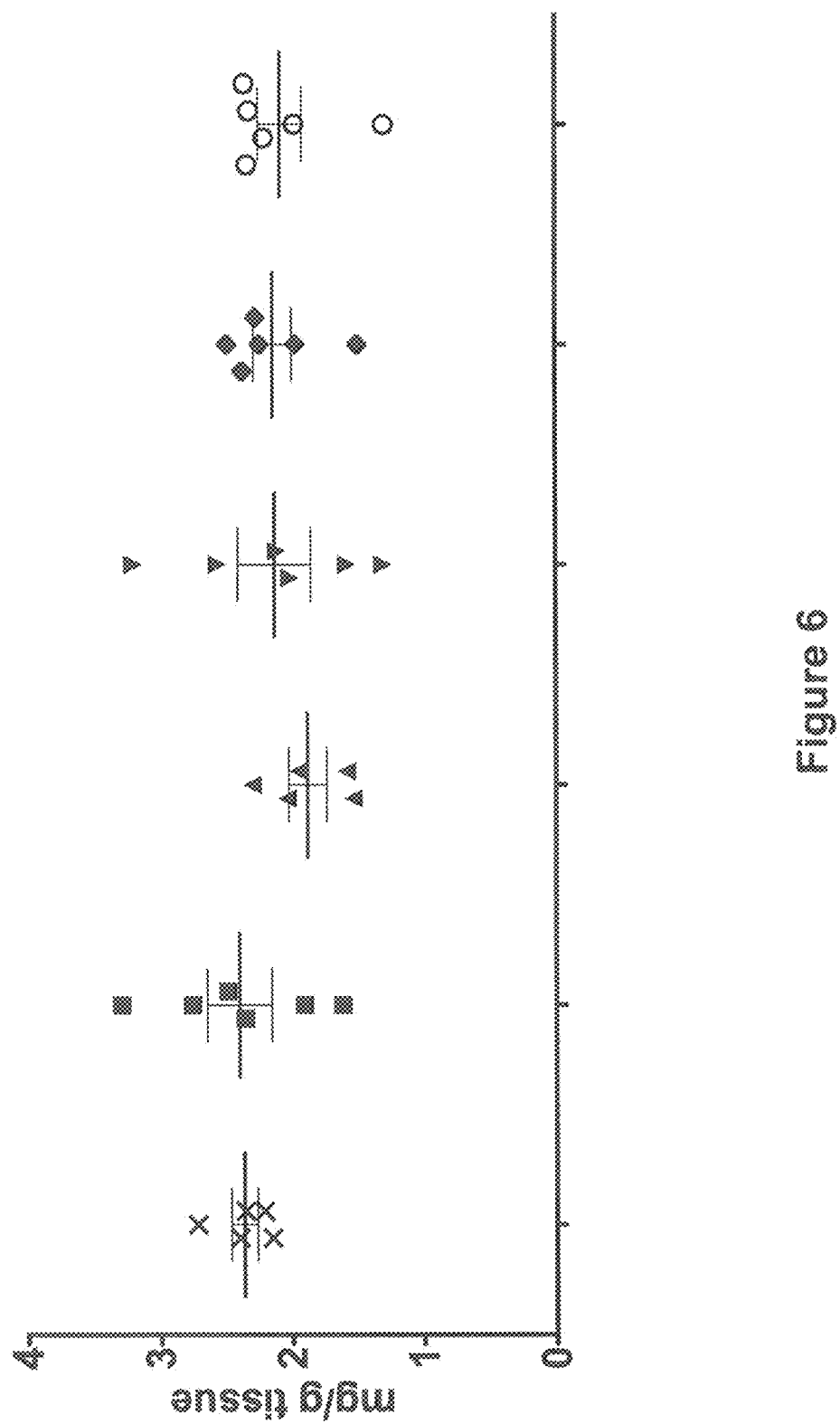
FIG. 6 shows hepatic triglyceride levels in C57BL6 mice after administration of H4H1327P, and/or H1H316P when given alone or in combination. Control (X); H4H1327P at 3 mg/kg (■) H4H1327P at 10 mg/kg (▲); H1H316P at 10 mg/kg (♦); H4H1327P at 3 mg/kg+H1H316P at 10 mg/kg (♦) H4H1327P at 10 mg/kg+H1H316P at 10 mg/kg (○).

Plasma lipid levels were determined by ADVIA® 1650 Chemistry System (Siemens). Hepatic TG contents were measured using a colorimetric assay (Teco Diagnostics) after extraction of TG from tissue with chloroform/methanol. Means were calculated for each of the measurements of plasma low density lipoprotein cholesterol (LDL-C), high density lipoprotein cholesterol (HDL-C), total cholesterol (TOTAL-C), TG and hepatic TG levels for each group. Results, expressed as (mean±SEM) of plasma and hepatic lipid concentrations, are shown in Table 10b and in FIG. 2 (plasma LDL-C levels); FIG. 3 (Plasma HDL-C levels); FIG. 4 (Plasma Total-C levels); FIG. 5 (Plasma TG levels); and FIG. 6 (hepatic TG content).

Results Summary and Conclusions

TABLE 10a

| | Blood glucose reduction (%) | | | | |
|---|---|---|---|---|---|
| Time (days) | H4H1327P 3 mg/kg | H4H1327P 10 mg/kg | H1H316P 10 mg/kg | H4H1327P 3 mg/kg + H1H316P 10 mg/kg | H4H1327P 10 mg/kg + H1H316P 10 mg/kg |
| 11 | 33 ± 7 | 40 ± 5 | 3 ± 3 | 28 ± 7 | 39 ± 2 |
| 19 | 25 ± 4 | 28 ± 4 | −4 ± 6 | 21 ± 7 | 27 ± 2 |

TABLE 10b

| Antibody | Time (days) | Plasma | | | | Liver TG (mg/g tissue) |
|---|---|---|---|---|---|---|
| | | LDL-C (mg/dL) | HDL-C (mg/dL) | TOTAL-C (mg/dL) | TG (mg/dL) | |
| Control | Pre-dosing | 5.2 ± 0.7 | 37 ± 2 | 65 ± 2 | 101 ± 11 | NA |
| | 11 | 4.4 ± 0.3 | 39 ± 2 | 66 ± 2 | 72 ± 16 | NA |
| | 19 | 6.0 ± 0.3 | 46 ± 1 | 74 ± 1 | 84 ± 6 | 2.4 ± 0.1 |
| H4H1327P 3 mg/kg | Pre-dosing | 3.3 ± 0.1 | 35 ± 1 | 58 ± 2 | 109 ± 11 | NA |
| | 11 | 7.4 ± 0.6 | 51 ± 2 | 89 ± 3 | 96 ± 14 | NA |
| | 19 | 7.7 ± 0.2 | 59 ± 4 | 93 ± 5 | 80 ± 8 | 2.4 ± 0.2 |
| H4H1327P 10 mg/kg | Pre-dosing | 4.2 ± 0.2 | 39 ± 1 | 67 ± 2 | 120 ± 16 | NA |
| | 11 | 8.3 ± 0.3 | 54 ± 3 | 91 ± 4 | 70 ± 8 | NA |
| | 19 | 10.4 ± 0.8 | 56 ± 1 | 95 ± 3 | 75 ± 5 | 1.9 ± 0.1 |
| H1H316P 10 mg/kg | Pre-dosing | 4.0 ± 0.2 | 35 ± 2 | 62 ± 3 | 114 ± 8 | NA |
| | 11 | 3.0 ± 0.3 | 21 ± 3 | 48 ± 5 | 97 ± 8 | NA |
| | 19 | 2.9 ± 0.2 | 30 ± 1 | 50 ± 1 | 91 ± 11 | 2.1 ± 0.3 |
| H4H1327P 10 mg/kg + H1H316P 10 mg/kg | Pre-dosing | 4.2 ± 0.2 | 36 ± 1 | 64 ± 1 | 124 ± 12 | NA |
| | 11 | 4.3 ± 0.3 | 38 ± 1 | 65 ± 1 | 109 ± 16 | NA |
| | 19 | 5.4 ± 0.5 | 40 ± 2 | 66 ± 3 | 96 ± 11 | 2.1 ± 0.1 |
| H4H1327P 3 mg/kg + H1H316P 10 ma/kg | Pre-dosing | 4.8 ± 0.7 | 38 ± 2 | 65 ± 4 | 107 ± 18 | NA |
| | 11 | 4.9 ± 0.5 | 41 ± 1 | 67 ± 2 | 89 ± 10 | NA |
| | 19 | 5.3 ± 0.6 | 42 ± 2 | 67 ± 3 | 85 ± 9 | 2.1 ± 0.2 |

NA: Not applicable

Tabulated Data Summary:

Mice treated with H4H1327P alone showed significant reductions in blood glucose levels and increases in LDL, HDL, and total cholesterol levels in comparison to mice receiving control mAb. Mice treated with H1H316P alone exhibited significant reductions in cholesterol levels with no change in blood glucose levels. Mice treated with a combination of H4H1327P and H1H316P showed significant reductions in blood glucose levels with no alterations in cholesterol levels in comparison to mice receiving control mAb. Hepatic TG contents were not altered in any of the treatment groups compared to the isotype control group.

Example 9. The Effect of an Anti-GCGR Antibody in a Diet-Induced Obesity Mouse Model The effects of H4H1327P, an anti-hGCGR antibody that cross-reacts with mouse GCGR, on blood glucose levels and body weights were determined in a diet-induced obesity (DIO) mouse model of type 2 diabetes (T2D).

The DIO model is developed by feeding mice on a high fat (60% kcal) diet (HFD) from 5~6 weeks of age. After approximately 6 weeks on the diet, mice develop metabolic abnormalities including insulin resistance, glucose intolerance, and obesity. The DIO model induces a physiological condition in mice closer to human T2D than that induced by the other two commonly used T2D models, ob/ob and db/db mice, since the latter two models result from mutations in leptin or leptin receptor genes, respectively, which are rarely the cause of T2D in humans.

In this study, eleven week-old male C57BL/6 mice, placed on HFD since 5 weeks of age, were purchased from Taconic farms, Inc. and kept on the diet for another 8 weeks. The mice were divided into 4 groups of 10 animals per group at 19 weeks of age. Each group received weekly (on days 0, 7, 14, and 21) subcutaneous injections of H4H1327P at 3, 10, or 30 mg/kg, or 30 mg/kg of the hIgG4 isotype control, which does not bind to any known mouse protein. Blood glucose levels and body weights were measured periodically, and 6 days after administering the last antibody dose (on day 27), 6 mice/group were sacrificed. For the next 6 weeks, blood glucose and body weights were monitored for the remaining 4 mice/group. The percent reduction in blood glucose levels compared to the mean blood glucose level of the isotype control group was calculated for each animal. The percent reduction and associated error in blood glucose for each treatment group was then calculated by averaging across values for the individual animals in each group. Results, expressed as (mean±SEM) of percent blood glucose reduction, are shown in Table 11. The percent change in body weight from the baseline (weight at day 0) was calculated for each animal. The percent change and associated error in body weight for each treatment group was then calculated by averaging across values for the individual animals in each group. Results, expressed as (mean±SEM) of percent body weight change from baseline, are shown in Table 12.

Results Summary and Conclusions

H4H1327P, at all dosages tested, reduced blood glucose and body weight of DIO mice compared to the isotype control groups. The greatest relative blood glucose reduction (48.5%) occurred in the highest dose (30 mg/kg) group at day 10, and the greatest relative body weight reduction (12.8%) occurred in the highest dose group at day 28. The lowest dose (3 mg/kg) groups achieved mean relative blood glucose lowering and mean body weight lowering values of at least 70% the values exhibited by the highest dose groups through day 28 (one week following the last dose). The observed blood glucose and body weight lowering effects following the last treatment on day 21 (i.e., on days 28, 47, and 68) persisted longer for the higher H4H1327P dose groups compared to the lower dose groups.

TABLE 11

| | Blood glucose reduction (%) | | |
|---|---|---|---|
| Time (days) | H4H1327P 3 mg/kg | H4H1327P 10 mg/kg | H4H1327P 30 mg/kg |
| 10 | 44.6 ± 2.8 | 44.4 ± 1.8 | 48.5 ± 1.5 |
| 19 | 33.9 ± 2.3 | 39.0 ± 1.9 | 37.5 ± 2.5 |
| 28 | 24.8 ± 1.7 | 28.1 ± 2.8 | 32.4 ± 1.6 |
| 47 | −3.9 ± 7.1 | 21.2 ± 7.0 | 30.0 ± 2.4 |
| 68 | −4.3 ± 7.9 | −1.1 ± 5.8 | −12.9 ± 12.1 |

TABLE 12

| | Body weight change from baseline (%) | | | |
|---|---|---|---|---|
| Time (days) | Isotype control 30 mg/kg | H4H1327P 3 mg/kg | H4H1327P 10 mg/kg | H4H1327P 30 mg/kg |
| 10 | 1.8 ± 0.6 | −5.5 ± 0.6 | −6.1 ± 0.6 | −5.8 ± 0.6 |
| 19 | 2.2 ± 0.6 | −7.3 ± 0.6 | −9.6 ± 0.6 | −10.3 ± 0.7 |
| 28 | 1.8 ± 0.4 | −9.2 ± 1.2 | −10.5 ± 0.5 | −12.8 ± 1.0 |
| 47 | 6.6 ± 0.8 | 5.2 ± 1.3 | 2.5 ± 1.4 | −3.7 ± 2.2 |
| 68 | 10.4 ± 1.1 | 9.7 ± 0.7 | 10.6 ± 1.0 | 8.2 ± 1.1 |

Example 10. The Effect of an Anti-GCGR Antibody in a Streptozotocin (STZ)-Induced Mouse Model of Diabetic Ketoacidosis The effects of H4H1327P, an anti-hGCGR antibody, which cross-reacts with mouse GCGR, on plasma ketone and glucose levels were determined in a streptozotocin (STZ)-induced mouse model of diabetic ketoacidosis (DKA). STZ is a chemical toxic to pancreatic beta cells of mammals which, therefore, destroys this cell type when administered to rodents. A single, high dose (200 mg/kg) injection of STZ to C57BL/6 mice leads to the development of severe hyperglycemia and ketonuria, conditions exhibited in human DKA, in 3 days. Nine-week-old male C57BL/6 mice, purchased from Taconic farms, Inc. were divided into 2 groups of 10 animals, and each group received either intraperitoneal injections of STZ (in citrate buffer) at 200 mg/kg or vehicle (also in citrate buffer). Three days later, severe hyperglycemia (blood glucose levels >400 mg/dL) and ketonuria were confirmed in all STZ treated animals. The next morning, the STZ treated mice were divided into 2 groups of 5 animals, and each group received an intravenous injection of H4H1327P or hIgG4 isotype control at 10 mg/kg. The citrate buffer treated mice were also divided into 2 groups of 5 animals, and each group received intravenous injection of H4H1327P or hIgG4 isotype control at 10 mg/kg. Mice were bled 18 hours before antibody dosing (2.5 days after the STZ administration) and 28 hours after antibody dosing under isoflurane anesthesia for plasma collection. Plasma ketone levels were determined by beta-hydroxybutyrate assay (Biovision), and plasma glucose levels by ADVIA® 1650 Chemistry System (Siemens). Averages were calculated for the measurements of beta-hydroxybutyrate and glucose levels for each of the four groups. Results, expressed as (mean±SEM) of plasma beta-hydroxybutyrate and glucose concentrations, are shown in Table 13.

Results Summary and Conclusions

A reduction (average 67%) in plasma beta-hydroxybutyrate (ketone) concentration was observed in STZ-induced diabetic ketoacidotic mice 28 hours after H4H1327P treatment in comparison to plasma levels 18 hours prior to the treatment, demonstrating that H4H1327P effectively lowered plasma ketone levels in a mouse model of DKA. For the STZ-treated mice dosed with isotype control antibody, a 14% average increase in blood glucose was observed for the serum samples collected 28 hours after control antibody treatment compared to the samples collected 18 hours before antibody treatment, whereas for the H4H1327P dosed mice in the STZ-treated group less than 1% average change in glucose was observed between serum samples collected at these two time points.

TABLE 13

|  | Time from antibody treatment (hrs) | Vehicle/ Isotype control | Vehicle/ H4H1327P | STZ/ Isotype control | STZ/ H4H1327P |
|---|---|---|---|---|---|
| Beta-hydroxybutyrate (mM) | −18 | 1.1 ± 0.6 | 0.6 ± 0.2 | 3.4 ± 0.7 | 3.6 ± 0.2 |
|  | 28 | 0.4 ± 0.0 | 0.8 ± 0.4 | 2.4 ± 0.6 | 1.2 ± 0.1 |
| Glucose (mg/dL) | −18 | 214 ± 24 | 250 ± 6 | 610 ± 39 | 601 ± 26 |
|  | 28 | 238 ± 16 | 152 ± 5 | 696 ± 66 | 606 ± 59 |

Example 11. Generation of a Bi-Specific Antibody

Various bi-specific antibodies are generated for use in practicing the methods of the invention. For example, GCGR-specific antibodies are generated in a bi-specific format (a "bi-specific") in which variable regions binding to distinct ectodomain and/or EC loop epitopes on GCGR are linked together to confer dual-loop specificity within a single binding molecule. Appropriately designed bi-specifics may enhance overall glucagon receptor blocking efficacy through increasing both GCGR specificity and binding avidity. Variable regions with specificity for individual ectodomain epitopes (e.g., segments of the N-terminal domain, or of the EC1, EC2, or EC3 GCGR loops) or that can bind to different regions within one ectodomain segment or loop are paired on a structural scaffold that allows each variable region to bind simultaneously to the separate epitopes, or to different regions within one ectodomain or EC loop. In one example for a bi-specific, heavy chain variable regions ($V_H$) from a binder with one ectodomain or loop specificity are recombined with light chain variable regions ($V_L$) from a series of binders with a second ectodomain or EC loop specificity to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind both GCGR and a second target, such as, but not limited to, for example, human proprotein convertase subtilisin/kexin type 9 (hPCSK9), may be prepared in a bi-specific format using techniques described herein, or other techniques known to those skilled in the art. Antibody variable regions binding to distinct GCGR regions that are extracellularly exposed are linked together with variable regions that bind to relevant sites on, for example, PCSK9, to confer dual-antigen specificity within a single binding molecule. Appropriately designed bi-specifics of this nature serve a dual function. For example, in the case of a bi-specific antibody that binds both GCGR and PCSK9, one may be able to lower blood glucose by virtue of one arm of the bi-specific antibody binding GCGR, while at the same time lowering plasma lipids, by virtue of the second arm of the antibody binding PCSK9. Variable regions with specificity for individual ectodomain epitopes of GCGR, are combined with a variable region with specificity for PCSK9 and are paired on a structural scaffold that allows each variable region to bind to the separate antigens.

The bi-specific binders are tested for binding and functional blocking of the target antigens, for example, GCGR and/or PCSK9, in any of the assays described above for antibodies. For example, standard methods to measure soluble protein binding are used to assess the bispecific-PCSK9 interaction, such as Biacore, ELISA, size exclusion chromatography, multi-angle laser light scattering, direct scanning calorimetry, and other methods. Binding of bi-specific antibodies to cells expressing GCGR is determined through flow cytometry using a fluorescently labeled secondary antibody recognizing either or both of the two target antigens bound to cells. Cross-reactivity to the different GCGR ectodomains or loops within and between different species variants is assessed using an ELISA binding assay in which synthetic peptides representing the different ectodomains or loops are coated onto the wells of microtiter plates, and binding of a bi-specific is determined through use of a secondary detection antibody. Binding experiments with loop peptides can also be conducted using surface plasmon resonance experiments, in which real-time binding interaction of peptide to antibody is measured by flowing a peptide or bi-specific across a sensor surface on which bi-specific or peptide, respectively, is captured. Functional in vitro blocking of the GCGR receptor by a bi-specific is determined using any bioassay such as that described herein, or by in vivo determination of blood glucose levels in appropriate animal models, such as those described herein. Functional in vitro blocking of PCSK9 by a bi-specific is determined using any bioassay such as that described in WO2010/077854, or in US2010/0166768, or by in vivo determination of plasma lipid levels in appropriate animal models, such as those described herein.

TABLE 14

Informal Sequence Listing

| SEQ ID NO | Sequence | Description |
|---|---|---|
| 1. | CAGGTCCAGT TGGTACAGTC TGGGGCTGAC GTGAAGAAGC CTGGGGCCTC AGTGAAGGTC TCCTGCAAGG TTTCCGGACA TATCCTCACT GATTTATCCA TGCACTGGGT GCGACAGCCT CCTGGAAAAG GACTTGAGTG GATGGCAGGT TTTGATCCTG AAGAAGGTAA AATAATCTAC GCACAGAAGT TCCAGGGCAG AGTCACCATG ACCGAGGACA CATCTACAGA CACAGCCTAC ATGGAGCTGA GCAGCCTGAG ATCTGGGGAC ACGGCCGTTT ATTACTGTGC AACAAGCGAT ATTTTGACTG GGTATTATAG AGACTACTAC GGTTTGGACG TCTGGGGCCA AGGGACCACG CTCACCGTCT CCTCA | DNA nucleotide sequence |
| 2. | QVQLVQSGAD VKKPGASVKV SCKVSGHILT DLSMHWVRQP PGKGLEWMAG FDPEEGKIlY AQKFQGRVTM TEDTSTDTAY MELSSLRSGD TAVYYCATSD ILTGYYRDYY GLDVWGQGTT LTVSS | AA amino acid sequence |

TABLE 14-continued

Informal Sequence Listing

| SEQ ID NO | Sequence | Description |
|---|---|---|
| 3. | GGACATATCC TCACTGATTT ATCC | DNA nucleotide sequence |
| 4. | GHILTDLS | AA amino acid sequence |
| 5. | TTTGATCCTG AAGAAGGTAA AATA | DNA nucleotide sequence |
| 6. | FDPEEGKI | AA amino acid sequence |
| 7. | GCAACAAGCG ATATTTTGAC TGGGTATTAT AGAGACTACT ACGGTTTGGA CGTC | DNA nucleotide sequence |
| 8. | ATSDILTGYY RDYYGLDV | AA amino acid sequence |
| 9. | GATATTGTGA TGACTCAGTC TCCACTCTTC CTGCCCGTCA CCCCTGGAGA GCCGGCCTCC ATCTCCTGCA GGTCTAGTCA GAGCCTCCTG CATAGTAAAG GATACAACTA TTTGGATTGG TACCTGCAGA AGCCAGGGCA GTCTCCACAA CTCCTGATCT ATTTGGGTTC TAATCGGGCC TCCGGGGTCC CTGACAGGTT CAGTGGCAGT GGATCAGGCA CAGATTTTAC ACTGAAAATC AGCAGAGTGG AGGCTGAAGA TGTTGGGGTT TATTACTGCA TGCAAACTCT ACAAACTCCT CGGACGTTCG GCCAAGGGAC CAAGGTGGAA ATCAAA | DNA nucleotide sequence |
| 10. | DIVMTQSPLF LPVTPGEPAS ISCRSSQSLL HSKGYNYLDW YLQKPGQSPQ LLIYLGSNRA SGVPDRFSGS GSGTDFTLKI SRVEAEDVGV YYCMQTLQTP RTFGQGTKVE IK | AA amino acid sequence |
| 11. | CAGAGCCTCC TGCATAGTAA AGGATACAAC TAT | DNA nucleotide sequence |
| 12. | QSLLHSKGYN Y | AA amino acid sequence |
| 13. | TTGGGTTCT | DNA nucleotide sequence |
| 14. | LGS | AA amino acid sequence |
| 15. | ATGCAAACTC TACAAACTCC TCGGACG | DNA nucleotide sequence |
| 16. | MQTLQTPRT | AA amino acid sequence |
| 17. | CAGGTCCAGT TGGTACAGTC TGGGGCTGAC GTGAAGAAGC CTGGGGCCTC AGTGAAGGTC TCCTGCAAGG TTTCCGGACA TATCCTCACT GATTTATCCA TGCACTGGGT GCGACAGGCT CCTGGAAAAG GGCTTGAGTG GATGGGAGGT TTTGATCCTG AAGAAGGTGA AATAATCTAC GCACAGAAGT TCCAGGGCAG AGTCACCATG ACCGAGGACA CATCTACAGA CACAGCCTAC ATGGAGCTGA GCAGCCTGAG ATCTGGGGAC ACGGCCGTTT ATTACTGTGC AACAAGCGAT ATTTTGACTG GTTATTATAG AGACTACTAC GGTTTGGACG TCTGGGGCCA AGGGACCACG CTCACCGTCT CCTCA | DNA nucleotide sequence |
| 18. | QVQLVQSGAD VKKPGASVKV SCKVSGHILT DLSMHWVRQA PGKGLEWMGG FDPEEGEIIY AQKFQGRVTM TEDTSTDTAY MELSSLRSGD TAVYYCATSD ILTGYYRDYY GLDVWGQGTT LTVSS | AA amino acid sequence |
| 19. | GGACATATCC TCACTGATTT ATCC | DNA nucleotide sequence |

TABLE 14-continued

Informal Sequence Listing

| SEQ ID NO | Sequence | Description |
|---|---|---|
| 20. | GHILTDLS | AA amino acid sequence |
| 21. | TTTGATCCTG AAGAAGGTGA AATA | DNA nucleotide sequence |
| 22. | FDPEEGEI | AA amino acid sequence |
| 23. | GCAACAAGCG ATATTTTGAC TGGTTATTAT AGAGACTACT ACGGTTTGGA CGTC | DNA nucleotide sequence |
| 24. | ATSDILTGYY RDYYGLDV | AA amino acid sequence |
| 25. | GATATTGTGA TGACTCAGTC TCCACTCTTC CTGCCCGTCA CCCCTGGAGA GCCGGCCTCC ATCTCCTGCA GGTCTAGTCA GAGCCTCCTG CATAGTAAAG GATACAACTA TTTGGATTGG TACCTGCAGA AGCCAGGGCA GTCTCCACAA CTCCTGATCT ATTTGGGTTC TAATCGGGCC TCCGGGGTCC CTGACAGGTT CAGTGGCAGT GGATCAGGCA CAGATTTTAC ACTGAAAATC AGCAGAGTGG AGGCTGAAGA TGTTGGGGTT TATTACTGCA TGCAAACTCT ACAAACTCCT CGGACGTTCG GCCAAGGGAC CAAGGTGGAA ATCAAA | DNA nucleotide sequence |
| 26. | DIVMTQSPLF LPVTPGEPAS ISCRSSQSLL HSKGYNYLDW YLQKPGQSPQ LLIYLGSNRA SGVPDRFSGS GSGTDFTLKI SRVEAEDVGV YYCMQTLQTP RTFGQGTKVE IK | AA amino acid sequence |
| 27. | CAGAGCCTCC TGCATAGTAA AGGATACAAC TAT | DNA nucleotide sequence |
| 28. | QSLLHSKGYN Y | AA amino acid sequence |
| 29. | TTGGGTTCT | DNA nucleotide sequence |
| 30. | LGS | AA amino acid sequence |
| 31. | ATGCAAACTC TACAAACTCC TCGGACG | DNA nucleotide sequence |
| 32. | MQTLQTPRT | AA amino acid sequence |
| 33. | GAGGAGCAAC TGGTGGAGTC TGGGGGAGAC TTGGTACAGC CTGGAGGGTC CCTAAGACTC TCCTGTGCAG CCTCTGGATT CACTCTCAGT AGTTATGAAA TGAACTGGGT CCGCCAGGCT CCAGGGAAGG GGCTGGAGTG GGTTTCATAC ATTAGTAGAG GTGGTAGTCT GATACACTAC ACAGACTCTG TGAAGGGCCG ATTCACCATC TCCAGAGACA ACGCCAAGAA TTCACTGTAT CTGCAAATGA ACAGCCTGAG AGCCGAGGAC ACGGCTGTTT ATTACTGTGT GAGAGACCCA GCAGCTCGTT ATCATTATTA TTATCACGGT ATGGACGTCT GGGGCCAAGG GACCACGGTC ACCGTCTCCT CA | DNA nucleotide sequence |
| 34. | EEQLVESGGD LVQPGGSLRL SCAASGFTLS SYEMNWVRQA PGKGLEWVSY ISRGGSLIHY TDSVKGRFTI SRDNAKNSLY LQMNSLRAED TAVYYCVRDP AARYHYYHG MDVWGQGTTV TVSS | AA amino acid sequence |
| 35. | GGATTCACTC TCAGTAGTTA TGAA | DNA nucleotide sequence |

TABLE 14-continued

Informal Sequence Listing

| SEQ ID NO | Sequence | Description |
|---|---|---|
| 36. | GFTLSSYE | AA amino acid sequence |
| 37. | ATTAGTAGAG GTGGTAGTCT GATA | DNA nucleotide sequence |
| 38. | ISRGGSLI | AA amino acid sequence |
| 39. | GTGAGAGACC CAGCAGCTCG TTATCATTAT TATTATCACG GTATGGACGT C | DNA nucleotide sequence |
| 40. | VRDPAARYHY YYHGMDV | AA amino acid sequence |
| 41. | GATATTGTGA TGACTCAGTC TCCACTCTCC CTGCCCGTCA CCCCTGGAGA GCCGGCCTCC ATCTCCTGCA GGTCTAGTCA GAGCCTCCTG CACAATAATG GATATAACTA TTTGGATTGG TATCTGCAGA AGCCAGGGCA GTCTCCACAG CTCCTGATCT ATTTGGGTTC TAGTCGGGCC TCCGGGGTCC CTGACAGGTT CAGTGGCAGT GGATCAGGCA CAGATTTTAT ACTGAAAATC AGCAGAGTGG AGGCTGAAGA TGTTGGGGTT TATTACTGCA TGCAAGCTCT ACAAACTCCG TGGACGTTCG GCCGAGGGAC CAAGGTGGAA ATCAAA | DNA nucleotide sequence |
| 42. | DIVMTQSPLS LPVTPGEPAS ISCRSSQSLL HNNGYNYLDW YLQKPGQSPQ LLIYLGSSRA SGVPDRFSGS GSGTDFILKI SRVEAEDVGV YYCMQALQTP WTFGRGTKVE IK | AA amino acid sequence |
| 43. | CAGAGCCTCC TGCACAATAA TGGATATAAC TAT | DNA nucleotide sequence |
| 44. | QSLLHNNGYN Y | AA amino acid sequence |
| 45. | TTGGGTTCT | DNA nucleotide sequence |
| 46. | LGS | AA amino acid sequence |
| 47. | ATGCAAGCTC TACAAACTCC GTGGACG | DNA nucleotide sequence |
| 48. | MQALQTPWT | AA amino acid sequence |
| 49. | GAGGTGCAGC TGGTGGAGTC TGGGGGAGGC GTGGTCCAGC CTGGAGGGTC CCTGAGACTC TCCTGTGCAG CCTCTGGATT CACCTTCAGT AGTTATGACA TGCACTGGGT CCGCCAGGCT CCAGGCAAGG GGCTGGAGTG GGTGGCAGTT ATATCATCTG ATGGACGTGA TAAATACTAT GTAGACTCCG TGAAGGGCCG ATTCACCATC TCCAGAGACA ACTCCAAGAA CACGCTTTAT CTGCAAATGA ACAGCCTGAG AGCTGAGGAC ACGGCTGTTT ATTACTGTGC GAAAGAGATG GTGTATTACG ATATTTTGAC TGGTTATCAT AACTACTACG GTATGGACGT CTGGGGCCAA GGGACCACGG TCACCGTCTC CTCA | DNA nucleotide sequence |
| 50. | EVQLVESGGG VVQPGRSLRL SCAASGFTFS SYDMHWVRQA PGKGLEWVAV ISSDGRDKYY VDSVKGRFTI SRDNSKNTLY LQMNSLRAED TAVYYCAKEM VYYDILTGYH NYYGMDVWGQ GTTVTVSS | AA amino acid sequence |
| 51. | GGATTCACCT TCAGTAGTTA TGAC | DNA nucleotide sequence |
| 52. | GFTFSSYD | AA amino acid sequence |

TABLE 14-continued

Informal Sequence Listing

| SEQ ID NO | Sequence | Description |
|---|---|---|
| 53. | ATATCATCTG ATGGACGTGA TAAA | DNA nucleotide sequence |
| 54. | ISSDGRDK | AA amino acid sequence |
| 55. | GCGAAAGAGA TGGTGTATTA CGATATTTTG ACTGGTTATC ATAACTACTA CGGTATGGAC GTC | DNA nucleotide sequence |
| 56. | AKEMVYYDIL TGYHNYYGMD V | AA amino acid sequence |
| 57. | GACATCGTGA TGACCCAGTC TCCATCCTCA CTGTCTGCAT CTGTAGGAGA CAGAGTCACC ATCACTTGTC GGGCGAGTCA GGGCATTAAC AATTATTTAG CCTGGTTTCA GCAGAAACCA GGGAAAGCCC CTAAGTCCCT GATCCATACT GCATCCAGTT TGCAAAGTGG GGTCCCATCA AGGTTCAGCG GCAGTGGATC TGGGACAGAT TCACTCTCA CCATCAGCAG CCTGCAGCCT GAAGATTTTG CAACTTATTA CTGCCAACAG TATAATACTT ACCCTCTCAC TTTCGGCGGA GGGACCAAAG TGGAGATCAA ACGA | DNA nucleotide sequence |
| 58. | DIVMTQSPSS LSASVGDRVT ITCRASQGIN NYLAWFQQKP GKAPKSLIHT ASSLQSGVPS 60 KFSGSGSGTD FTLTISSLQP EDFATYYCQQ YNTYPLTFGG GTKVEIKR | AA amino acid sequence |
| 59. | CAGGGCATTA ACAATTAT | DNA nucleotide sequence |
| 60. | QGINNY | AA amino acid sequence |
| 61. | ACTGCATCC | DNA nucleotide sequence |
| 62. | TAS | AA amino acid sequence |
| 63. | CAACAGTATA ATACTTACCC TCTCACT | DNA nucleotide sequence |
| 64. | QQYNTYPLT | AA amino acid sequence |
| 65. | CAGGTGCAGC TGGTGGAGTC TGGGGGAGGC GTGGTCCAGC CTGGGAGGTC CCTGAGACTC TCCTGTGCAG CCTCTGGATT CACCTTCAGT AGTTATGACA TGCACTGGGT CCGCCAGGCT CCAGGCAAGG GGCTGGAGTG GGTGGCAGTT ATATCATCTG ATGGACGTGA TAAATACTAT GTAGACTCCG TGAAGGGCCG ATTCACCATC TCCAGAGACA ACTCCAAGAA CACGCTTTAT CTGCAAATGA ACAGTTTGAG AGCTGAGGAC ACGGCTGTTT ATTACTGTGC GAAAGAGATG GTGTATTACG ATATTTTGAC TGGTTATCAT AACTACTACG GTATGGACGT CTGGGGCCAA GGGACCACGG TCACCGTCTC C | DNA nucleotide sequence |
| 66. | QVQLVESGGG VVQPGRSLRL SCAASGFTFS SYDMHWVRQA PGKGLEWVAV ISSDGRDKYY VDSVKGRFTI SRDNSKNTLY LQMNSLRAED TAVYYCAKEM VYYDILTGYH NYYGMDVWGQ GTTVTVS | AA amino acid sequence |
| 67. | GACATCCAGA TGACCCAGTC TCCATCCTCA CTGTCTGCAT CTGTAGGAGA CAGAGTCACC ATCACTTGTC GGGCGAGTCA GGGCATTAAC AATTATTTAG CCTGGTTTCA GCAGAAACCA GGGAAAGCCC CTAAGTCCCT GATCCATACT GCATCCAGTT TGCAAAGTGG GGTCCCATCA AGGTTCAGCG GCAGTGGATC TGGGACAGAT TCACTCTCA CCATCAGCAG CCTGCAGCCT GAAGATTTTG CAACTTATTA CTGCCAACAG TATAATACTT ACCCTCTCAC TTTCGGCGGA GGGACCAAGG TGGAGATCAA A | DNA nucleotide sequence |
| 68. | DIQMTQSPSS LSASVGDRVT ITCRASQGIN NYLAWFQQKP GKAPKSLIHT ASSLQSGVPS KFSGSGSGTD FTLTISSLQP EDFATYYCQQ YNTYPLTFGG GTKVEIK | AA amino acid sequence |

TABLE 14-continued

Informal Sequence Listing

| SEQ ID NO | Sequence | Description |
|---|---|---|
| 69. | CAGGTGCAGC TGGTGCAGTC TGGGGGAGGC TTGGTCCAGC CTGGGGGGTC CCTGAGACTC TCCTGTGCAG CCTCCGGATT CACCTTTAGT AACTATTTGA TGAACTGGGT CCGCCAGGCT CCAGGGAAGG GGCTGGAGTG GCTGGCCAAC ATACAGGAAG ATGGAATTGA GAAATACTAT GTGGACTCTG TGAAGGGCCG ATTCACCATC TCCAGAGACA ACGCCAAGAA CTCACTGTAT CTGCAAATGA ACAGCCTGAG AGCCGAGGAC ACGGCTGTGT ATTACTGTGC GAGAGAGCCC TCCCATTACG ATATTTTGAC TGGTTATGAC TACTATTACG GTATGGACGT CTGGGGCCAA GGGACCACGG TCACCGTCTC CTCA | DNA nucleotide sequence |
| 70. | QVQLVQSGGG LVQPGGSLRL SCAASGFTFS NYLMNWVRQA PGKGLEWLAN IQEDGIEKYY VDSVKGRFTI SRDNAKNSLY LQMNSLRAED TAVYYCAREP SHYDILTGYD YYYGMDVWGQ GTTVTVSS | AA amino acid sequence |
| 71. | GGATTCACCT TTAGTAACTA TTTG | DNA nucleotide sequence |
| 72. | GFTFSNYL | AA amino acid sequence |
| 73. | ATACAGGAAG ATGGAATTGA GAAA | DNA nucleotide sequence |
| 74. | IQEDGIEK | AA amino acid sequence |
| 75. | GCGAGAGAGC CCTCCCATTA CGATATTTTG ACTGGTTATG ACTACTATTA CGGTATGGAC GTC | DNA nucleotide sequence |
| 76. | AREPSHYDIL TGYDYYYGMD V | AA amino acid sequence |
| 77. | GACATCCAGT TGACCCAGTC TCCATCCTCC CTGTCTGCAT CTGTAGGAGA CAGAGTCACC ATCACTTGCC GGGCAAGTCA GGGCATTAGA AATGATTTAG CTGGTATCA GCAGAAACCA GGGAAAGCCC CTAAGCGCCT GATCTATGCT GCATCCAGTT TGCAAAGTGG GGTCCCATCA AGGTTCAGCG GCAGTGGATC TGGGACAGAA TTCATTCTCA CAGTCAGCAG CCTGCAGCCT GAAGACTTTG CAACTTATTA CTGTCTACAG TATAATAGTA ACCCATTCAC TTTCGGCCCT GGGACCAAGG TGGAGATCAA ACGA | DNA nucleotide sequence |
| 78. | DIQLTQSPSS LSASVGDRVT ITCRASQGIR NDLGWYQQKP GKAPKRLIYA ASSLQSGVPS RFSGSGSGTE FILTVSSLQP EDFATYYCLQ YNSNPFTFGP GTKVEIKR | AA amino acid sequence |
| 79. | CAGGGCATTA GAAATGAT | DNA nucleotide sequence |
| 80. | QGIRND | AA amino acid sequence |
| 81. | GCTGCATCC | DNA nucleotide sequence |
| 82. | AAS | AA amino acid sequence |
| 83. | CTACAGTATA ATAGTAACCC ATTCACT | DNA nucleotide sequence |
| 84. | LQYNSNPFT | AA amino acid sequence |

TABLE 14-continued

Informal Sequence Listing

| SEQ ID NO | Sequence | Description |
|---|---|---|
| 85. | GAGGTGCAGC TGGTGGAGTC TGGGGGAGGC TTGGTCCAGC CTGGGGGGTC CCTGAGACTC TCCTGTGCAG CCTCCGGATT CACCTTTAGT AACTATTTGA TGAACTGGGT CCGCCAGGCT CCAGGGAAGG GGCTGGAGTG GCTGGCCAAC ATACAGGAAG ATGGAATTGA GAAATACTAT GTGGACTCTG TGAAGGGCCG ATTCACCATC TCCAGAGACA ACGCCAAGAA CTCACTGTAT CTGCAAATGA ACAGCCTGAG AGCCGAGGAC ACGGCTGTGT ATTACTGTGC GAGAGAGCCC TCCCATTACG ATATTTTGAC TGGTTATGAC TACTATTACG GTATGGACGT CTGGGGCCAA GGGACCACGG TCACCGTCTC C | DNA nucleotide sequence |
| 86. | EVQLVESGGG LVQPGGSLRL SCAASGFTFS NYLMNWVRQA PGKGLEWLAN IQEDGIEKYY VDSVKGRFTI SRDNAKNSLY LQMNSLRAED TAVYYCAREP SHYDILTGYD YYYGMDVWGQ GTTVTVS | AA amino acid sequence |
| 87. | GACATCCAGA TGACCCAGTC TCCATCCTCC CTGTCTGCAT CTGTAGGAGA CAGAGTCACC ATCACTTGCC GGGCAAGTCA GGGCATTAGA AATGATTTAG CTGGTATCA GCAGAAACCA GGGAAAGCCC CTAAGCGCCT GATCTATGCT GCATCCAGTT TGCAAAGTGG GGTCCCATCA AGGTTCAGCG GCAGTGGATC TGGGACAGAA TTCATTCTCA CAGTCAGCAG CCTGCAGCCT GAAGACTTTG CAACTTATTA CTGTCTACAG TATAATAGTA ACCCATTCAC TTTCGGCCCT GGGACCAAAG TGGATATCAA A | DNA nucleotide sequence |
| 88. | DIQMTQSPSS LSASVGDRVT ITCRASQGIR NDLGWYQQKP GKAPKRLIYA ASSLQSGVPS RFSGSGSGTE FILTVSSLQP EDFATYYCLQ YNSNPFTFGP GTKVDIK | AA amino acid sequence |
| 89. | GAGGTGCAGC TGGTGCAGTC TGGGGGAGCC TTGGTACAGC CTGGGGGGTC CCTGAGACTC TCCTGTACAG CCTCTGGTTT CACCTTCAGT AACTACGACA TGCACTGGGT CCGCCAAACT ACAGGAAAAG GTCTGGAGTG GATCTCAGCT ATTGATACTG CTGGTGACAC ATACTATCCA GGCTCCGTGA AGGGCCGATT CACCGTCTCC AGAGAAAATG CCAAGAACTC CTTTTATCTT CAAATGAACA GCCTGAGAGC CGGGGACACG GCTGTGTATT ACTGTGCAAG GGAGGGGAAG TATTACGATA TTTTGACTGG TGACTACCAC TACTACGGTA TGGACGTCTG GGGCCAAGGG ACCACGGTCA CCGTCTCCTC A | DNA nucleotide sequence |
| 90. | EVQLVQSGGA LVQPGGSLRL SCTASGFTFS NYDMHWVRQT TGKGLEWISA IDTAGDTYYP GSVKGRFTVS RENAKNSFYL QMNSLRAGDT AVYYCAREGK YYDILTGDYH YYGMDVWGQG TTVTVSS | AA amino acid sequence |
| 91. | GGTTTCACCT TCAGTAACTA CGAC | DNA nucleotide sequence |
| 92. | GFTFSNYD | AA amino acid sequence |
| 93. | ATTGATACTG CTGGTGACAC A | DNA nucleotide sequence |
| 94. | IDTAGDT | AA amino acid sequence |
| 95. | GCAAGGGAGG GGAAGTATTA CGATATTTTG ACTGGTGACT ACCACTACTA CGGTATGGAC GTC | DNA nucleotide sequence |
| 96. | AREGKYYDIL TGDYHYYGMD V | AA amino acid sequence |
| 97. | GCCATCCGGA TGACCCAGTC TCCATCCTCC CTGTCTGCAT CTGTAGGAGA CAGAGTCACC ATCACTTGTC GGGCAAGTCA GGGCATTAGA AATGATTTAG CTGGTATCA GCAGAAACCA GGGAAAGCCC CTAAGCGACT GATCTATGCT ACATCCAGTT TGCAAAGTGG GGTCCCATCA AGGTTCAGCG GCAGTGGATC TGGGACAGAA TTCACTCTCA CAATCAGCAG CCTGCAGCCT GAAGATTTTG CAACTTATTA CTGTCTACAG CATAATAGTT ACCCGCTCAC TTTCGGCGGA GGGACCAAGG TGGAAATCAA ACGA | DNA nucleotide sequence |
| 98. | AIRMTQSPSS LSASVGDRVT ITCRASQGIR NDLGWYQQKP GKAPKRLIYA TSSLQSGVPS RFSGSGSGTE FTLTISSLQP EDFATYYCLQ HNSYPLTFGG GTKVEIKR | AA amino acid sequence |
| 99. | CAGGGCATTA GAAATGAT | DNA nucleotide sequence |

TABLE 14-continued

Informal Sequence Listing

| SEQ ID NO | Sequence | Description |
|---|---|---|
| 100. | QGIRND | AA amino acid sequence |
| 101. | GCTACATCC | DNA nucleotide sequence |
| 102. | ATS | AA amino acid sequence |
| 103. | CTACAGCATA ATAGTTACCC GCTCACT | DNA nucleotide sequence |
| 104. | LQHNSYPLT | AA amino acid sequence |
| 105. | GAGGTGCAGC TGGTGGAGTC TGGGGGAGCC TTGGTACAGC CTGGGGGGTC CCTGAGACTC TCCTGTACAG CCTCTGGTTT CACCTTCAGT AACTACGACA TGCACTGGGT CCGCCAAACT ACAGGAAAAG GTCTGGAGTG GATCTCAGCT ATTGATACTG CTGGTGACAC ATACTATCCA GGCTCCGTGA AGGGCCGATT CACCGTCTCC AGAGAAAATG CCAAGAACTC CTTTTATCTT CAAATGAACA GCCTGAGAGC CGGGGACACG GCTGTGTATT ACTGTGCAAG GGAGGGGAAG TATTACGATA TTTTGACTGG TGACTACCAC TACTACGGTA TGGACGTCTG GGGCCAAGGG ACCACGGTCA CCGTCTCC | DNA nucleotide sequence |
| 106. | EVQLVESGGA LVQPGGSLRL SCTASGFTFS NYDMHWVRQT TGKGLEWISA IDTAGDTYYP GSVKGRFTVS RENAKNSFYL QMNSLRAGDT AVYYCAREGK YYDILTGDYH YYGMDVWGQG TTVTVS | AA amino acid sequence |
| 107. | GACATCCAGA TGACCCAGTC TCCATCCTCC CTGTCTGCAT CTGTAGGAGA CAGAGTCACC ATCACTTGTC GGGCAAGTCA GGGCATTAGA AATGATTTAG CTGGTATCA GCAGAAACCA GGGAAAGCCC CTAAGCGACT GATCTATGCT ACATCCAGTT TGCAAAGTGG GGTCCCATCA AGGTTCAGCG GCAGTGGATC TGGGACAGAA TTCACTCTCA CAATCAGCAG CCTGCAGCCT GAAGATTTTG CAACTTATTA CTGTCTACAG CATAATAGTT ACCCGCTCAC TTTCGGCGGA GGGACCAAGC TGGAGATCAA A | DNA nucleotide sequence |
| 108. | DIQMTQSPSS LSASVGDRVT ITCRASQGIR NDLGWYQQKP GKAPKRLIYA TSSLQSGVPS RFSGSGSGTE FTLTISSLQP EDFATYYCLQ HNSYPLTFGG GTKLEIK | AA amino acid sequence |
| 109. | CAGGTGCAGC TGGTGCAGTC TGGGGGAGGC GTGGTCCAGC CTGGGAGGTC CCTGAGACTC TCCTGTGCAG CGTCTGGGTT CACCTTTAGT AACTTTGGCA TGCACTGGGT CCGCCAGGCT CCAGGCAAGG GGCTGGAGTG GGTGGCAGTT ATATGGTTTG ATGAAATTGA TAAATACTAT GCAGACTCCG TGAAGGGCCG ATTCACCATC TCCAGAGACA ATTCCAAGAA CACGCTGTAT CCGCAAATGA ACAGCCTGAG AGCCGAAGAC ACGGCTGTGT ATTACTGTGC GCGAGAAGAT TACGATATTT TGACTGGTTA CTATTACGCT ATGGACGTCT GGGGCCAAGG GACCACGGTC ACCGTCTCCT CA | DNA nucleotide sequence |
| 110. | QVQLVQSGGG VVQPGRSLRL SCAASGFTFS NFGMHWVRQA PGKGLEWVAV IWFDEIDKYY ADSVKGRFTI SRDNSKNTLY PQMNSLRAED TAVYYCARED YDILTGYYYA MDVWGQGTTV TVSS | AA amino acid sequence |
| 111. | GGGTTCACCT TTAGTAACTT TGGC | DNA nucleotide sequence |
| 112. | GFTFSNFG | AA amino acid sequence |
| 113. | ATATGGTTTG ATGAAATTGA TAAA | DNA nucleotide sequence |
| 114. | IWFDEIDK | AA amino acid sequence |
| 115. | GCGCGAGAAG ATTACGATAT TTTGACTGGT TACTATTACG CTATGGACGT C | DNA nucleotide sequence |

TABLE 14-continued

Informal Sequence Listing

| SEQ ID NO | Sequence | Description |
|---|---|---|
| 116. | AREDYDILTG YYYAMDV | AA amino acid sequence |
| 117. | GACATCCAGA TGACCCAGTC TCCATCCTCC CTGTCTGCAT CTGTAGGAGA CAGAGTCACC ATCACTTGCC GGGCAAGTCA GGGCATTAGA AATGATTTAG CTGGTATCA GCAGAAACCA GGGAAAGCCC CTAAGCGCCT AATCTATGCT GCATCCCGTT TGCAAAGTGG GGTCCCATCG AGGTTCAGCG GCAGTGGATC TGGGACAGAA TTCACTCTCA CAATCAGCAG CCTGCAGCCT GAAGATTTTG GAACTTATTA CTGTCTACAG CATAATAGTC ACCCCACCTT CGGCCAAGGG ACCAAGGTGG AGATCAAACG A | DNA nucleotide sequence |
| 118. | DIQMTQSPSS LSASVGDRVT ITCRASQGIR NDLGWYQQKP GKAPKRLIYA ASRLQSGVPS RFSGSGSGTE FTLTISSLQP EDFGTYYCLQ HNSHPTFGQG TKVEIKR | AA amino acid sequence |
| 119. | CAGGGCATTA GAAATGAT | DNA nucleotide sequence |
| 120. | QGIRND | AA amino acid sequence |
| 121. | GCTGCATCC | DNA nucleotide sequence |
| 122. | AAS | AA amino acid sequence |
| 123. | CTACAGCATA ATAGTCACCC CACC | DNA nucleotide sequence |
| 124. | LQHNSHPT | AA amino acid sequence |
| 125. | CAGGTGCAGC TGGTGGAGTC TGGGGGAGGC GTGGTCCAGC CTGGGAGGTC CCTGAGACTC TCCTGTGCAG CGTCTGGGTT CACCTTTAGT AACTTTGGCA TGCACTGGGT CCGCCAGGCT CCAGGCAAGG GGCTGGAGTG GGTGGCAGTT ATATGGTTTG ATGAAATTGA TAAATACTAT GCAGACTCCG TGAAGGGCCG ATTCACCATC TCCAGAGACA ATTCCAAGAA CACGCTGTAT CCGCAAATGA ACAGCCTGAG AGCCGAAGAC ACGGCTGTGT ATTACTGTGC GCGAGAAGAT TACGATATTT TGACTGGTTA CTATTACGCT ATGGACGTCT GGGGCCAAGG GACCACGGTC ACCGTCTCC | DNA nucleotide sequence |
| 126. | QVQLVESGGG VVQPGRSLRL SCAASGFTFS NFGMHWVRQA PGKGLEWVAV IWFDEIDKYY ADSVKGRFTI SRDNSKNTLY PQMNSLRAED TAVYYCARED YDILTGYYYA MDVWGQGTTV TVS | AA amino acid sequence |
| 127. | GACATCCAGA TGACCCAGTC TCCATCCTCC CTGTCTGCAT CTGTAGGAGA CAGAGTCACC ATCACTTGCC GGGCAAGTCA GGGCATTAGA AATGATTTAG CTGGTATCA GCAGAAACCA GGGAAAGCCC CTAAGCGCCT AATCTATGCT GCATCCCGTT TGCAAAGTGG GGTCCCATCG AGGTTCAGCG GCAGTGGATC TGGGACAGAA TTCACTCTCA CAATCAGCAG CCTGCAGCCT GAAGATTTTG GAACTTATTA CTGTCTACAG CATAATAGTC ACCCCACCTT CGGCCAAGGG ACCAAGGTGG AGATCAAA | DNA nucleotide sequence |
| 128. | DIQMTQSPSS LSASVGDRVT ITCRASQGIK NDLGWYQQKP GKAPKRLIYA ASRLQSGVPS RFSGSGSGTE FTLTISSLQP EDFGTYYCLQ HNSHPTFGQG TKVEIK | AA amino acid sequence |
| 129. | GAGGTGCAGC TGGTGGAGTC GGGGGGAGGC ATGGTACAGC CTGGGGGGTC CCTGAGACTC TCCTGTGCAG CCTCTGGATT CACCTCCAGT AACTACGACA TGCACTGGGT CCGCCAAGCT ACAGGAAAAG GTCTGGAGTG GGTCTCAAGT ATTGATACTG CTGGGGACAC TTACTATCCA GACTCCGTGA AGGGCCGCTT TATCATCTCC AGAGAAAATG CCAAAAACTC CCTGTATCTT CAAATGAATA GCCTGAGAGC CGGGGACACG GCTGTGTATT ACTGTACAAG GGAGCCCCGA AATTACGAAA TTTTGACTGG TCACTACCAC TACCACGGTA TGGACATCTG GGGCCAAGGG ACCACGGTCA CCGTCTCCTC A | DNA nucleotide sequence |
| 130. | EVQLVESGGG MVQPGGSLRL SCAASGFTSS NYDMHWVRQA TGKGLEWVSS IDTAGDTYYP DSVKGRFIIS RENAKNSLYL QMNSLRAGDT AVYYCTREPR NYEILTGYHY HYGMDIWGQG TTVTVSS | AA amino acid sequence |

TABLE 14-continued

Informal Sequence Listing

| SEQ ID NO | Sequence | Description |
|---|---|---|
| 131. | GGATTCACCT CCAGTAACTA CGAC | DNA nucleotide sequence |
| 132. | GFTSSNYD | AA amino acid sequence |
| 133. | ATTGATACTG CTGGGGACAC T | DNA nucleotide sequence |
| 134. | IDTAGDT | AA amino acid sequence |
| 135. | ACAAGGGAGC CCCGAAATTA CGAAATTTTG ACTGGTCACT ACCACTACCA CGGTATGGAC ATC | DNA nucleotide sequence |
| 136. | TREPRNYEIL TGHYHYHGMD I | AA amino acid sequence |
| 137. | GACATCCAGA TGACCCAGTC GCCATCCTCC CTGTCTGCAT CTGTAGGAGA CAGAGTCACC ATCACTTGCC GGGCAAGTCA GGCCATTAGA AATGATTTAG GCTGGTATCA GCAGAAACCA GGGAAAGCCC CTAAACTCCT GATCTATACT GCATTCAGTT TACAGAGTGG GGTCCCATCA AGGTTCAGCG GCAGTAAATC TGGCACAGAC TTCACTCTCA CCATCAGCAG CCTGCAGCCT GAAGATTTTG CGACTTATTA CTGTCTGCAG GATTACACTA ATCCTCGGAC GTTCGGCCAA GGGACCAAGG TGGAGATCAA ACGA | DNA nucleotide sequence |
| 138. | DIQMTQSPSS LSASVGDRVT ITCRASQAIR NDLGWYQQKP GKAPKLLIYT AFSLQSGVPS RFSGSKSGTD FTLTISSLQP EDFATYYCLQ DYTNPRTFGQ GTKVEIKR | AA amino acid sequence |
| 139. | CAGGCCATTA GAAATGAT | DNA nucleotide sequence |
| 140. | QAIRND | AA amino acid sequence |
| 141. | ACTGCATTC | DNA nucleotide sequence |
| 142. | TAF | AA amino acid sequence |
| 143. | CTGCAGGATT ACACTAATCC TCGGACG | DNA nucleotide sequence |
| 144. | LQDYTNPRT | AA amino acid sequence |
| 145. | GAGGTGCAGC TGGTGGAGTC GGGGGGAGGC ATGGTACAGC CTGGGGGGTC CCTGAGACTC TCCTGTGCAG CCTCTGGATT CACCTCCAGT AACTACGACA TGCACTGGGT CCGCCAAGCT ACAGGAAAAG GTCTGGAGTG GGTCTCAAGT ATTGATACTG CTGGGGACAC TTACTATCCA GACTCCGTGA AGGGCCGCTT TATCATCTCC AGAGAAAATG CCAAAAACTC CCTGTATCTT CAAATGAATA GCCTGAGAGC CGGGGACACG GCTGTGTATT ACTGTACAAG GGAGCCCCGA AATTACGAAA TTTTGACTGG TCACTACCAC TACCACGGTA TGGACATCTG GGGCCAAGGG ACCACGGTCA CCGTCTCC | DNA nucleotide sequence |
| 146. | EVQLVESGGG MVQPGGSLRL SCAASGFTSS NYDMHWVRQA TGKGLEWVSS IDTAGDTYYP DSVKGRFIIS RENAKNSLYL QMNSLRAGDT AVYYCTREPR NYEILTGHYH YHGMDIWGQG TTVTVS | AA amino acid sequence |

TABLE 14-continued

Informal Sequence Listing

| SEQ ID NO | Sequence | Description |
|---|---|---|
| 147. | GCCATCCAGA TGACCCAGTC GCCATCCTCC CTGTCTGCAT CTGTAGGAGA CAGAGTCACC ATCACTTGCC GGGCAAGTCA GGCCATTAGA AATGATTTAG GCTGGTATCA GCAGAAACCA GGGAAAGCCC CTAAACTCCT GATCTATACT GCATTCAGTT TACAGAGTGG GGTCCCATCA AGGTTCAGCG GCAGTAAATC TGGCACAGAC TTCACTCTCA CCATCAGCAG CCTGCAGCCT GAAGATTTTG CGACTTATTA CTGTCTGCAG GATTACACTA ATCCTCGGAC GTTCGGCCAA GGGACCAAGG TGGAAATCAA A | DNA nucleotide sequence |
| 148. | AIQMTQSPSS LSASVGDRVT ITCRASQAIR NDLGWYQQKP GKAPKLLIYT AFSLQSGVPS RFSGSKSGTD FTLTISSLQP EDFATYYCLQ DYTNPRTFGQ GTKVEIK | AA amino acid sequence |
| 149. | QVMDFLFEKW KLYGDQCHHN LSLLPPPTEL VCNRTFDKYS CWPDTPANTT ANISCPWYLP WHHKVQHRFV FKRCGPDGQW VRGPRGQPWR DASQCQMDGE EIEVQKEVAK MYSSFQVMDK THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSRDELTKNQ VSLTCLVKGF YPSDIAVEWE SNGQPENNYK TTPPVLDSDG SFFLYSKLTV DKSRWQQGNV FSCSVMHEAL HNHYTQKSLS LSPGK | DNA nucleotide sequence |
| 150. | QVMDFLFEKW KLYGDQCHHN LSLLPPPTEL VCNRTFDKYS CWPDTPANTT ANISCPWYLP WHHKVQHRFV FKRCGPDGQW VRGPRGQPWR DASQCQMDGE EIEVQKEVAK MYSSFQVMGP GDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNHYTQK SLSLSPGK | AA amino acid sequence |
| 151. | QVMDFLFEKW KLYGDQCHHN LSLLPPPTEL VCNRTFDKYS CWPDTPANTT ANISCPWYLP WHHKVQHRFV FKRCGPDGQW VRGPRGQPWR DASQCQMDGE EIEVQKEVAK MYSSFQVMEQ KLISEEDLGG EQKLISEEDL HHHHHH | AA amino acid sequence |
| 152. | GAPQVMDFLF EKWKLYGDQC HHNLSLLPPP TELVCNRTFD KYSCWPDTPA NTTANISCPW YLPWHHKVQH RFVFKRCGPD GQWVRGPRGQ PWRDASQCQM DGEEIEVQKE VAKMYSSFQV MGPGDKTHTC PPCPAPELLG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRD ELTKNQVSLT CLVKGFYPSD IAVEWESNGQ PENNYKTTPP VLDSDGSFFL YSKLTVDKSR WQQGNVFSCS VMHEALHNHY TQKSLSLSPG K | AA amino acid sequence |
| 153. | MPPCQPQRPL LLLLLLLACQ PQVPSAQVMD FLFEKWKLYG DQCHHNLSLL PPPTELVCNR TFDKYSCWPD TPANTTANIS CPWYLPWHHK VQHRFVFKRC GPDGQWVRGP RGQPWRDASQ CQMDGEEIEV QKEVAKMYSS FQVMYTVGYS LSLGALLLAL AILGGLSKLH CTRNAIHANL FASFVLKASS VLVIDGLLRT RYSQKIGDDL SVSTWLSDGA VAGCRVAAVF MQYGIVANYC WLLVEGLYLH NLLGLATLPE RSFFSLYLGI GWGAPMLFVV PWAVVKCLFE NVQCWTSNDN MGFWWILRFP VFLAILINFF IFVRIVQLLV AKLRARQMHH TDYKFRLAKS TLTLIPLLGV HEVVFAFVTD EHAQGTLRSA KLFFDLFLSS FQGLLAVLY CFLNKEVQSE LRRRWHRWRL GKVLWEERNT SNHRASSSPG HGPPSKELQF GRGGGSQDSS AETPLAGGLP RLAESPF | AA amino acid sequence |
| 154. | MALTQLHCPH LLLLLLVLSC LPEAPSAQVM DFLFEKWKLY SDQCHHNSL LPPPTELVCN RTFDKYSCWP DTPPNTTANI SCPWYLPWYH KVQHRLVFKR CGPDGQWVRG PRGQPWRNAS QCQLDDEEIE VQKGVAKMYS SQQVMYTVGY SLSLGALLLA SQQVMYTVGY SLSLGALLLA SQQVMYTVGY HCTRNYIHNG LFASFVLKAG SVLVIDWLLK TRYSQKIGDD LSVSVWLSDG AMAGCRVATV IMQYGIIANY CWLLVEGVYL YSLLSLATFS ERSFFSLYLG IGWGAPLLFV IPWVVVKCLF ENVQCWTSND NMGFWWILRI PVFLALLINF FIFVHIIHLL VAKLRAHQMH YADYKFRLAR STLTLIPLLG VHEVVFAFVT DEHAQGTLRS TKLFFDLFLS SFQGLLAVL YCFLNKEVQA ELMRRWRQWQ EGKALQEERL ASSHGSHMAP AGPCHGDPCE KLQLMSAGSS SGTGCVPSME TSLASSLPRL ADSPT | AA amino acid sequence |
| 155. | MAPCQPRRPL LLLLLLLACQ PQAPSAQVMD FLFEKWKLYG DQCHHNLSLL PPPTELVCNR TFDKYSCWPD TPANTTANIS CPWYLPWHHK VQHRFVFKRC GPDGQWVRGP RGQPWRDASQ CQMDGEELEV QKEVAKMYSS FQVMYTVGYS LSLGALLLAL AILGGISKLH CTRNAIHANL FVSFVLKASS VLVIDGLLRT RYSQKIGDDL SVSIWLSDGA VAGCRVAAVF MQYGVVANYC WLLVEGLYLH NLLGLATLPE RSFFSLYLGI GWGAPMLFII PWVVVRCLFE NIQCWTSNDN MGFWWILRFP VFLAILINFF IFIRIVHLLV AKLRAREMHH TDYKFRLAKS TLTLIPLLGV HEVVFAFVTD EHAQGTLRFA KLFFDLFLSS FQGLLAVLY CFLNKEVQSE LRRHWHRWRL GKVLQEERGT SNHKAPSAPG QGLPGKKLQS GRDGGSQDSS AEIPLAGGLP RLAESPFSTL LGPQLGLDSG T | AA amino acid sequence |
| 156. | MVLTQLHCPY LLLLLVVLSC LPKAPSAQVM DFLFEKWKLY SDQCHHNSL LPPPTELVCN RTFDKYSCWP DTPPNTTANI SCPWYLPWYH KVQHRLVFKR CGPDGQWVRG PRGQSWRDAS QCQMDDDEIE VQKGVAKMYS SYQVMYTVGY SLSLGALLLA LVILLGLRKL HCTRNYIHGN LFASFVLKAG SVLVIDWLLK TRYSQKIGDD LSVSVWLSDG AVAGCRVATV IMQYGIIANY CWLLVEGVYL YSLLSITTFS EKSFFSLYLC IGWGSPLLFV IPWVVVKCLF ENVQCWTSND NMGFWWILRI PVLLAILINF FIFVRIIHLL VAKLRAHQMH YADYKFRLAR STLTLIPLLG VHEVVFAFVT DEHAQGTLRS TKLFFDLFFS SFQGLLAVL YCFLNKEVQA ELLRRWRRWQ EGKALQEERM ASSHGSHMAP AGTCHGDPCE KLQLMSAGSS SGTGCEPSAK TSLASSLPRL ADSPT | AA amino acid sequence |

TABLE 14-continued

Informal Sequence Listing

| SEQ ID NO | Sequence | Description |
|---|---|---|
| 157. | ATGCCCCCT GCCAGCCACA GCGACCCCTG CTGCTGTTGC TGCTGCTGCT GGCCTGCCAG CCACAGGTCC CCTCCGCTCA GGTGATGGAC TTCCTGTTTG AGAAGTGGAA GCTCTACGGT GACCAGTGTC ACCACAACCT GAGCCTGCTG CCCCCTCCCA CGGAGCTGGT GTGCAACAGA ACCTTCGACA AGTATTCCTG CTGGCCGGAC ACCCCCGCCA ATACCACGGC CAACATCTCC TGCCCCTGGT ACCTGCCTTG GCACCACAAA GTGCAACACC GCTTCGTGTT CAAGAGATGC GGGCCCGACG GTCAGTGGGT GCGTGGACCC CGGGGGCAGC CTTGGCGTGA TGCCTCCCAG TGCCAGATGG ATGGCGAGGA GATTGAGGTC CAGAAGGAGG TGGCCAAGAT GTACAGCAGC TTCCAGGTGA TGTACACAGT GGGCTACAGC CTGTCCCTGG GGGCCCTGCT CCTCGCCTTG GCCATCCTGG GGGGCCTCAG CAAGCTGCAC TGCACCCGCA ATGCCATCCA CGCGAATCTG TTTGCGTCCT TCGTGCTGAA AGCCAGCTCC GTGCTGGTCA TTGATGGGCT GCTCAGGACC CGCTACAGCC AGAAAATTGG CGACGACCTC AGTGTCAGCA CCTGGCTCAG TGATGGAGCG GTGGCTGGCT GCCGTGTGGC CGCGGTGTTC ATGCAATATG GCATCGTGGC CAACTACTGC TGGCTGCTGG TGGAGGGCCT GTACCTGCAC AACCTGCTGG GCCTGGCCAC CCTCCCCGAG AGGAGCTTCT TCAGCCTCTA CCTGGGCATC GGCTGGGGTG CCCCCATGCT GTTCGTCGTC CCCTGGGCAG TGGTCAAGTG TCTGTTCGAG AACGTCCAGT GCTGGACCAG CAATGACAAC ATGGGCTTCT GGTGGATCCT GCGGTTCCCC GTCTTCCTGG CCATCCTGAT CAACTTCTTC ATCTTCGTCC GCATCGTTCA GCTGCTCGTG GCCAAGCTGC GGGCACGGCA GATGCACCAC ACAGACTACA AGTTCCGGCT GGCCAAGTCC ACGCTGACCC TCATCCCTCT GCTGGGCGTC CACGAAGTGG TCTTTGCCTT CGTGACGGAC GAGCACGCCC AGGGCACCCT GCGCTCCGCC AAGCTCTTCT TCGACCTCTT CCTCAGCTCC TTCCAGGGCC TGCTGGTGGC TGTCCTCTAC TGCTTCCTCA ACAAGGAGGT GCAGTCGGAG CTGCGGCGGC GTTGGCACCG CTGGCGCCTG GGCAAAGTGC TATGGGAGGA GCGGAACACC AGCAACCACA GGGCCTCTGC TTCGCCCGGC CACGGCCCTC CCAGCAAGGA GCTGCAGTTT GGGAGGGGTG GTGGCAGCCA GGATTCATCT GCGGAGACCC CCTTGGCTGG TGGCCTCCCT AGATTGGCTG AGAGCCCCTT CTGA | DNA nucleotide sequence |
| 158. | CAGGTGATGG ACTTCCTGTT TGAGAAGTGG AAGCTCTACG GTGACCAGTG TCACCACAAC CTGAGCCTGC TGCCCCCTCC CACGGAGCTG GTGTGCAACA GAACCTTCGA CAAGTATTCC TGCTGGCCGG ACACCCCCGC CAATACCACG GCCAACATCT CCTGCCCCTG GTACCTGCCT TGGCACCACA AAGTGCAACA CCGCTTCGTG TTCAAGAGAT GCGGGCCCGA CGGTCAGTGG GTGCGTGGAC CCCGGGGGCA GCCTTGGCGT GATGCCTCCC AGTGCCAGAT GGATGGCGAG GAGATTGAGG TCCAGAAGGA GGTGGCCAAG ATGTACAGCA GCTTCCAGGT GATG | DNA nucleotide sequence |
| 159. | QVMDFLFEKW KLYGDQCHHN LSLLPPPTEL VCNRTFDKYS CWPDTPANTT ANISCPWYLP WHHKVQHRFV FKRCGPDGQW VRGPRGQPWR DASQCQMDGE EIEVQKEVAK MYSSFQVM | AA amino acid sequence |
| 160. | GGATTCACCT TTAACAACTA TGCC | DNA nucleotide sequence |
| 161. | GFTFNNYA | AA amino acid sequence |
| 162. | ATTAGTGGTA GCGGTGGTAC TACA | DNA nucleotide sequence |
| 163. | ISGSGGTT | AA amino acid sequence |
| 164. | GCGAAAGATT CTAACTGGGG AAATTTCGAT CTC | DNA nucleotide sequence |
| 165. | AKDSNWGNFD L | AA amino acid sequence |
| 166. | CAGAGTGTTT TATACAGGTC AACAATAGG AACTTC | DNA nucleotide sequence |
| 167. | QSVLYRSNNR NF | AA amino acid sequence |
| 168. | TGGGCATCT | DNA nucleotide sequence |

TABLE 14-continued

Informal Sequence Listing

| SEQ ID NO | Sequence | Description |
|---|---|---|
| 169. | WAS | AA amino acid sequence |
| 170. | CAACAATATT ATACTACTCC GTACACT | DNA nucleotide sequence |
| 171. | QQYYTTPYT | AA amino acid sequence |
| 172. | GAGGTGCAGC TGGTGGAGTC TGGGGGAGGC TTGGTACAGC CTGGGGGGTC CCTGAGACTC TCCTGTGCAG CCTCTGGATT CACCTTTAAC AACTATGCCA TGAACTGGGT CCGCCAGGCT CCAGGAAAGG GACTGGACTG GGTCTCAACT ATTAGTGGTA GCGGTGGTAC TACAAACTAC GCAGACTCCG TGAAGGGCCG TTTCATTATT TCCCGAGACA GTTCCAAACA CACGCTGTAT CTGCAAATGA ACAGCCTGAG AGCCGAGGAC ACGGCCGTAT ATTACTGTGC GAAAGATTCT AACTGGGGAA ATTTCGATCT CTGGGGCCGT GGCACCCTGG TCACTGTCTC CTCA | DNA nucleotide sequence |
| 173. | EVQLVESGG LVQPGGSLRL SCAASGFTFN NYAMNWVRQA PGKGLDWVST ISGSGGTTNY ADSVKGRFII SRDSSKHTLY LQMNSLRAED TAVYYCAKDS NWGNFDLWGR GTLVTVSS | AA amino acid sequence |
| 174. | GACATCGTGA TGACCCAGTC TCCAGACTCC CTGGCTGTGT CTCTGGGCGA GAGGGCCACC ATCAACTGCA AGTCCAGCCA GAGTGTTTTA TACAGGTCCA ACAATAGGAA CTTCTTAGGT TGGTACCAGC AGAAACCAGG GCAGCCTCCT AATCTACTCA TTTACTGGGC ATCTACCCGG GAATCCGGGG TCCCTGACCG ATTCAGTGGC AGCGGGTCTG GGACAGATTT CACTCTCACC ATCAGCAGCC TGCAGGCTGA AGATGTGGCA GTTTATTACT GTCAACAATA TTATACTACT CCGTACACTT TTGGCCAGGG GACCAAGCTG GAGATCAAA | DNA nucleotide sequence |
| 175. | DIVMTQSPDS LAVSLGERAT INCKSSQSVL YRSNNRNFLG WYQQKPGQPP NLLIYWASTR ESGVPDRFSG SGSGTDFTLT ISSLQAEDVA VYYCQQYYTT PYTFGQGTKL EIK | AA amino acid sequence |
| 176. | GAGATGCAAC TGGTGGAGTC TGGGGGAGGC TTGGTCCAGC CTGGGGGGTC CCTGAGACTC TCCTGTGCAG CCTCTGGATT CACCTTTAGT AGTCACTGGA TGAAGTGGGT CCGCCAGGCT CCAGGGAAGG GGCTGGAGTG GGTGGCCAAC ATAAACCAAG ATGGAAGTGA GAAATACTAT GTGGACTCTG TGAAGGGCCG ATTCACCATC TCCAGAGACA ACGCCAAGAA CTCACTGTTT CTGCAAATGA ACAGCCTGAG AGCCGAGGAC ACGGCTGTGT ATTACTGTGC GAGAGATATT GTACTAATGG TCTATGATAT GGACTACTAC TACTACGGTA TGGACGTCTG GGGCCAAGGG ACCACGGTCA CCGTCTCCTC A | DNA nucleotide sequence |
| 177. | EMQLVESGGG LVQPGGSLRL SCAASGFTFS SHWMKWVRQA PGKGLEWVAN INQDGSEKYY VDSVKGRFTI SRDNAKNSLF LQMNSLRAED TAVYYCARDI VLMVYDMDYY YYGMDVWGQG TTVTVSS | AA amino acid sequence |
| 178. | GGATTCACCT TTAGTAGTCA CTGG | DNA nucleotide sequence |
| 179. | GFTFSSHW | AA amino acid sequence |
| 180. | ATAAACCAAG ATGGAAGTGA GAAA | DNA nucleotide sequence |
| 181. | INQDGSEK | AA amino acid sequence |
| 182. | GCGAGAGATA TTGTACTAAT GGTCTATGAT ATGGACTACT ACTACTACGG TATGGACGTC | DNA nucleotide sequence |
| 183. | ARDIVLMVYD MDYYYYGMDV | AA amino acid sequence |
| 184. | GATATTGTGA TGACTCAGTC TCCACTCTCC CTGCCCGTCA CCCCTGGAGA GCCGGCCTCC ATCTCCTGCA GGTCTAGTCA GAGCCTCCTG CATAGTAATG GAAACAACTA TTTGGATTGG TACCTGCAGA AGCCAGGGCA GTCTCCACAG CTCCTGATCT ATTTGGGTTC TAATCGGGCC TCCGGGGTCC CTGACAGGTT CAGTGGCAGT GGATCAGGCA CAGATTTTAC ACTGAAAATC | DNA nucleotide sequence |

TABLE 14-continued

Informal Sequence Listing

| SEQ ID NO | Sequence | Description |
|---|---|---|
| | AGCAGAGTGG AGGCTGAGGA TGTTGGGGTT TATTACTGCA TGCAAACTCT ACAAACTCCG CTCACTTTCG GCGGAGGGAC CAAGGTGGAG ATCAAA | |
| 185. | DIVMTQSPLS LPVTPGEPAS ISCRSSQSLL HSNGNNYLDW YLQKPGQSPQ LLIYLGSNRA SGVPDRFSGS GSGTDFTLKI SRVEAEDVGV YYCMQTLQTP LTFGGGTKVE IK | AA amino acid sequence |
| 186. | CAGAGCCTCC TGCATAGTAA TGGAAACAAC TAT | DNA nucleotide sequence |
| 187. | QSLLHSNGNN Y | AA amino acid sequence |
| 188. | TTGGGTTCT | DNA nucleotide sequence |
| 189. | LGS | AA amino acid sequence |
| 190. | ATGCAAACTC TACAAACTCC GCTCACT | DNA nucleotide sequence |
| 191. | MQTLQTPLT | AA amino acid sequence |
| 192. | ATGGGCACCG TCAGCTCCAG GCGGTCCTGG TGGCCGCTGC CACTGCTGCT GCTGCTGCTG CTGCTCCTGG GTCCCGCGGG CGCCCGTGCG CAGGAGGACG AGGACGGCGA CTACGAGGAG CTGGTGCTAG CCTTGCGTTC CGAGGAGGAC GGCCTGGCCG AAGCACCCGA GCACGGAACC ACAGCCACCT TCCACCGCTG CGCCAAGGAT CCGTGGAGGT TGCCTGGCAC CTACGTGGTG GTGCTGAAGG AGGAGACCCA CCTCTCGCAG TCAGAGCGCA CTGCCCGCCG CCTGCAGGCA CAGGCTGCCC GCCGGGGATA CCTCACCAAG ATCCTGCATG TCTTCCATGG CCTTCTTCCT GGCTTCCTGG TGAAGATGAG TGGCGACCTG CTGGAGCTGG CCTTGAAGTT GCCCCATGTC GACTACATCG AGGAGGACTC CTCTGTCTTT GCCCAGAGCA TCCCGTGGAA CCTGGAGCGG ATTACCCCTC CACGGTACCG GGCGGATGAA TACCAGCCCC CCGACGGAGG CAGCCTGGTG GAGGTGTATC TCCTAGACAC CAGCATACAG AGTGACCACC GGGAAATCGA GGGCAGGGTC ATGGTCACCG ACTTCGAGAA TGTGCCCGAG GAGGACGGGA CCCGCTTCCA CAGACAGGCC AGCAAGTGTG ACAGTCATGG CACCCACCTG GCAGGGGTGG TCAGCGGCCG GGATGCCGGC GTGGCCAAGG GTGCCAGCAT GCGCAGCCTG CGCGTGCTCA ACTGCCAAGG GAAGGGCACG GTTAGCGGCA CCCTCATAGG CCTGGAGTTT ATTCGAAAAA GCCAGCTGGT CCAGCCTGTG GGGCCACTGG TGGTGCTGCT GCCCCTGGCG GGTGGGTACA GCCGCGTCCT CAACGCCGCC TGCCAGCGCC TGGCGAGGGC TGGGGTCGTG CTGGTCACCG CTGCCGGCAA CTTCCGGGAC GATGCCTGCC TCTACTCCCC AGCCTCAGCT CCCGAGGTCA TCACAGTTGG GGCCACCAAT GCCCAGGACC AGCCGGTGAC CCTGGGGACT TTGGGGACCA ACTTTGGCCG CTGTGTGGAC CTCTTTGCCC CAGGGGAGGA CATCATTGGT GCCTCCAGCG ACTGCAGCAC CTGCTTTGTG TCACAGAGTG GGACATCACA GGCTGCTGCC CACGTGGCTG GCATTGCAGC CATGATGCTG TCTGCCGAGC CGGAGCTCAC CCTGGCCGAG TTGAGGCAGA GACTGATCCA CTTCTCTGCC AAAGATGTCA TCAATGAGGC CTGGTTCCCT GAGGACCAGC GGGTACTGAC CCCCAACCTG GTGGCCGCCC TGCCCCCCAG CACCCATGGG GCAGGTTGGC AGCTGTTTTG CAGGACTGTG TGGTCAGCAC ACTCGGGGCC TACACGGATG CCACAGCCA TCGCCCGCTG CGCCCCAGAT GAGGAGCTGC TGAGCTGCTC CAGTTTCTCC AGGAGTGGGA AGCGGCGGGG CGAGCGCATG GAGGCCCAAG GGGGCAAGCT GGTCTGCCGG GCCCACAACG CTTTTGGGGG TGAGGGTGTC TACGCCATTG CCAGGTGCTG CCTGCTACCC CAGGCCAACT GCAGCGTCCA CACAGCTCCA CCAGCTGAGG CCAGCATGGG GACCCGTGTC CACTGCCACC AACAGGGCCA CGTCCTCACA GGCTGCAGCT CCCACTGGGA GGTGGAGGAC CTTGGCACCC ACAAGCCGCC TGTGCTGAGG CCACGAGGTC AGCCCAACCA GTGCGTGGGC CACAGGGAGG CCAGCATCCA CGCTTCCTGC TGCCATGCCC AGGTCTGGA ATGCAAAGTC AAGGAGCATG GAATCCCGGC CCTCAGGAG CAGGTGACCG TGGCCTGCGA GGAGGGCTGG ACCCTGACTG GCTGCAGTGC CCTCCCTGGG ACCTCCCACG TCCTGGGGGC CTACGCCGTA GACAACACGT GTGTAGTCAG GAGCCGGGAC GTCAGCACTA CAGGCAGCAC CAGCGAAGAG GCCGTGACAG CCGTTGCCAT CTGCTGCCGG AGCCGGCACC TGGCCGCAGGC CTCCCAGGAG CTCCAG | DNA nucleotide sequence |
| 193. | MGTVSSRRSW WPLPLLLLLL LLLGPAGARA QEDEDGDYEE LVLALRSEED GLAEAPEHGT TATFHRCAKD PWRLPGTYVV VLKEETHLSQ SERTARRLQA QAARRGYLTK ILHVFHGLLP GFLVKMSGDL LELALKLPHV DYIEEDSSVF AQSIPWNLER ITPPRYRADE YQPPDGGSLV EVYLLDTSIQ SDHREIEGRV MVTDFENVPE EDGTRFHRQA SKCDSHGTHL AGVVSGRDAG VAKGASMRSL RVLNCQGKGT VSGTLIGLEF IRKSQLVQPV GPLVVLLPLA GGYSRVLNAA CQRLARAGVV LVTAAGNFRD DACLYSPASA PEVITVGATN AQDQPVTLGT LGTNFGRCVD LFAPGEDIIG ASSDCSTCFV SQSGTSQAAA HVAGIAAMML SAEPELTLAE LRQRLIHFSA | AA amino acid sequence |

TABLE 14-continued

Informal Sequence Listing

| SEQ ID NO | Sequence | Description |
|---|---|---|
| | KDVINEAWFP EDQRVLTPNL VAALPPSTHG AGWQLFCRTV WSAHSGPTRM ATAIARCAPD EELLSCSSFS RSGKRRGERM EAQGGKLVCR AHNAFGGEGV YAIARCCLLP QANCSVHTAP PAEASMGTRV HCHQQGHVLT GCSSHWEVED LGTHKPPVLR PRGQPNQCVG HREASIHASC CHAPGLECKV KEHGIPAPQE QVTVACEEGW TLTGCSALPG TSHVLGAYAV DNTCVVRSRD VSTTGSTSEE AVTAVAICCR SRHLAQASQE LQ | |
| 194. | EVQLVQSGGG LVHPGGSLRL SCAGSGFTFS RNAMFWVRQA PGKGLEWVSG IGTGGATNYA DSVKGRFTIS RDNAKNSLYL QMNSLRAEDM AVYYCARGRY YFDYWGQGTL VTVSS | AA amino acid sequence |
| 195. | GFTFSRNA | AA amino acid sequence |
| 196. | IGTGGAT | AA amino acid sequence |
| 197. | ARGRYYFDY | AA amino acid sequence |
| 198. | EIVLTQSPGT LSLSPGERAT LSCRASQSVS SSYLAWYQQK PGQAPRLLIF GASSRATGIP DRFSGSGSGT DFTLTISRLE PEDFAVYYCQ QYGSSPPWTF GQGTKVEIK | AA amino acid sequence |
| 199. | QSVSSSY | AA amino acid sequence |
| 200. | GAS | AA amino acid sequence |
| 201. | QQYGSSPPWT | AA amino acid sequence |
| 202. | XAA XAA XAA XAA XAA XAA<br><222> (1) . . . (1)<br><223> Xaa = Gly<br><220><br><221> VARIANT<br><222> (2) . . . (2)<br><223> Xaa = Phe<br><220><br><221> VARIANT<br><222> (3) . . . (3)<br><223> Xaa = Thr<br><220><br><221> VARIANT<br><222> (4) . . . (4)<br><223> Xaa = Phe or Ser<br><220><br><221> VARIANT<br><222> (5) . . . (5)<br><223> Xaa = Ser<br><220><br><221> VARIANT<br><222> (6) . . . (6)<br><223> Xaa = Ser or Asn<br><220><br><221> VARIANT<br><222> (7) . . . (7)<br><223> Xaa = Tyr or Phe<br><220><br><221> VARIANT<br><222> (8) . . . (8)<br><223> Xaa = Asp, Leu, or Gly | AA amino acid sequence |

TABLE 14-continued

Informal Sequence Listing

| SEQ ID NO | Sequence | Description |
|---|---|---|
| 203. | XAA XAA XAA XAA XAA XAA XAA XAA<br><221> VARIANT<br><222> (1) . . . (1)<br><223> Xaa = ILE<br><220><br><221> VARIANT<br><222> (2) . . . (2)<br><223> Xaa = Ser, Gln, Asp, or Trp<br><220><br><221> VARIANT<br><222> (3) . . . (3)<br><223> Xaa = Ser, Glu, Thr, or Phe<br><220><br><221> VARIANT<br><222> (4) . . . (4)<br><223> Xaa = Asp or Ala<br><220><br><221> VARIANT<br><222> (5) . . . (5)<br><223> Xaa = Gly or Glu<br><220><br><221> VARIANT<br><222> (6) . . . (6)<br><223> Xaa = Arg, Ile, or absent<br><220><br><221> VARIANT<br><222> (7) . . . (7)<br><223> Xaa = Asp or Glu<br><220><br><221> VARIANT<br><222> (8) . . . (8)<br><223> Xaa = Lys or Thr | AA amino acid sequence |
| 204. | XAA XAA XAA XAA XAA XAA XAA XAA XAA XAA XAA XAA XAA XAA XAA XAA XAA XAA XAA XAA<br><221> VARIANT<br><222> (1) . . . (1)<br><223> Xaa = Ala or Thr<br><220><br><221> VARIANT<br><222> (2) . . . (2)<br><223> Xaa = Lys or Arg<br><220><br><221> VARIANT<br><222> (3) . . . (3)<br><223> Xaa = Glu<br><220><br><221> VARIANT<br><222> (4) . . . (4)<br><223> Xaa = Met, Pro, Gly, or Asp<br><220><br><221> VARIANT<br><222> (5) . . . (5)<br><223> Xaa = Val, Ser, Lys, Arg, or absent<br><220><br><221> VARIANT<br><222> (6) . . . (6)<br><223> Xaa = Tyr, His, Asn, or absent<br><220><br><221> VARIANT<br><222> (7) . . . (7)<br><223> Xaa = Tyr<br><220><br><221> VARIANT<br><222> (8) . . . (8)<br><223> Xaa = Asp or Glu<br><220><br><221> VARIANT<br><222> (9) . . . (9)<br><223> Xaa = Ile<br><220> | AA amino acid sequence |

TABLE 14-continued

Informal Sequence Listing

| SEQ ID NO | Sequence | Description |
|---|---|---|
| | `<221> VARIANT`<br>`<222> (10) . . . (10)`<br>`<223> Xaa = Leu`<br>`<220>`<br>`<221> VARIANT`<br>`<222> (11) . . . (11)`<br>`<223> Xaa = Thr`<br>`<220>`<br>`<221> VARIANT`<br>`<222> (12) . . . (12)`<br>`<223> Xaa = Gly`<br>`<220>`<br>`<221> VARIANT`<br>`<222> (13) . . . (13)`<br>`<223> Xaa = Tyr, Asp, or His`<br>`<220>`<br>`<221> VARIANT`<br>`<222> (14) . . . (14)`<br>`<223> Xaa = His, Asp, Tyr, or absent`<br>`<220>`<br>`<221> VARIANT`<br>`<222> (15) . . . (15)`<br>`<223> Xaa = Asn, Tyr, His, or absent`<br>`<220>`<br>`<221> VARIANT`<br>`<222> (16) . . . (16)`<br>`<223> Xaa = Tyr`<br>`<220>`<br>`<221> VARIANT`<br>`<222> (17) . . . (17)`<br>`<223> Xaa = Tyr or His`<br>`<220>`<br>`<221> VARIANT`<br>`<222> (18) . . . (18)`<br>`<223> Xaa = Gly or Ala`<br>`<220>`<br>`<221> VARIANT`<br>`<222> (19) . . . (19)`<br>`<223> Xaa = Met`<br>`<220>`<br>`<221> VARIANT`<br>`<222> (20) . . . (20)`<br>`<223> Xaa = Asp`<br>`<220>`<br>`<221> VARIANT`<br>`<222> (21) . . . (21)`<br>`<223> Xaa = Val or ILE` | |
| 205. | XAA XAA XAA XAA XAA XAA<br>`<221> VARIANT`<br>`<222> (1) . . . (1)`<br>`<223> Xaa = Gln`<br>`<220>`<br>`<221> VARIANT`<br>`<222> (2) . . . (2)`<br>`<223> Xaa = Gly or Ala`<br>`<220>`<br>`<221> VARIANT`<br>`<222> (3) . . . (3)`<br>`<223> Xaa = ILE`<br>`<220>`<br>`<221> VARIANT`<br>`<222> (4) . . . (4)`<br>`<223> Xaa = Asn or Arg`<br>`<220>`<br>`<221> VARIANT`<br>`<222> (5) . . . (5)`<br>`<223> Xaa = Asn`<br>`<220>`<br>`<221> VARIANT`<br>`<222> (6) . . . (6)`<br>`<223> Xaa = Tyr or Asp` | AA amino acid sequence |

TABLE 14-continued

Informal Sequence Listing

| SEQ ID NO | Sequence | Description |
|---|---|---|
| 206. | XAA XAA XAA<br><221> VARIANT<br><222> (1) . . . (1)<br><223> Xaa = Thr or Ala<br><220><br><221> VARIANT<br><222> (2) . . . (2)<br><223> Xaa = Ala or Thr<br><220><br><221> VARIANT<br><222> (3) . . . (3)<br><223> Xaa = Ser or Phe | AA amino acid sequence |
| 207. | XAA XAA XAA XAA XAA XAA XAA XAA XAA<br><221> VARIANT<br><222> (1) . . . (1)<br><223> Xaa = Gln or Leu<br><220><br><221> VARIANT<br><222> (2) . . . (2)<br><223> Xaa = Gln<br><220><br><221> VARIANT<br><222> (3) . . . (3)<br><223> Xaa = Tyr, His, or Asp<br><220><br><221> VARIANT<br><222> (4) . . . (4)<br><223> Xaa = Asn or Tyr<br><220><br><221> VARIANT<br><222> (5) . . . (5)<br><223> Xaa = Thr or Ser<br><220><br><221> VARIANT<br><222> (6) . . . (6)<br><223> Xaa = Tyr, Asn, or His<br><220><br><221> VARIANT<br><222> (7) . . . (7)<br><223> Xaa = Pro<br><220><br><221> VARIANT<br><222> (8) . . . (8)<br><223> Xaa = Leu, Phe, Arg, or absent<br><220><br><221> VARIANT<br><222> (9) . . . (9)<br><223> Xaa = Thr | AA amino acid sequence |

What is claimed is:

1. An isolated human antibody or antigen-binding fragment thereof that specifically binds human glucagon receptor (hGCGR), comprising:
   (a) a heavy chain complementarity determining region 1 (HCDR1) amino acid sequence as set forth in SEQ ID NO: 36 with no more than one amino acid substitution;
   (b) an HCDR2 amino acid sequence as set forth in SEQ ID NO: 38 with no more than one amino acid substitution;
   (c) an HCDR3 amino acid sequence as set forth in SEQ ID NO: 40 with no more than one amino acid substitution;
   (d) an LCDR1 amino acid sequence as set forth in SEQ ID NO: 44 with no more than one amino acid substitution;
   (e) an LCDR2 amino acid sequence as set forth in SEQ ID NO: 46 with no more than one amino acid substitution; and
   (f) an LCDR3 amino acid sequence as set forth in SEQ ID NO: 48 with no more than one amino acid substitution.

2. The isolated antibody or antigen-binding fragment thereof of claim 1, comprising a heavy chain variable region (HCVR) amino acid sequence having at least 95% sequence identity to SEQ ID NO: 34 and a light chain variable region sequence (LCVR) amino acid sequence having at least 95% sequence identity to SEQ ID NO: 42.

3. The isolated antibody or antigen-binding fragment thereof of claim 2, comprising an HCVR amino acid sequence having at least 98% sequence identity to SEQ ID NO: 34 and an LCVR amino acid sequence having at least 98% sequence identity to SEQ ID NO: 42.

4. An antibody or antigen-binding fragment thereof that competes for specific binding to hGCGR with the antibody or antigen-binding fragment thereof of claim 1.

5. An antibody or antigen-binding fragment thereof that binds the same epitope on hGCGR as the antibody or antigen-binding fragment thereof of claim 1.

6. A pharmaceutical composition comprising the antibody or antigen-binding fragment thereof of claim 1 and a pharmaceutically acceptable carrier or diluent.

7. The isolated human antibody or antigen-binding fragment thereof of claim 1, comprising: an HCVR amino acid sequence of SEQ ID NO: 36 with no more than 3 amino acid substitutions; and an LCVR amino acid sequence of SEQ ID NO: 42 with no more than 3 amino acid substitutions.

8. The isolated human antibody or antigen-binding fragment thereof of claim 1, comprising: an HCVR amino acid sequence of SEQ ID NO: 36 with no more than 2 amino acid substitutions; and an LCVR amino acid sequence of SEQ ID NO: 42 with no more than 2 amino acid substitutions.

9. The isolated human antibody or antigen-binding fragment thereof of claim 1, comprising: an HCVR amino acid sequence of SEQ ID NO: 36 with no more than 1 amino acid substitutions; and an LCVR amino acid sequence of SEQ ID NO: 42 with no more than 1 amino acid substitutions.

10. The isolated antibody or antigen-binding fragment thereof of claim 1, wherein the HCDR1 is encoded by a nucleotide sequence having at least 95% sequence identity to SEQ ID NO: 35; the HCDR2 is encoded by a nucleotide sequence having at least 95% sequence identity to SEQ ID NO: 37; the HCDR3 is encoded by a nucleotide sequence having at least 95% sequence identity to SEQ ID NO: 39; the LCDR1 is encoded by a nucleotide sequence having at least 95% sequence identity to SEQ ID NO: 43; the LCDR2 is encoded by a nucleotide sequence of SEQ ID NO: 45; and the LCDR3 is encoded by a nucleotide sequence having at least 95% sequence identity to SEQ ID NO: 47.

11. The isolated antibody or antigen-binding fragment thereof of claim 2, wherein the HCVR is encoded by a nucleotide sequence having at least 95% sequence identity to SEQ ID NO: 33 and the LCVR is encoded by a nucleotide sequence having at least 95% sequence identity to SEQ ID NO: 41.

12. The isolated antibody or antigen-binding fragment thereof of claim 2, wherein the HCVR is encoded by a nucleotide sequence having at least 98% sequence identity to SEQ ID NO: 33 and the LCVR is encoded by a nucleotide sequence having at least 98% sequence identity to SEQ ID NO: 41.

13. A pharmaceutical composition comprising the antibody or antigen-binding fragment thereof of claim 1, and a second therapeutic agent comprising an isolated antibody, or an antigen-binding fragment thereof, that specifically binds to PCSK9, and a pharmaceutically acceptable carrier or diluent.

14. A method for lowering blood glucose or ketone levels, or for treating a condition or disease associated with, or characterized in part by high blood glucose or ketone levels, or at least one symptom or complication associated with the condition or disease, the method comprising administering the pharmaceutical composition of claim 6, to a patient in need thereof, such that blood glucose or ketone levels are lowered or that the condition or disease is mediated, or at least one symptom or complication associated with the condition or disease is alleviated or reduced in severity.

15. The method of claim 14, wherein the condition or disease is selected from the group consisting of diabetes, impaired glucose tolerance, obesity, nephropathy, neuropathy, retinopathy, cataracts, stroke, atherosclerosis, impaired wound healing, diabetic ketoacidosis, hyperglycemia, hyperglycemic hyperosmolar syndrome, perioperative hyperglycemia, hyperglycemia in the intensive care unit patient, hyperinsulinemia, the metabolic syndrome, insulin resistance syndrome and impaired fasting glucose.

16. The method of claim 14, wherein the pharmaceutical composition is administered to the patient in combination with a second therapeutic agent.

17. The method of claim 16, wherein the second therapeutic agent is selected from the group consisting of insulin, a biguanide (metformin), a sulfonylurea (glyburide, glipizide), a PPAR gamma agonist (pioglitazone, rosiglitazone), an alpha glucosidase inhibitor (acarbose, voglibose), glucagon-like peptide 1, pramlintide, a glucagon antagonist, and a second GCGR antagonist.

18. The method of claim 16, wherein the second therapeutic agent is a 3-hydroxy-3-methyl-glutaryl-CoA reductase (HMG-COA reductase) inhibitor.

19. The method of claim 18, wherein the HMG-COA reductase inhibitor is a statin selected from the group consisting of atorvastatin, fluvastatin, lovastatin, pitavastatin, pravastatin, rosuvastatin and simvastatin.

20. The method of claim 16, wherein the second therapeutic agent is an isolated antibody, or an antigen-binding fragment thereof, that specifically binds to human proprotein convertase subtilisin/kexin type 9 (PCSK9).

* * * * *